United States Patent [19]
Cochran et al.

[11] Patent Number: 5,382,425
[45] Date of Patent: Jan. 17, 1995

[54] RECOMBINANT SWINEPOX VIRUS

[75] Inventors: Mark D. Cochran, Carlsbad; David E. Junker, San Diego, both of Calif.

[73] Assignee: Syntro Corporation, Lenexa, Kans.

[21] Appl. No.: 820,154

[22] Filed: Jan. 13, 1992

[51] Int. Cl.$^6$ .............. C12P 21/02; C12P 19/34; C12N 15/00; C12N 7/00; C12N 5/00; C07K 3/00; C07H 15/12
[52] U.S. Cl. ................... 435/69.1; 435/69.3; 435/172.3; 435/235.1; 435/320.1; 435/240.2; 536/23.72; 530/350; 935/9; 935/32; 935/36; 935/57; 935/63; 935/70
[58] Field of Search .............. 435/235.1, 69.3, 91, 435/172.3, 240.2; 536/27; 530/350; 424/89; 935/9, 32, 36, 57, 63, 70

[56] References Cited

U.S. PATENT DOCUMENTS 5,225,336 7/1993 Paoletti et al. .................. 435/69.1

FOREIGN PATENT DOCUMENTS 0261940 3/1988 European Pat. Off. ...... C12N 15/00

OTHER PUBLICATIONS

Marchioli et al. J. Virol. vol. 16 pp. 3977–3982.

Primary Examiner—Joan Ellis
Attorney, Agent, or Firm—John P. White

[57] ABSTRACT

The present invention relates to a recombinant swinepox virus capable of replication comprising foreign DNA inserted into a site in the swinepox viral DNA which is not essential for replication of the swinepox virus. The invention further relates to homology vectors which produce recombinant swinepox viruses by inserting foreign DNA into swinepox viral DNA.

20 Claims, 19 Drawing Sheets

FIGURE 2A

```
AATGTATCCAGAGTTGTTGAATGCCTTATCGTACCTAATATATTAATATAGAGTTATTAACT
GAATAAGTATATATAAAGATTGTTTTATATGTTTGTTATCGCATTTAGTTTTGCTGT
ATGGTTATCATATACATTTTTAAGGCCGTATATGATAAATGAAAATATATAAGCACTTAT
ATGGTTATCATATAACAATGCCGTCGTATATGTCCGAAGAACGCAAGAAAAGTA
TTTGTTAGTATATAATAACAATGCCGTCGTATATGTCCGAAGAACGCAAGAAAAGTA
              MetProSer......
ATTCAAAGATTATATCATTACAACTTGATATTAAAAACTTCCTAAAAATATATAAAT
ACCATGTTAGAATTTGGTCTCTACATGGAAATCTACCAGCTTGTATGTATAAAGATGCCGTA
TCATATGATATAATAAATAAGATTTTTACCTTATAATTGTGTTATGGTTAAAGATTTA
ATAAATGTTATAAATCATCATCTGTAATAGATACTAGATTATCACTTTAATGATCATTAAT
CATCGTAGAGCCGTTAATAGATTACGGCGATCAAGACATTATCACTTTAATGATCATTAAT
AAGTTACTATCGATAGATGATATCCTATATATTAGATAAAAAAATAATTCATGTAAC
                                                ...IleHisVal
```

FIGURE 2B

```
GAGATATTAAATCATGTAAATGCTCGATATGTTCCGACTCTATAACACATCATATATG
 AspIleLysSer.........
AAACAACATCATGTATAAATTATAAATCTACCGATAATGATCTTATGATAGTATTGTTCA
ATCTAACTAGATATATTTAATGCATGGATGATACATCCTAATCTTATAAGCGTAAAGGAT
GGGGTCCCCTTATTGGATTATTAACGGGTGATATAGGTATTAATTTAAACTATATTCCA
CCATGATAAATGGGCTACGGTATGGAGATATTACGTTATCTTCATACGATATGAGTA
ATAAATTAGTCTCTATTATTAATACACCCATATGAGTTAATACCGTTACTACATGTT
GTTCACTCAATGAATATTATTCAAAATTGTGATTTTAATAAATGTTATTTTAGAATATA
TGATATCTATTATATATATAGAATATATGATCGTAAAAGATTAATAACATTAAAGAAT
TTATTTCAAAAGTCGTAAATACTGTACTAGAATCATCAGGCATATATTTTTGTCAGATGC
GTGTACATGAACAAATTGAATTGGAAATAGATGAGCTCATTATTAATGGATCTATGCCTG
TACAGCTTATGCATTTACTTCTAAAGGTAGCTACCATAATATATTAGAGAATCAAAGAAA
                                    ....... LysGluI
TATAACGTATTTTTTCTTTTAAATAAAATACTTTTTTTTTTTTAAACAAGGGGTGCT
le---
ACCTTGTCTAATTGTATCTTGTTATTTTGGATCTGATGCAAGATTATTAAATAATCGTATG
AAAAGTAGTAGATATAGTTTATATCGTTACTGACATGATATTATGTTTAGTTAATTCT
TCTTTGGCATGAATTCTACACGTCGGANAAGGTAATGTATCTATATGGTATAAAGCTT
```

FIGURE 3B

```
                        10        20        30        40        50        60        70
                         *         *         *         *         *         *         *
(A) VV      MFMYPEFARKALSKLISKKLNIEKVSSKHQLVLLDYGLHGLLPKSLYLEAINSDILNVRFFPPEIINVT
orf O1L        :::  :::  :: ::  : : :   :     |  |  :: ::  :  :  :: : :: :     :
(B) SPV    MPSYMYPKNARKVISKIISLQLDIKKLPKKYINTMLEFGLHGNLPACMYKDAVSYDINNIRFLPYNCVMVK
AccI-ClaI                                        |
                                                AccI 80        90       100       110       120
                    *         *         *         *         *
(A) VV      DIVKALQNSCRVDEYLKAVSLYHKNSLMVSGPNVVK-LMIEYNLLTHSDLEWLINENVVKA
orf O1L     :       :  :  :    : :  :   :       :::   ::   :
(B) SPV     DLINVIKSSSVIDTRLHQSVLKHRRALIDYGDQDIITLMIINKLLSIDDISYILDKKIIHV
AccI-ClaI                                                |
                                                        ClaI
```

FIGURE 3C

```
                           570       580       590       600       610
                             *         *         *         *         *
(C) VV orf O1L          VLNDQYAKIVIFFNTIIEYIIATIYYRLTVLNNYTNVKHFVSKVLHTVMEA
(D) SPV EcoRV-EcoRI     SLNEYYSKIVILINVILEYMISIILYRILIVKRFNNIKEFISKVVNTVLES
                                              |
                                            EcoRV TERM
                           620       630       640       650       660    |
                             *         *         *         *         *    |
(C) VV orf O1L          CGVLFSYIKVNDKIEHELEEMVDKGTVPSYLYHLSINVISIILDDINGTR-
(D) SPV EcoRV-EcoRI     SGIYFCQMRVHEQIELEIDELIINGSMPVQLMHLLLKVATIILEEIKEI-  ——→ EcoRI
                                                                         |
                                                                       TERM
```

FIGURE 5A
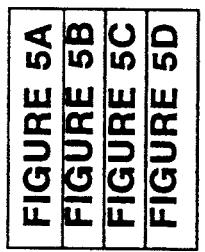
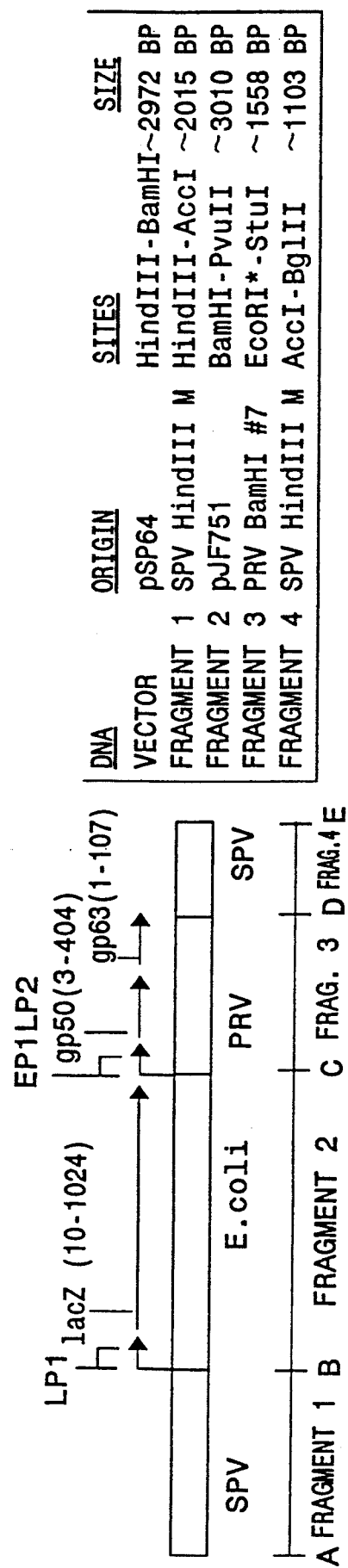

FIGURE 7

```
ACGGGTAGAACGGTAAGAGAGGCCGCCCCTCAATTGCGAGCCAGACTTCACAACCTCCGT
                                             AvaII
                                             ┌/─┐
TCTACCGCTTCACCGACAACAGTCCTCAATCATGGACCGCGCCGTTAGCCAAGTTGCGTT
                              MetAspArg.............
AGAGAATGATGAAAGAGAGGCAAAAAATACATGGCGCTTGATATTCCGGATTGCAATCTT
ATTCTTAACAGTAGTGACCTTGGCTATATCTGTAGCCTCCCTTTTATATAGCATGGGGGC
TAGCACACCTAGCGATCTTGTAGGCATACCGACTAGGATTTCCAGGGCAGAAGAAAAGAT
TACATCTACACTTGGTTCCAATCAAGATGTAGTAGATAGGATATATAAGCAAGTGGCCCT
TGAGTCTCCATTGGCATTGTTAAATACTGAGACCACAATTATGAACGCAATAACATCTCT
CTCTTATCAGATTAATGGAGCTGCAAACAACAGCGGGTGGGGGCACCTATTCATGACCC
AGATTATATAGGGGGATAGGCAAAGAACTCATTGTAGATGATGCTAGTGATGTCACATC
ATTCTATCCCTCTGCATTTCAAGAACATCTGAATTTTATCCCGGCGCCTACTACAGGATC
AGGTTGCACTCGAATACCCTCATTTGACATGAGTGCTACCCATTACTGCTACACCCATAA
TGTAATATTGTCTGGATGCAGAGATCACTCACACTCACATCAGTATTTAGCACTTGGTGT
GCTCCGGACATCTGCAACAGGGAGGGTATTCTTTTCTACTCTGCGTTCCATCAACCTGGA
CGACACCCAAAATCGGAAGTCTTGCAGTGTGAGTGCAACTCCCCTGGGTTGTGATATGCT
GTGCTCGAAAGCCACGGAGACAGAGGAAGAAGATTATAACTCAGCTGTCCCTACGCGGAT
GGTACATGGGAGGTTAGGGTTCGACGGCCAATATCACGAAAGGACCTAGATGTCACAAC
ATTATTCGGGGACTGGGTGGCCAACTACCCAGGAGTAGGGGGTGGATCTTTTATTGACAG
CCGCGTGTGGTTCTCAGTCTACGGAGGGTTAAAACCCAATACACCCAGTGACACTGTACA
GGAAGGGAAATATGTGATATACAAGCGATACAATGACACATGCCCAGATGAGCAAGACTA
CCAGATTCGAATGGCCAAGTCTTCGTATAAGCCTGGACGGTTTGGTGGGAAACGCATACA
GCAGGCTATCTTATCTATCAAAGTGTCAACATCCTTAGGCGAAGACCCGGTACTGACTGT
ACCGCCCAACACAGTCACACTCATGGGGGCCGAAGGCAGAATTCTCACAGTAGGGACATC
CCATTTCTTGTATCAGCGAGGGTCATCATACTTCTCTCCCGCGTTATTATATCCTATGAC
AGTCAGCAACAAAACAGCCACTCTTCATAGTCCTTATACATTCAATGCCTTCACTCGGCC
AGGTAGTATCCCTTGCCAGGCTTCAGCAAGATGCCCCAACTCATGTGTTACTGGAGTCTA
TACAGATCCATATCCCCTAATCTTCTATAGAAACCACACCTTGCGAGGGGTATTCGGGAC
AATGCTTGATGGTGAACAAGCAAGACTTAACCCTGCGTCTGCAGTATTCGATAGCACATC
CCGCAGTCGCATAACTCGAGTGAGTTCAAGCAGCATCAAAGCAGCATACACAACATCAAC
TTGTTTTAAAGTGGTCAAGACCAATAAGACCTATTGTCTCAGCATTGCTGAAATATCTAA
TACTCTCTTCGGAGAATTCAGAATCGTCCCGTTACTAGTTGAGATCCTCAAAGATGACGG
GGTTAGAGAAGCCAGGTCTGGCTAGTTGAGTCAACTATGAAAGAGTTGGAAAGATGGCAT
............ArgSerGly---
                                                    NaeI
                                                    ┌─/─┐
TGTATCACCTATCTTCTGCGACATCAAGAATCAAACCGAATGCCGGC
```

RECOMBINANT SWINEPOX VIRUS

Within this application several publications are referenced by arabic numerals within parentheses. Full citations for these publications may be found at the end of the specification immediately preceding the claims. The disclosures of these publications are hereby incorporated by reference into this application in order to more fully describe the state of the art to which this invention pertains.

BACKGROUND OF THE INVENTION

Swinepox virus (SPV) belongs to the family Poxviridae. Viruses belonging to this group are large, double-stranded DNA viruses that characteristically develop in the cytoplasm of the host cell. SPV is the only member of the genus Suipoxvirus. Several features distinguish SPV from other poxviruses. SPV exhibits species specificity (18) compared to other poxviruses such as vaccinia which exhibit a broad host range. SPV infection of tissue culture cell lines also differs dramatically from other poxviruses (24). It has also been demonstrated that SPV does not exhibit antigenic cross-reactivity with vaccinia virus and shows no gross detectable homology at the DNA level with the ortho, lepori, avi or entomopox virus groups (24). Accordingly, what is known and described in the prior art regarding other poxviruses does not pertain a priori to swinepox virus.

SPV is only mildly pathogenic, being characterized by a self-limiting infection with lesions detected only in the skin and regional lymph nodes. Although the SPV infection is quite limited, pigs which have recovered from SPV are refractory to challenge with SPV, indicating development of active immunity (18).

The present invention concerns the use of SPV as a vector for the delivery of vaccine antigens and therapeutic agents to swine. The following properties of SPV support this rationale: SPV is only mildly pathogenic in swine, SPV is species specific, and SPV elicits a protective immune response. Accordingly, SPV is an excellent candidate for a viral vector delivery system, having little intrinsic risk which must be balanced against the benefit contributed by the vector's vaccine and therapeutic properties.

The prior art for this invention stems first from the ability to clone and analyze DNA while in bacterial plasmids. The techniques that are available are detailed for the most part in Maniatis et al., 1983 and Sambrook et al., 1989. These publications teach state of the art general recombinant DNA techniques.

Among the poxviruses, five (vaccinia, fowlpox, canarypox, pigeon, and raccoon pox) have been engineered, previous to this disclosure, to contain foreign DNA sequences. Vaccinia virus has been used extensively to vector foreign genes (25) and is the subject of U.S. Pat. Nos. 4,603,112 and 4,722,848. Similarly, fowlpox has been used to vector foreign genes and is the subject of several patent applications EPA 0 284 416, PCT WO from the rabies virus. These examples of insertions of foreign genes into poxviruses do not include an example from the genus Suipoxvirus. Thus, they do not teach methods to genetically engineer swinepox viruses, that is, where to make insertions and how to get expression in swinepox virus.

The idea of using live viruses as delivery systems for antigens has a very long history going back to the first live virus vaccines. The antigens delivered were not foreign but were naturally expressed by the live virus in the vaccines. The use of viruses to deliver foreign antigens in the modern sense became obvious with the recombinant vaccinia virus studies. The vaccinia virus was the vector and various antigens from other disease causing viruses were the foreign antigens, and the vaccine was created by genetic engineering. While the concept became obvious with these disclosures, what was not obvious was the answer to a more practical question of what makes the best candidate virus vector. In answering this question, details of the pathogenicity of the virus, its site of replication, the kind of immune response it elicits, the potential it has to express foreign antigens, its suitability for genetic engineering, its probability of being licensed by regulatory agencies, etc, are all factors in the selection. The prior art does not teach these questions of utility.

The prior art relating to the use of poxviruses to deliver therapeutic agents relates to the use of a vaccinia virus to deliver interleukin-2 (12). In this case, although the interleukin-2 had an attenuating effect on the vaccinia vector, the host did not demonstrate any therapeutic benefit.

The therapeutic agent that is delivered by a viral vector of the present invention must be a biological molecule that is a by-product of swinepox virus replication. This limits the therapeutic agent in the first analysis to either DNA, RNA or protein. There are examples of therapeutic agents from each of these classes of compounds in the form of anti-sense DNA, anti-sense RNA (16), ribozymes (34), suppressor tRNAs (2), interferon-inducing double stranded RNA and numerous examples of protein therapeutics, from hormones, e.g., insulin, to lymphokines, e.g., interferons and interleukins, to natural opiates. The discovery of these therapeutic agents and the elucidation of their structure and function does not make obvious the ability to use them in a viral vector delivery system.

SUMMARY OF THE INVENTION

The invention provides a recombinant swinepox virus capable of replication which comprises swinepox viral DNA and foreign DNA encoding RNA which does not naturally occur in an animal into which the recombinant swinepox virus is introduced. The foreign DNA is inserted into the swinepox viral DNA at a site which is not essential for replication of the swinepox virus and is under the control of a promoter.

This invention provides a homology vector for producing a recombinant swinepox virus by inserting foreign DNA into the genomic DNA of a swinepox virus which comprises a double-stranded DNA molecule. This molecule consists essentially of double-stranded foreign DNA encoding RNA which does not naturally occur in an animal into which the recombinant swinepox virus is introduced. At one end of this foreign DNA is double-stranded swinepox viral DNA homologous to genomic DNA located at one side of a site on the genomic DNA which is not essential for replication of the swinepox virus. At the other end of the foreign DNA is double-stranded swinepox viral DNA homologous to genomic DNA located at the other side of the same site on the genomic DNA.

BRIEF DESCRIPTION OF THE FIGURES

FIG. 7 DNA sequence of NDV Hemagglutinin-Neuraminidase gene (HN) (SEQ ID NO: 29). The sequence of 1907 base pairs of the NDV HN cDNA clone are shown. The translational start and stop of the HN gene is indicated by the amino acid translation below the DNA sequence.

DETAILED DESCRIPTION OF THE INVENTION

Figure 1:
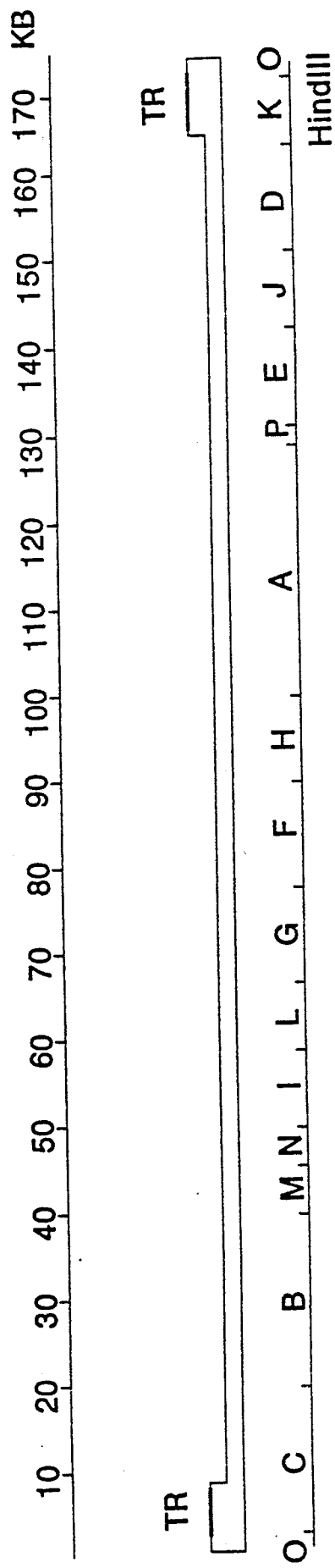
FIG. 1 Details of the SPV Kasza Strain, Diagram of SPV genomic DNA showing the unique long and Terminal repeat (TR) regions, A restriction map for the enzyme HindIII is indicated (23), Fragments are lettered in order of decreasing size. Note that the terminal repeats are greater than 2.1 kb but less than 9.7 kb in size, FIG. 2 (2A and 2B) DNA sequence from homology vector 515-85.1. The sequence of two regions of the homology vector 515-85.1 are shown, The first region (FIG. 2A) (SEQ ID NO:1) covers a 599 base pair sequence which flanks the unique AccI site as indicated in FIG. 3. The beginning (Met) and end (Val) of a 115 amino acid ORF is indicated by the translation of amino acids below the DNA sequence. The second region (FIG. 2B) (SEQ ID NO:3) covers the 899 base pairs upstream of the unique HindIII site as indicated in FIG. 3. The beginning (Asp) and end (Ile) of a 220 amino acid ORF is indicated by the translation of amino acids below the DNA sequence.

The present invention provides a recombinant swinepox virus (SPV) capable of replication in an animal into which the recombinant swinepox virus is introduced which comprises swinepox viral DNA and foreign DNA encoding RNA which does not naturally occur in the animal into which the recombinant swinepox virus is introduced, the foreign DNA being inserted into the swinepox viral DNA at an insertion site which is not essential for replication of the swinepox virus and being under the control of a promoter.

For purposes of this invention, "a recombinant swinepox virus capable of replication" is a live swinepox virus which has been generated by the recombinant methods well known to those of skill in the art, e.g., the methods set forth in HOMOLOGOUS RECOMBINATION PROCEDURE FOR GENERATING RECOMBINANT SPV in Materials and Methods and has not had genetic material essential for the replication of the recombinant swinepox virus deleted.

For purposes of this invention, "an insertion site which is not essential for replication of the swinepox virus" is a location in the genome where a sequence of DNA is not necessary for viral replication, for example, complex protein binding sequences, sequences which code for reverse transcriptase or an essential glycoprotein, DNA sequences necessary for packaging, etc.

For purposes of this invention, a "promoter" is a specific DNA sequence on the DNA molecule to which the foreign RNA polymerase attaches and at which transcription of the foreign RNA is initiated.

The invention further provides foreign RNA which encodes a polypeptide. Preferably, the polypeptide is antigenic in the animal. Preferably, this antigenic polypeptide is a linear polymer of more than 10 amino acids linked by peptide bonds which stimulates the animal to produce antibodies.

The invention further provides an insertion site present within the larger HindIII to BglII subfragment of the HindIII M fragment of swinepox viral DNA. Preferably, the insertion site is within an open reading frame contained in the HindIII to BglII subfragment. Preferably, the insertion site is the AccI restriction endonuclease site located in the HindIII to BglII subfragment.

The invention further provides an insertion site within an open reading frame encoding swinepox thymidine kinase.

For purposes of this invention, an "open reading frame" is a segment of DNA which contains codons that can be transcribed into RNA which can be translated into an amino acid sequence and which does not contain a termination codon.

The invention further provides a recombinant swinepox virus comprising foreign DNA encoding RNA encoding an antigenic polypeptide which is or is from pseudorabies virus (PRV) glycoprotein 50, pseudorabies virus (PRV) glycoprotein II, Pseudorabies virus (PRV) glycoprotein III, Pseudorabies virus (PRV) glycoprotein H, Transmissible gastroenteritis (TGE) glycoprotein 195, Transmissible gastroenteritis (TGE) matrix protein, swine rotavirus glycoprotein 38, swine parvovirus capsid protein, *Serpulina hyodysenteriae* protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is Pseudorabies Virus (PRV) glycoprotein 50. Preferably, the antigenic protein is Newcastle Disease Virus (NDV) hemagglutinin-neuraminidase.

The invention further provides a recombinant swinepox virus comprising foreign DNA encoding RNA encoding an antigenic polypeptide which is or is from *Serpulina hyodysenteriae*, Foot and Mouth Disease Virus, Hog Cholera Virus, Swine Influenza Virus, African Swine Fever Virus or *Mycoplasma hyopneumoniae*.

The invention further provides a recombinant swinepox virus where the foreign DNA encodes RNA which encodes a polypeptide which is a detectable marker. Preferably the detectable marker is the polypeptide *E. coli* β-galactosidase. For purposes of this invention, a "polypeptide which is a detectable marker" includes the bimer, trimer and tetramer form of the polypeptide. *E. coli* β-galactosidase is a tetramer composed of four polypeptides or monomer sub-units. Preferably, this recombinant swinepox virus is designated S-SPV-003 (ATCC Accession No. VR2335). The S-SPV-003 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2335.

The invention further provides for a recombinant swinepox virus capable of replication which contains foreign DNA encoding RNA encoding the antigenic polypeptide pseudorabies virus (PRV) glycoprotein 50 further comprising foreign DNA encoding a polypeptide which is a detectable marker. Preferably, this recombinant swinepox virus is designated S-SPV-008 (ATCC Accession No. VR 2339). The S-SPV-008 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2339.

The invention further provides for a recombinant swinepox virus capable of replication which contains foreign DNA encoding RNA encoding the antigenic polypeptide Newcastle Disease Virus (NDV) hemagglutinin-neuraminidase further comprising foreign DNA encoding a polypeptide which is a detectable marker. Preferably, this recombinant swinepox virus is designated S-SPV-009 (ATCC Accession No. VR 2344). The S-SPV-009 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2344.

The invention further provides that the inserted foreign DNA is under the control of a promoter. Preferably, the promoter is a swinepox viral promoter. Preferably, the promoter is a synthetic pox viral promoter. For purposes of this invention, the promoters were generated by methods well known to those of skill in the art, for example, as set forth in the STRATEGY FOR THE CONSTRUCTION OF SYNTHETIC POX VIRAL PROMOTERS in Materials and Methods. For purposes of this invention, a synthetic pox promoter includes a synthetic late pox promoter, a synthetic early pox promoter or a synthetic early/late pox promoter.

The invention provides for a homology vector for producing a recombinant swinepox virus by inserting foreign DNA into the genomic DNA of a swinepox virus. The homology vector comprises a double-stranded DNA molecule consisting essentially of a double-stranded foreign DNA encoding RNA which does not naturally occur in an animal into which the recombinant swinepox virus is introduced, with at one end of the foreign DNA, double-stranded swinepox viral DNA homologous to genomic DNA located at one side of a site on the genomic DNA which is not essential for replication of the swinepox virus, and at the other end of the foreign DNA, double-stranded swinepox viral DNA homologous to genomic DNA located at the other side of the same site on the genomic DNA. Preferably, the RNA encodes a polypeptide.

In one embodiment, the polypeptide is antigenic in the animal. Preferably, the antigenic polypeptide is or is from pseudorabies virus (PRV) glycoprotein 50, pseudorabies virus (PRV) glycoprotein II, Pseudorabies virus (PRV) glycoprotein III, Pseudorabies virus (PRV) glycoprotein H, Transmissible gastroenteritis (TGE) glycoprotein 195, Transmissible gastroenteritis (TGE) matrix protein, swine rotavirus glycoprotein 38, swine parvovirus capsid protein, *Serpulina hydodysen-*

*teriae* protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is or is from *Serpulina hyodysenteriae*, Foot and Mouth Disease Virus, Hog Cholera Virus, Swine Influenza Virus, African Swine Fever Virus or *Mycoplasma hyopneumoniae*.

In one embodiment, the polypeptide is a detectable marker. Preferably, the polypeptide which is a detectable marker is *E. coli* ⊖-galactosidase.

In one embodiment of the invention, the double-stranded swinepox viral DNA is homologous to genomic DNA present within the larger HindIII to BglII subfragment of the HindIII M fragment of swinepox virus. Preferably, the double-stranded swinepox viral DNA is homologous to genomic DNA present within the open reading frame contained in this HindIII to BglII subfragment. Preferably, the double-stranded swinepox viral DNA is homologous to genomic DNA present within the AccI restriction endonuclease site located in this HindIII to BglII subfragment.

For purposes of this invention, a "homology vector" is a plasmid constructed to insert foreign DNA in a specific site on the genome of a swinepox virus.

In one embodiment of the invention, the double-stranded swinepox viral DNA in the homology vector is homologous to genomic DNA present within the open reading frame encoding swinepox thymidine kinase.

The invention further provides a homology vector where foreign DNA further comprises a synthetic pox viral promoter.

The invention further provides a vaccine which comprises an effective immunizing amount of a recombinant swinepox virus of the present invention and a suitable carrier.

Suitable carriers for the pseudorabies virus are well known in the art and include proteins, sugars, etc. One example of such a suitable carrier is a physiologically balanced culture medium containing one or more stabilizing agents such as stabilized, hydrolyzed proteins, lactose, etc.

For purposes of this invention, an "effective immunizing amount" of the recombinant swinepox virus of the present invention is within the range of $10^3$ to $10^9$ PFU/dose.

The present invention also provides a method of immunizing an animal, wherein the animal is a swine, bovine, equine, caprine or ovine. For purposes of this invention, this includes immunizing the animal against the virus or viruses which cause the disease or diseases pseudorabies, transmissible gastroenteritis, swine rotavirus, swine parvovirus, *Serpulina hyodysenteriae*, bovine viral diarrhea, Newcastle disease, swine flu, foot and mouth disease, hog cholera, African swine fever or *Mycoplasma hyopneumoniae*. The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a method for testing a swine to determine whether the swine has been vaccinated with the vaccine of the present invention, particularly the embodiment which contains the recombinant swinepox virus S-SPV-008 (ATCC Accession No. VR 2339), or is infected with a naturally-occurring, wild-type pseudorabies virus. This method comprises obtaining from the swine to be tested a sample of a suitable body fluid, detecting in the sample the presence of antibodies to pseudorabies virus, the absence of such antibodies indicating that the swine has been neither vaccinated nor infected, and for the swine in which antibodies to pseudorabies virus are present, detecting in the sample the absence of antibodies to pseudorabies virus antigens which are normally present in the body fluid of a swine infected by the naturally-occurring pseudorabies virus but which are not present in a vaccinated swine indicating that the swine was vaccinated and is not infected.

The present invention also provides a host cell infected with a recombinant swinepox virus capable of replication.

In one embodiment, the host cell is a mammalian cell. Preferably, the mammalian cell is a Vero cell. Preferably, the mammalian cell is an EMSK cell.

For purposes of this invention a "host cell" is a cell used to propagate a vector and its insert. Infecting the cells was accomplished by methods well known to those of skill in the art, for example, as set forth in INFECTION-TRANSFECTION PROCEDURE in Material and Methods.

Methods for constructing, selecting and purifying recombinant swinepox virus, including S-SPV-003, S-SPV-008 and S-SPV-009, are detailed below in Materials and Methods.

Materials and Methods

PREPARATION OF SWINEPOX VIRUS STOCK SAMPLES. Swinepox virus (SPV) samples were prepared by infecting embryonic swine kidney (EMSK) cells at a multiplicity of infection of 0.01 PFU/cell in a 1:1 mixture of Iscove's Modified Dulbecco's Medium (IMDM) and RPMI 1640 medium containing 2 mM glutamine, 100 units/ml penicillin, 100 units/ml streptomycin (these components were obtained from Sigma or equivalent supplier, and hereafter are referred to as EMSK negative medium). Prior to infection, the cell monolayers were washed once with EMSK negative medium to remove traces of fetal bovine serum. The SPV contained in the initial inoculum (0.5 ml for 10 cm plate; 10 ml for T175 cm flask) was then allowed to absorb onto the cell monolayer for two hours, being redistributed every half hour. After this period, the original inoculum was brought up to the recommended volume with the addition of complete EMSK medium (EMSK negative medium plus 5% fetal bovine serum). The plates were incubated at 37° C. in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^6$ PFU/ml.

PREPARATION OF SPV DNA. For swinepox virus DNA isolation, a confluent monolayer of EMSK cells in a T175 cm² flask was infected at a multiplicity of 0.1 and incubated 4–6 days until the cells were showing 100% cytopathic effect. The infected cells were then harvested by scraping the cells into the medium and centrifuging at 3000 rpm for 5 minutes in a clinical centrifuge. The medium was decanted, and the cell pellet was gently resuspended in 1.0 ml Phosphate Buffer Saline (PBS: 1.5g Na$_2$HPO$_4$, 0.2 g KH$_2$PO$_4$, 0.8 g NaCL and 0.2 g KCl per liter H$_2$O) (per T175) and subjected to two successive freeze-thaws (−70° C. to 37° C.). Upon the last thaw, the cells (on ice) were sonicated two times for 30 seconds each with 45 seconds cooling time in between. Cellular debris was then removed by centrifuging (Sorvall RC-5B superspeed centrifuge) at 3000 rpm for 5 minutes in a HB4 rotor at 4° C. SPV virions, present in the supernatant, were then pelleted by centrifugation at 15,000 rpm for 20 minutes at 4° C. in a SS34 rotor (Sorvall) and resuspended in 10 mM Tris (pH 7.5). This fraction was then layered onto a 36% sucrose gradient (w/v in 10 mM tris pH 7.5) and centrifuged (Beckman L8-70M Ultracentrifuge) at 18,000 rpm for 60 minutes in a SW41 rotor (Beckman) at 4° C. The virion pellet was resuspended in 1.0 ml of 10 mM tris pH 7.5 and sonicated on ice for 30 seconds. This fraction was layered onto a 20% to 50% continuous sucrose gradient and centrifuged 16,000 rpm for 60 minutes in a SW41 rotor at 4° C. The SPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. SPV DNA was then extracted from the purified virions by lysis (4 hours at 60° C.) induced by the addition of EDTA, SDS, and proteinase K to final concentrations of 20 mM, 0.5% and 0.5 mg/ml, respectively. After digestion, three phenol:chloroform (1:1) extractions were conducted and the sample precipitated by the addition of two volumes of absolute ethanol and incubation at −20° C. for 30 minutes. The sample was then centrifuged in an Eppendorf minifuge for 5 minutes at full speed. The supernatant was decanted, and the pellet air dried and rehydrated in 0.01 M Tris pH 7.5, 1 mM EDTA at 4° C.

PREPARATION OF INFECTED CELL LYSATES. For cell lysate preparation, serum free medium was used. A confluent monolayer of cells (EMSK for SPV or VERO for PRV) in a 25 cm$^2$ flask or a 60 mm petri dish was infected with 100 μl of virus sample. After cytopathic effect was complete, the medium and cells were harvested and the cells were pelleted at 3000 rpm for 5 minutes in a clinical centrifuge. The cell pellet was resuspended in 250 μl of disruption buffer (2% sodium dodecyl sulfate, 2% β-mercapto-ethanol). The samples were sonicated for 30 seconds on ice and stored at −20° C.

WESTERN BLOTTING PROCEDURE. Samples of lysates and protein standards were run on a polyacrylamide gel according to the procedure of Laemnli (1970). After gel electrophoresis the proteins were transferred and processed according to Sambrook et al. (1982). The primary antibody was a swine anti-PRV serum (Shope strain; lot370, PDV8201, NVSL, Ames, IA) diluted 1:100 with 5% non-fat dry milk in Tris-sodium chloride, and sodium Azide (TSA: 6.61g Tris-HCl, 0.97g Tris-base, 9.0 g NaCl and 2.0 g Sodium Azide per liter H2O). The secondary antibody was a goat anti-swine alkaline phosphatase conjugate diluted 1:1000 with TSA.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al. (1982) and Sambrook et al. (1989). Except as noted, these were used with minor variation.

DNA SEQUENCING. Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone TM and Supersee TM programs from Coral Software.

CLONING WITH THE POLYMERASE CHAIN REACTION. The polymerase chain reaction (PCR) was used to introduce restriction sites convenient for the manipulation of various DNAs. The procedures used are described by Innis, et al. (1990). In general, amplified fragments were less than 500 base pairs in size and critical regions of amplified fragments were confirmed by DNA sequencing. The primers used in each case are detailed in the descriptions of the construction of homology vectors below.

Figure 5B:
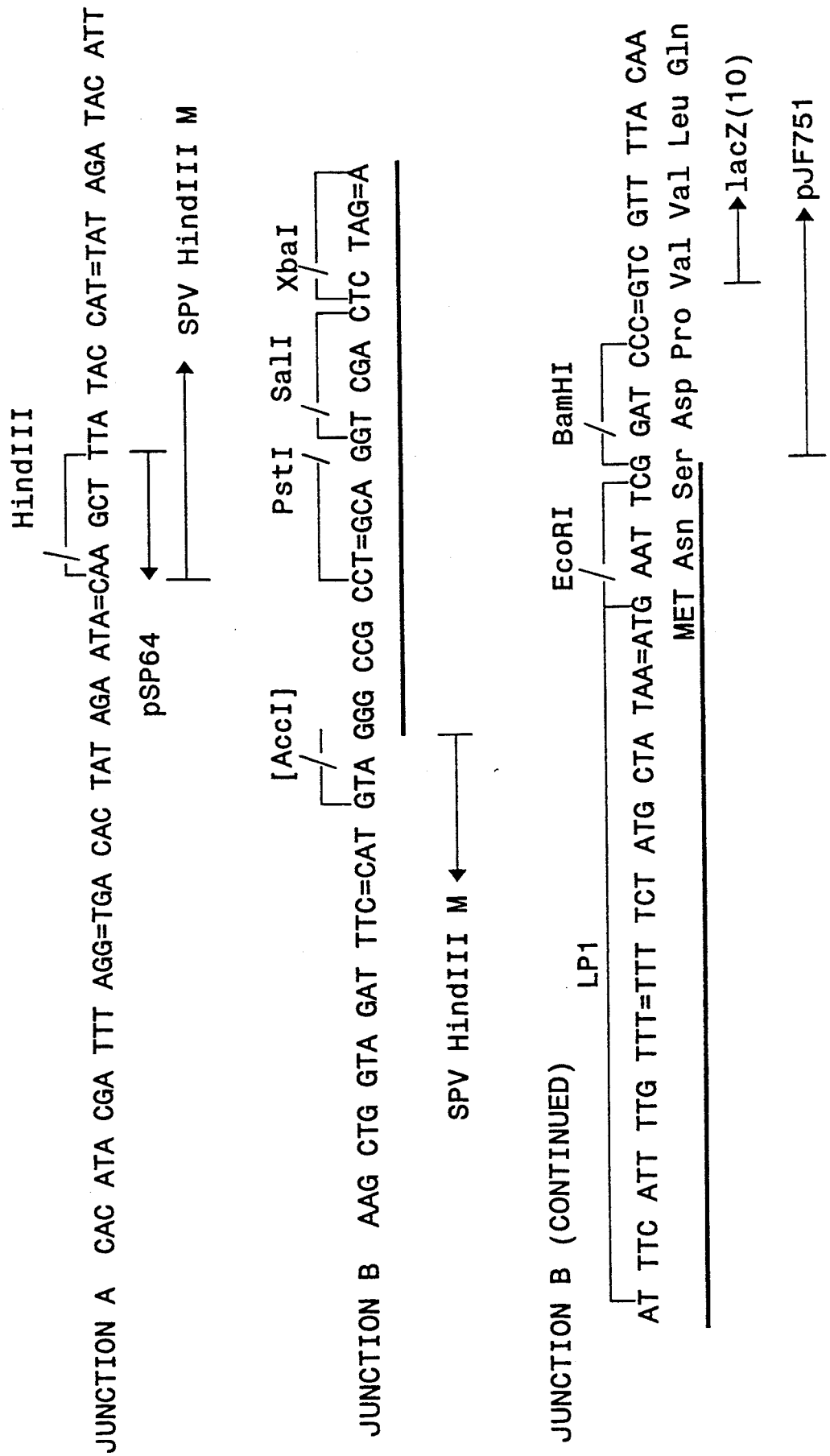
FIG. 5 (5A, 5B, 5C and 5D) Detailed description of the DNA insertion in Homology Vector 538-46.16. Diagram showing the orientation of DNA fragments assembled in plasmid 538-46.16. The origin of each fragment is indicated in the table. The sequences located at each of the junctions between fragments are also shown (SEQ ID NO's: 17, 18, 21, 26, and 28). The restriction sites used to generate each fragment as well as the synthetic linker sequences which were used to join the fragments are described for each junction. The synthetic linker sequences are underlined by a heavy bar. The location of several gene coding regions and regulatory elements is also given. The following two conventions are used: numbers in parenthesis () refer to amino acids, and restriction sites in brackets []indicate the remnants of sites which were destroyed during construction. The following abbreviations are used, swinepox virus (SPV), pseudorabies virus (PRV), glycoprotein 50 (gp50), glycoprotein 63 (gp63), early promoter 1 (EP1), late promoter 1 (LP1), late promoter 2 (LP2), lactose operon Z gene (lacZ), and *Escherichia coli* (*E. coli*).
Figure 5C:
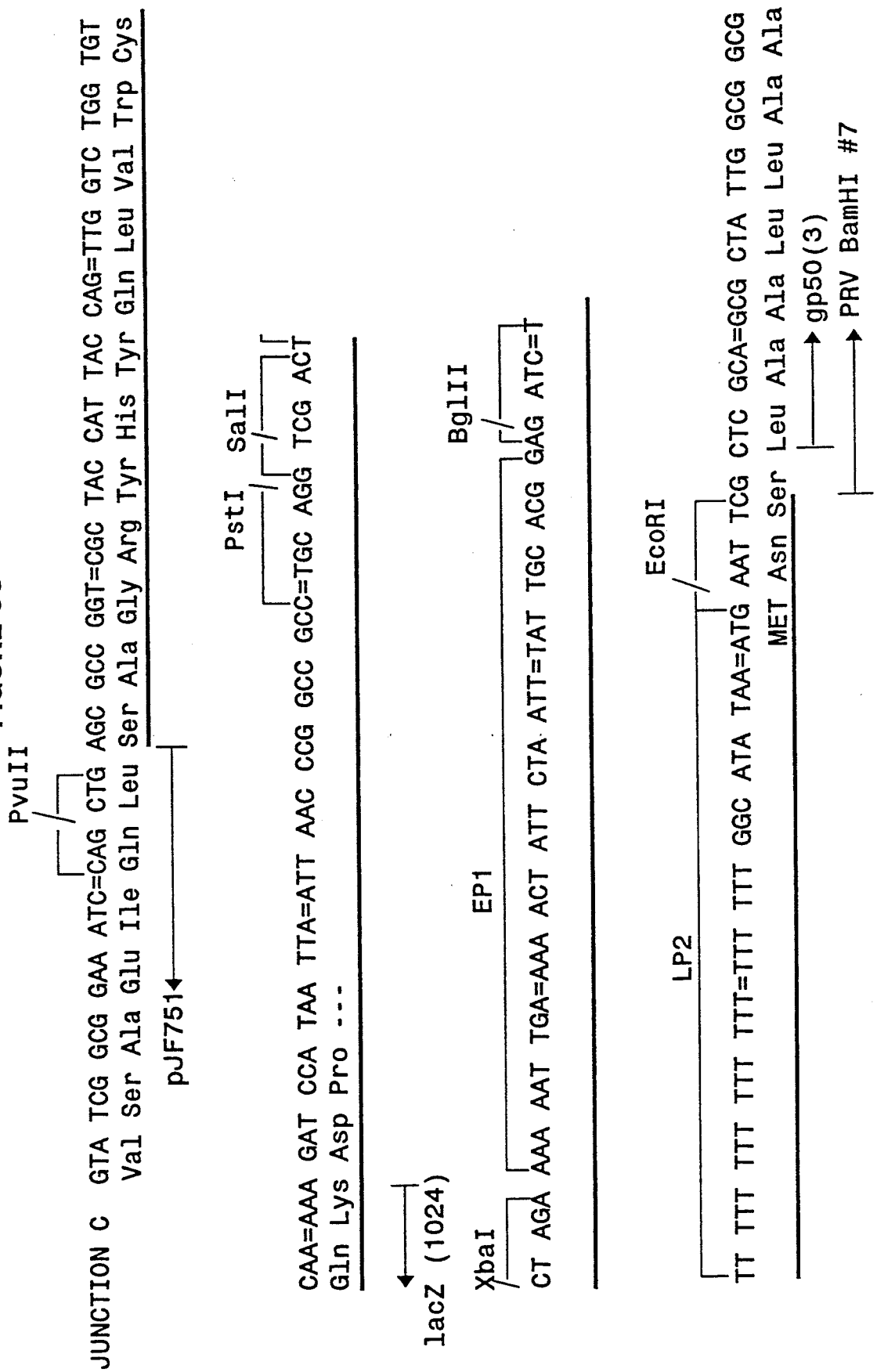
Figure 5D:
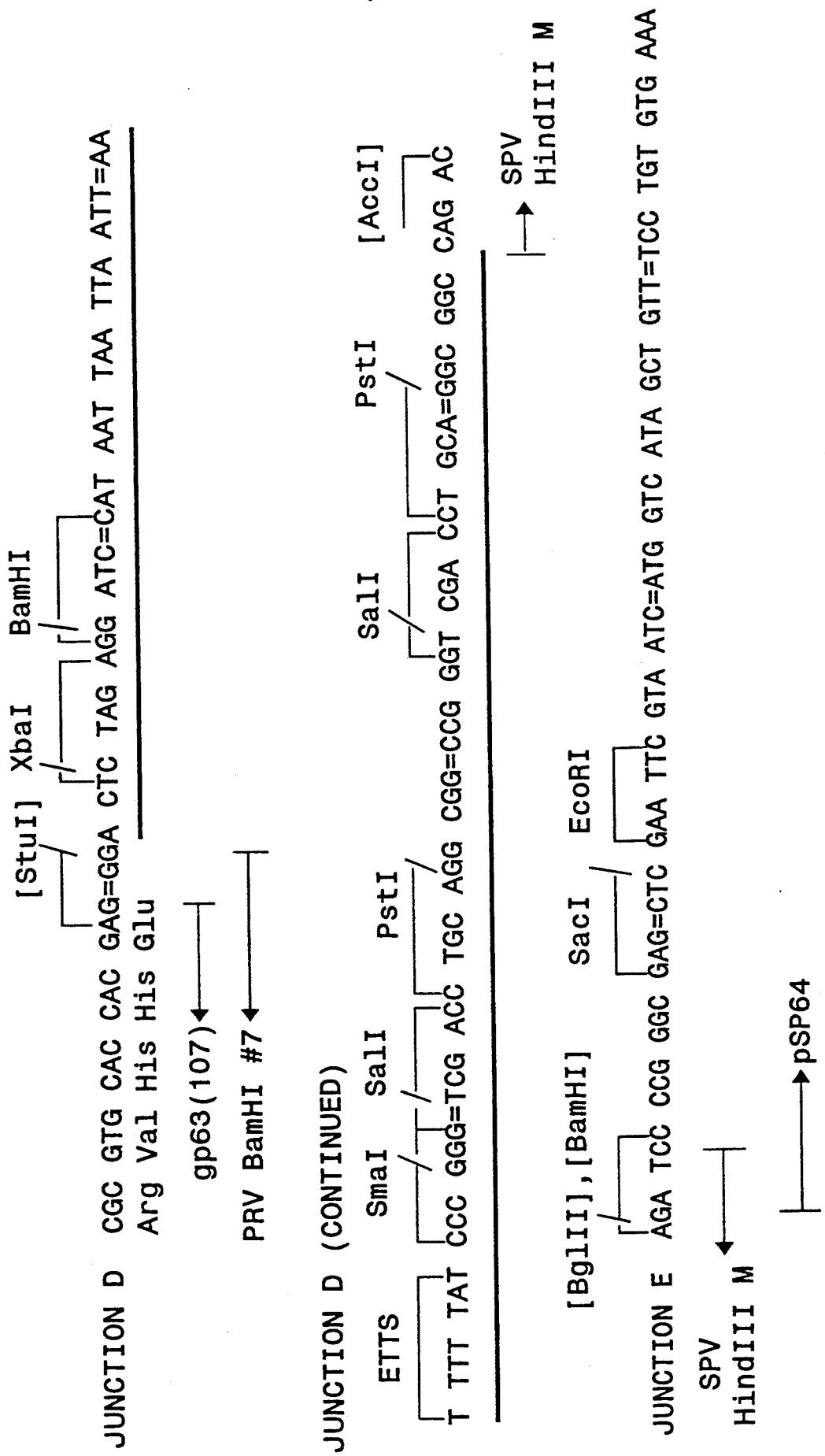

HOMOLOGOUS RECOMBINATION PROCEDURE FOR GENERATING RECOMBINANT SPV. This method relies upon the homologous recombination between the swinepox virus DNA and the plasmid homology vector DNA which occurs in the tissue culture cells containing both swinepox virus DNA and transfected plasmid homology vector. For homologous recombination to occur, the monolayers of EMSK cells are infected with S-SPV-001 (Kasza SPV strain, 17) at a multiplicity of infection of 0.01PFU/cell to introduce replicating SPV (i.e. DNA synthesis) into the cells. The plasmid homology vector DNA is then transfected into these cells according to the INFECTION-TRANSFECTION PROCEDURE. The construction of homology vectors used in this procedure is described below INFECTION-TRANSFECTION PROCEDURE. 6 cm plates of EMSK cells (about 80% confluent) were infected with S-SPV-001 at a multiplicity of infection of 0.01 PFU/cell in EMSK negative medium and incubated at 37° C. in a humidified 5% CO$_2$ environment for 5 hours. The transfection procedure used is essentially that recommended for Lipofectin TM  Reagent (BRL). Briefly, for each 6 cm plate, 15 μg of plasmid DNA was diluted up to 100 μl with H$_2$O. Separately, 50 micrograms of Lipofectin Reagent was diluted to 100 μl with H$_2$0. The 100 μl of diluted Lipofectin Reagent was then added dropwise to the diluted plasmid DNA contained in a polystyrene 5 ml snap cap tube and mixed gently. The mixture was then incubated for 15–20 minutes at room temperature. During this time, the virus inoculum was removed from the 6 cm plates and the cell monolayers washed once with EMSK negative medium. Three ml of EMSK negative medium was then added to the plasmid DNA/lipofectin mixture and the contents pipetted onto the cell monolayer. The cells were incubated overnight (about 16 hours) at 37° C. in a humidified 5% CO$_2$ medium was removed and replaced with 5 ml EMSK complete medium. The cells were incubated at 37° C. in 5% $CO_2$ for 3–7 days until cytopathic effect from the virus was 80–100%. Virus was harvested as described above for the preparation of virus stocks. This stock was referred to as a transfection stock and was subsequently screened for recombinant virus by the BLUOGAL SCREEN FOR RECOMBINANT SWINEPOX VIRUS OR CPRG SCREEN FOR RECOMBINANT SWINEPOX VIRUS.

SCREEN FOR RECOMBINANT SPV EXPRESSING β-GALACTOSIDASE (BLUOGAL AND CPRG ASSAYS). When the *E. coli* β-galactosidase (lacZ) marker gene was incorporated into a recombinant virus the plaques containing the recombinants were visualized by one of two simple methods. In the first method, the chemical Bluogal™ (Bethesda Research Labs) was incorporated (200 μg/ml) into the agarose overlay during the plaque assay, and plaques expressing active β-galactosidase turned blue. The blue plaques were then picked onto fresh cells (EMSK) and purified by further blue plaque isolation. In the second method, CPRG (Boehringer Mannheim) was incorporated (400 μg/ml) into the agarose overlay during the plaque assay, and plaques expressing active β-galactosidase turned red. The red plaques were then picked onto fresh cells (EMSK) and purified by further red plaque isolation. In both cases viruses were typically purified with three rounds of plaque purification.

SCREEN FOR FOREIGN GENE EXPRESSION IN RECOMBINANT SPV USING BLACK PLAQUE ASSAYS. To analyze expression of foreign antigens expressed by recombinant swinepox viruses, monolayers of EMSK cells were infected with recombinant SPV, overlayed with nutrient agarose media and incubated for 6–7 days at 37° C. for plaque development to occur. The agarose overlay was then removed from the dish, the cells fixed with 100% methanol for 10 minutes at room temperature and the cells air dried. Fixation of the cells results in cytoplasmic antigen as well as surface antigen detection whereas specific surface antigen expression can be detected using non-fixed cells. The primary antibody was then diluted to the appropriate dilution with PBS and incubated on the cell monolayer for 2 hours at room temperature. To detect PRV gp50 expression from S-SPV-008, swine anti-PRV serum (Shope strain; lot370, PDV8201, NVSL, Ames, IA) was used (diluted 1:100). To detect NDV HN expression from S-SPV-009, a rabbit antiserum specific for the HN protein (rabbit anti-NDV#2) was used (diluted 1:1000). Unbound antibody was then removed by washing the cells three times with PBS at room temperature. The secondary antibody, either a goat anti-swine (PRVgp50; S-SPV-008) or goat anti-rabbit (NDV PIN; S-SPV-009), horseradish peroxidase conjugate was diluted 1:250 with PBS and incubated with the cells for 2 hours at room temperature. Unbound secondary antibody was then removed by washing the cells three times with PBS at room temperature. The cells were then incubated 15–30 minutes at room temperature with freshly prepared substrate solution (100 μg/ml 4-chloro-1-naphthol, 0,003% $H_2O_2$ in PBS). Plaques expressing the correct antigen stain black. STRATEGY FOR THE CONSTRUCTION OF SYNTHETIC POX VIRAL PROMOTERS. For recombinant swinepox vectors synthetic pox promoters offer several advantages including the ability to control the strength and timing of foreign gene expression. We chose to design three promoter cassettes LP1, EP1 and LP2 based on promoters that have been defined in the vaccinia virus (1, 7 and 8). Each cassette was designed to contain the DNA sequences defined in vaccinia flanked by restriction sites which could be used to combine the cassettes in any order or combination. Initiator methionines were also designed into each cassette such that inframe fusions could be made at either EcoRI or BamHI sites. A set of translational stop codons in all three reading frames and an early transcriptional termination signal (9) were also engineered downstream of the inframe fusion site. DNA encoding each cassette was synthesized according to standard techniques and cloned into the appropriate homology vectors (see FIGS. 4, 5 and 8).

HOMOLOGY VECTOR 515-85.1. The plasmid 515-85.1 was constructed for the purpose of inserting foreign DNA into SPV. It contains a unique AccI restriction enzyme site into which foreign DNA may be inserted. When a plasmid, containing a foreign DNA insert at the AccI site, is used according to the HOMOLOGOUS RECOMBINATION PROCEDURE FOR GENERATING RECOMBINANT SPV a virus containing the foreign DNA will result. A restriction map of the DNA insert in homology vector 515-85.1 is given in FIG. 4. It may be constructed utilizing standard recombinant DNA techniques (22 and 29), by Joining two restriction fragments from the following sources. The first fragment is an approximately 2972 base pair HindIII to BamHI restriction fragment of pSP64 (Promega). The second fragment is an approximately 3300 base pair HindIII to BglII restriction subfragment of the SPV HindIII restriction fragment M (23) . HOMOLOGY VECTOR 520-17.5. The plasmid 520-17.5 was constructed for the purpose of inserting foreign DNA into SPV. It incorporates an *E. coli* β-galactosidase (lacZ) marker gene flanked by SPV DNA. Upstream of the marker gene is an approximately 2015 base pair fragment of SPV DNA. Downstream of the marker gene is an approximately 1103 base pair fragment of SPV DNA. When this plasmid is used according to the HOMOLOGOUS RECOMBINATION PROCEDURE FOR GENERATING RECOMBINANT SPV a virus containing DNA coding for the marker gene will result. Note that the β-galactosidase (lacZ) marker gene is under the control of a synthetic early/late pox promoter. A detailed description of the plasmid is given in FIG. 4. It may be constructed utilizing standard recombinant DNA techniques (22 and 30), by joining restriction fragments from the following sources with the synthetic DNA sequences indicated in FIG. 4. The plasmid vector is derived from an approximately 2972 base pair HindIII to BamHI restriction fragment of pSP64 (Promega). Fragment 1 is an approximately 2015 base pair HindIII to AccI restriction subfragment of the SPV HindIII restriction fragment M (23). Fragment 2 is an approximately 3010 base pair BamHI to PvuII restriction fragment of plasmid pJF751 (11). Fragment 3 is an approximately 1103 base pair AccI to BglII restriction sub-fragment of the SPV HindIII fragment M (23).

HOMOLOGY VECTOR 538-46.16. The plasmid 538-46.16 was constructed for the purpose of inserting foreign DNA into SPV. It incorporates an *E. coli* β-galactosidase (lacZ) marker gene and the PRV gp50 gene flanked by SPV DNA. Upstream of the foreign genes is an approximately 2015 base pair fragment of SPV DNA. Downstream of the foreign genes is an approximately 1103 base pair fragment of SPV DNA. When this plasmid is used according to the HOMOLO- GOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter and the gp50 gene is under the control of a synthetic early/late pox promoter. A detailed description of the plasmid is given in FIG. 5. It may be constructed utilizing standard recombinant DNA techniques (22 and 30), by joining restriction fragments from the following sources with the synthetic DNA sequences indicated in FIG. 5. The plasmid vector is derived from an approximately 2972 base pair HindIII to BamHI restriction fragment of pSP64 (Promega). Fragment 1 is an approximately 2015 base pair HindIII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 1571 base pair EcoRI to StuI restriction sub-fragment of the PRV BamHI fragment 7 (21). Note that the EcoRI site was introduced in to this fragment by PCR cloning. In this procedure the primers described below were used along with a template consisting of a PRV BamHI #7 fragment subcloned into pSP64. The first primer 87.03 (5'-CGCGAATTCGCTCGCAGCGCTATTGGC-3') (SEQ ID No:41) sits down on the PRV gp50 sequence (26) at approximately amino acid 3 priming toward the 3' end of the gene. The second primer 87.06 (5'-GTAGGAGTGGCTGCTGAAG-3') (SEQ ID NO:42) sits down on the opposite strand at approximately amino acid 174 priming toward the 5' end of the gene. The PCR product may be digested with EcoRI and SalI to produce an approximately 509 base pair fragment. The approximately 1049 base pair SalI to StuI sub-fragment of PRV BamHI #7 may then be ligated to the approximately 509 base pair EcoRI to SalI fragment to generate the approximately 1558 base pair EcoRI to StuI fragment 3. Fragment 4 is an approximately 1103 base pair AccI to BglII restriction sub-fragment of the SPV HindIII fragment M (23).

HOMOLOGY VECTOR 538-46.26. The plasmid 538-46.26 was constructed for the purpose of inserting foreign DNA into SPV. It incorporates an E.coli β-galactosidase (lacZ) marker gene and the Newcastle Disease Virus (NDV) hemagglutinin-Neuraminidase (PIN) gene flanked by SPV DNA. Upstream of the foreign genes is an approximately 2015 base pair fragment of SPV DNA. Downstream of the foreign genes is an approximately 1103 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter and the HN gene is under the control of a synthetic early/late pox promoter. A detailed description of the plasmid is given in FIG. 8. It may be constructed utilizing standard recombinant DNA techniques (22 and 30), by joining restriction fragments from the following sources with the synthetic DNA sequences indicated in FIG. 8. The plasmid vector is derived from an approximately 2972 base pair HindIII to BamHI restriction fragment of pSP64 (Promega). Fragment 1 is an approximately 2015 base pair HindIII to AccI restriction sub-fragment of the SPV HindIII restriction fragment M (23). Fragment 2 is an approximately 1810 base pair AvaII to NaeI restriction fragment of a NDV HN cDNA clone. The sequence of the HN cDNA clone is given in FIG. 7. The cDNA clone was generated from the B1 strain of NDV using standard cDNA cloning techniques (14). Fragment 3 is an approximately 3010 base pair BamHI to PvuII restriction fragment of plasmid pJF751 (11). Fragment 4 is an approximately 1103 base pair AccI to BglII restriction sub-fragment of the SPV HindIII fragment M (23).

HOMOLOGY VECTOR 520-90.15. The plasmid 520-90.15 was constructed for the purpose of inserting foreign DNA into SPV. It contains a unique NdeI restriction enzyme site into which foreign DNA may be inserted. When a plasmid, containing a foreign DNA insert at the NdeI site, is used according to the HOMOLOGOUS RECOMBINATION PROCEDURE FOR GENERATING RECOMBINANT SPV a virus containing the foreign DNA will result. Plasmid 520-90.15 was constructed utilizing standard recombinant DNA techniques (22 and 30), by joining two restriction fragments from the following sources. The first fragment is an approximately 2972 base pair HindIII to BamHI restriction fragment of pSP64 (Promega). The second fragment is an approximately 1700 base pair HindIII to BamHI restriction subfragment of the SPV HindIII restriction fragment G (23).

EXAMPLES

Example 1

Homology Vector 515-85.1

The homology vector 515-85.1 is a plasmid useful for the insertion of foreign DNA into SPV. Plasmid 515-85.1 contains a unique AccI restriction site into which foreign DNA may be cloned. A plasmid containing such a foreign DNA insert may be used according to the HOMOLOGOUS RECOMBINATION PROCEDURE FOR GENERATING RECOMBINANT SPV to generate a SPV containing the foreign DNA. For this procedure to be successful it is important that the insertion site (AccI) be in a region non-essential to the replication of the SPV and that the site be flanked with swinepox virus DNA appropriate for mediating homologous recombination between virus and plasmid DNAs. We have demonstrated that the AccI site in homology vector 515-85.1 may be used to insert foreign DNA into at least three recombinant SPV (see examples 2-4).

In order to define an appropriate insertion site, a library of SPV HindIII restriction fragments was generated. Several of these restriction fragments (HindIII fragments G, J, and M see FIG. 1) were subjected to restriction mapping analysis. Two restriction sites were identified in each fragment as potential insertion sites. These sites included HpaI and NruI in fragment G, BalI and XbaI in fragment J, and AccI and PstI in fragment M. A β-galactosidase (lacZ) marker gene was inserted in each of the potential sites. The resulting plasmids were utilized in the HOMOLOGOUS RECOMBINATION PROCEDURE FOR GENERATING RECOMBINANT SPV. The generation of recombinant virus was determined by the SCREEN FOR RECOMBINANT SPV EXPRESSING β-GALACTOSIDASE ASSAYS. Four of the six sites were found to generate recombinant virus, however the ability of each of these viruses to be purified away from the parental SPV varied greatly. In one case virus could not be purified above the level of 1%, in another case virus could not be purified above the level of 50%, and in a third case virus could not be purified above the level of 90%. The inability to purify these viruses indicates instability at the insertion site. This makes the corresponding sites inappropriate for insertion of foreign DNA. However the insertion at one site, the AccI site of Homology vector 515-85.1, resulted in a virus which was easily purified to 100% (see example 2), clearly defining an appropriate site for the insertion of foreign DNA.

Figure 3A:
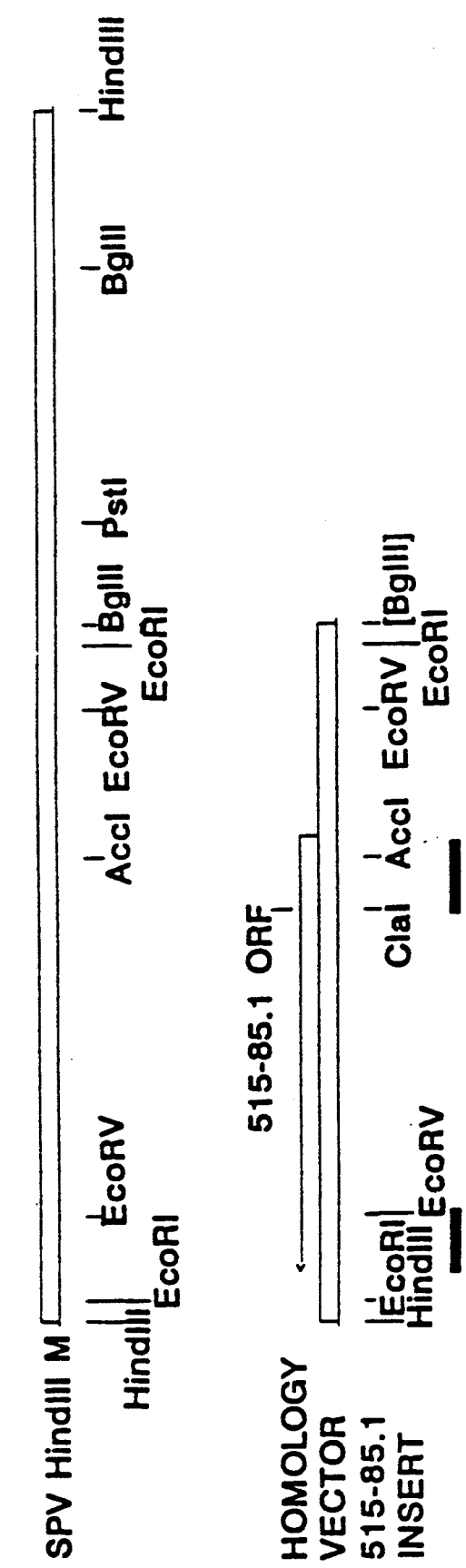
FIG. 3 (3A, 3B and 3C) Homology between the 515.85,1 ORF and the Vaccinia virus 01L ORF. The first line shows a restriction map of the SPV HindIII M fragment. The second map shows a restriction map of the DNA insertion in plasmid 515-85.1. The location of the 515-85.1 [VV 01L-like] ORF is indicated on the map, The locations of the DNA sequences shown in FIG. 2 are indicated below the map by heavy bars, The third line shows the homology between the VV 01L ORF (SEQ ID NO:5) and the 515-85.1 ORF (SEQ ID NO:6) at their respective N-termini. The fourth line shows the homology between the VV 01L ORF (SEQ ID NO:7) and the 515-85.1 ORF (SEQ ID NO:8) at their respective C-termini.
Figure 4A:
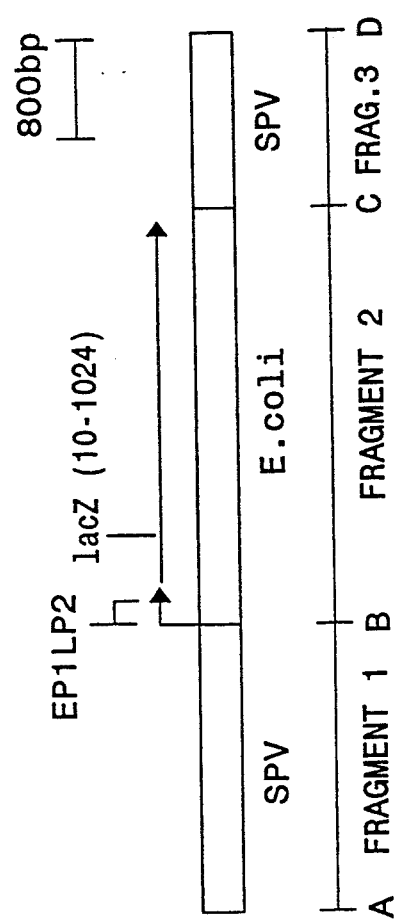
FIG. 4 (4A, 4B and 4C) Detailed description of the DNA insertion in Homology Vector 520-17.5. Diagram showing the orientation of DNA fragments assembled in plasmid 520-17.5. The origin of each fragment is indicated in the table. The sequences located at each of the junctions between fragments is also shown (SEQ ID NO's: 9, 10, 13, and 16). The restriction sites used to generate each fragment as well as the synthetic linker sequences which were used to join the fragments are described for each junction. The synthetic linker sequences are underlined by a heavy bar. The location of several gene coding regions and regulatory elements are also given. The following two conventions are used: numbers in parenthesis () refer to amino acids, and restriction sites in brackets []indicate the remnants of sites which were destroyed during construction. The following abbreviations are used, swinepox virus (SPV), early promoter 1 (EP1), late promoter 2 (LP2), lactose operon Z gene (lacZ), and *Escherichia coli* (*E. coli*).
Figure 4B:
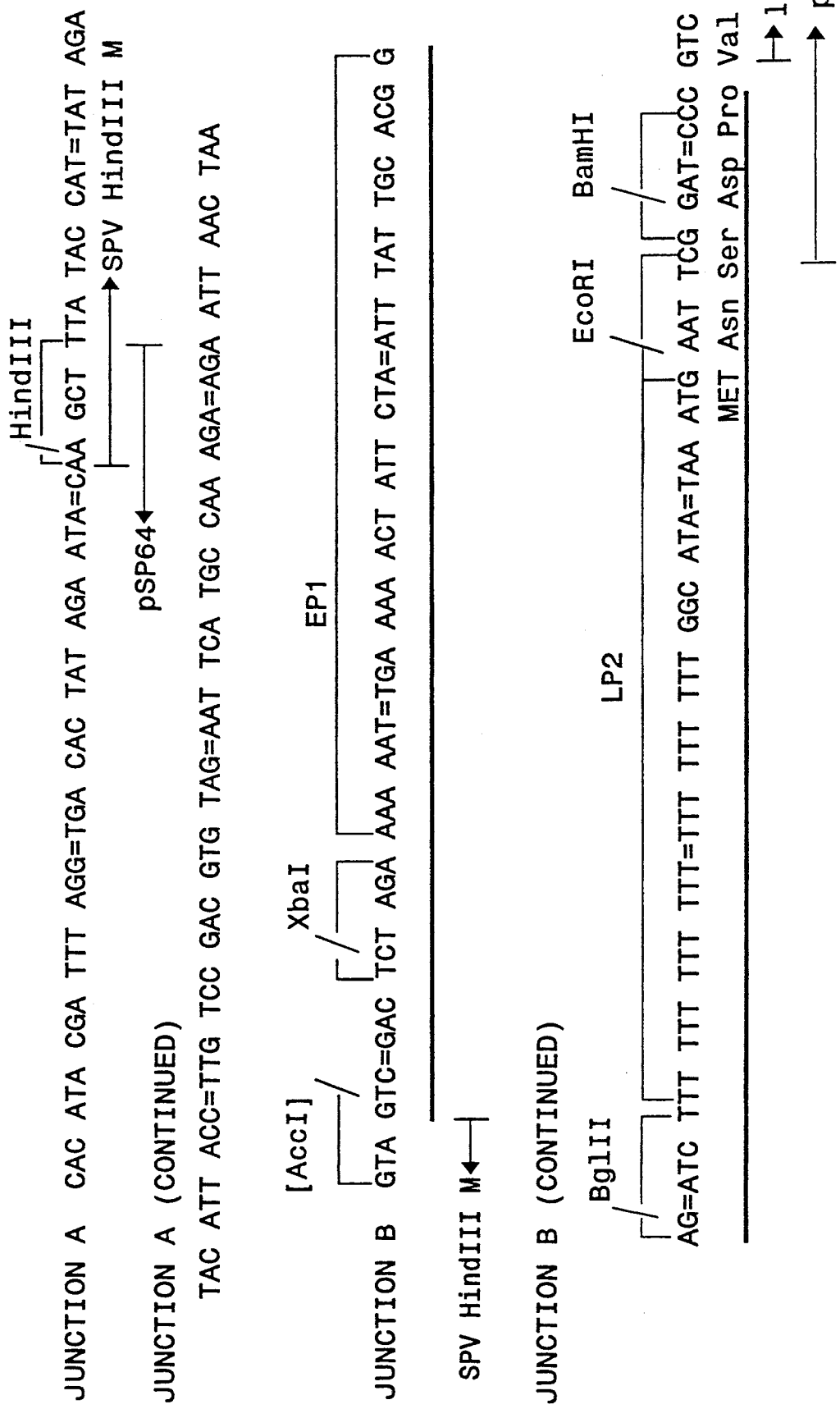
Figure 4C:
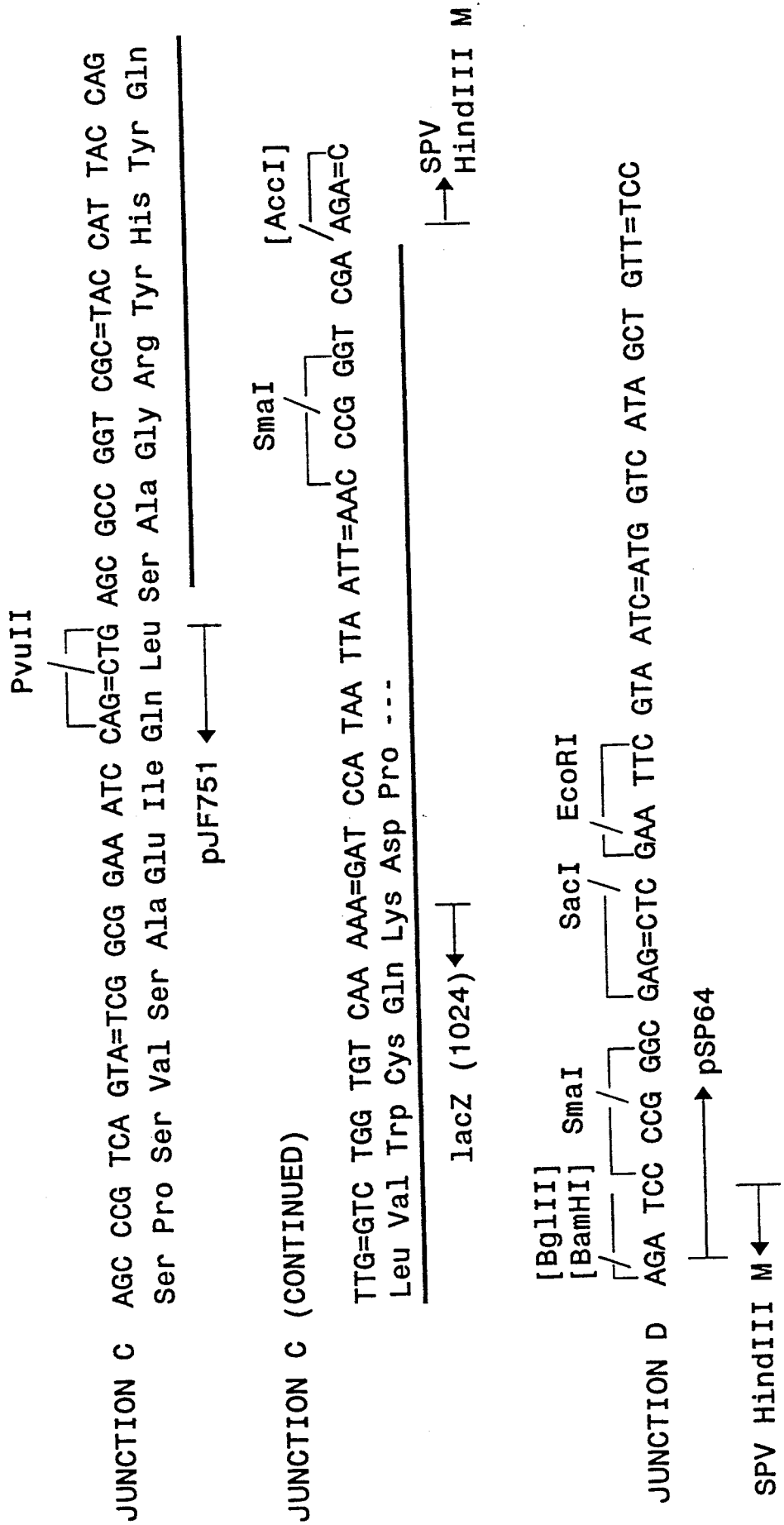

The homology vector 515-85.1 was further characterized by DNA sequence analysis. Two regions of the homology vector were sequenced. The first region covers a 599 base pair sequence which flanks the unique AccI site (see FIG. 2). The second region covers the 899 base pairs upstream of the unique HindIII site (see FIG. 2). The sequence of the first region codes for an open reading frame (ORF) which shows homology to amino acids 1 to 115 of the vaccinia virus (VV) O1L open reading frame identified by Goebel et al, 1990 (see FIG. 3). The sequence of the second region codes for an open reading frame which shows homology to amino acids 568 to 666 of the same vaccinia virus O1L open reading frame (see FIG. 3). These data suggest that the AccI site interrupts the presumptive O 1 L-like ORF at approximately amino acid 41, suggesting that this ORF codes for a gene non-essential for SPV replication. Goebel et al. suggest that the VV O1L ORF contains a leucine zipper motif characteristic of certain eukaryotic transcriptional regulatory proteins, however they indicate that it is not known whether this gene is essential for virus replication.

The DNA sequence located upstream of the VV O1L-like ORF (see FIG. 2A) would be expected to contain a swinepox viral promoter. This swinepox viral promoter will be useful as the control element of foreign DNA introduced into the swinepox genome.

Example 2

S-SPV-003

S-SPV-003 is a swinepox virus that expresses a foreign gene. The gene for *E.coli* β-galactosidase (lacZ gene) was inserted into the SPV 515-85.1 ORF. The foreign gene (lacZ) is under the control of a synthetic early/late promoter (EP1LP2).

S-SPV-003 was derived from S-SPV-001 (Kasza strain). This was accomplished utilizing the homology vector 520-17.5 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-003. This virus was assayed for β-galactosidase expression, purity, and insert stability by multiple passages monitored by the blue plague assay as described in Materials and Methods. After the initial three rounds of purification, all plaques observed were blue indicating that the virus was pure, stable and expressing the foreign gene. The assays described here were carried out in VERO cells as well as EMSK cells, indicating that VERO cells would be a suitable substrate for the production of SPV recombinant vaccines. S-SPV-003 has been deposited with the ATCC under Accession No. VR 2335.

EXAMPLE 3

SPV-008

S-SPV-008 is a swinepox virus that expresses at least two foreign genes. The gene for *E. coli* β-galactosidase (lacZ gene) and the gene for pseudorabies virus (PRV) gp50 (26) were inserted into the SPV 515-85.1 ORF. The lacZ gene is under the control of a synthetic late promoter (LP1) and the gp50 gene is under the control of a synthetic early/late promoter (EP1LP2).

S-SPV-008 was derived from S-SPV-001 (Kasza strain). This was accomplished utilizing the homology vector 538-46.16 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-008. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the marker gene.

S-SPV-008 was assayed for expression of PRV specific antigens using the BLACK PLAQUE SCREEN FOR FOREIGN GENE EXPRESSION IN RECOMBINANT SPV. Swine anti-PRV serum was shown to react specifically with S-SPV-008 plaques and not with S-SPV-009 negative control plaques. All S-SPV-008 observed plaques reacted with the swine antiserum indicating that the virus was stably expressing the PRV foreign gene. The black plaque assay was also performed on unfixed monolayers. The SPV plaques on the unfixed monolayers also exhibited specific reactivity with swine anti-PRV serum indicating that the PRV antigen is expressed on the infected cell surface.

Figure 6:
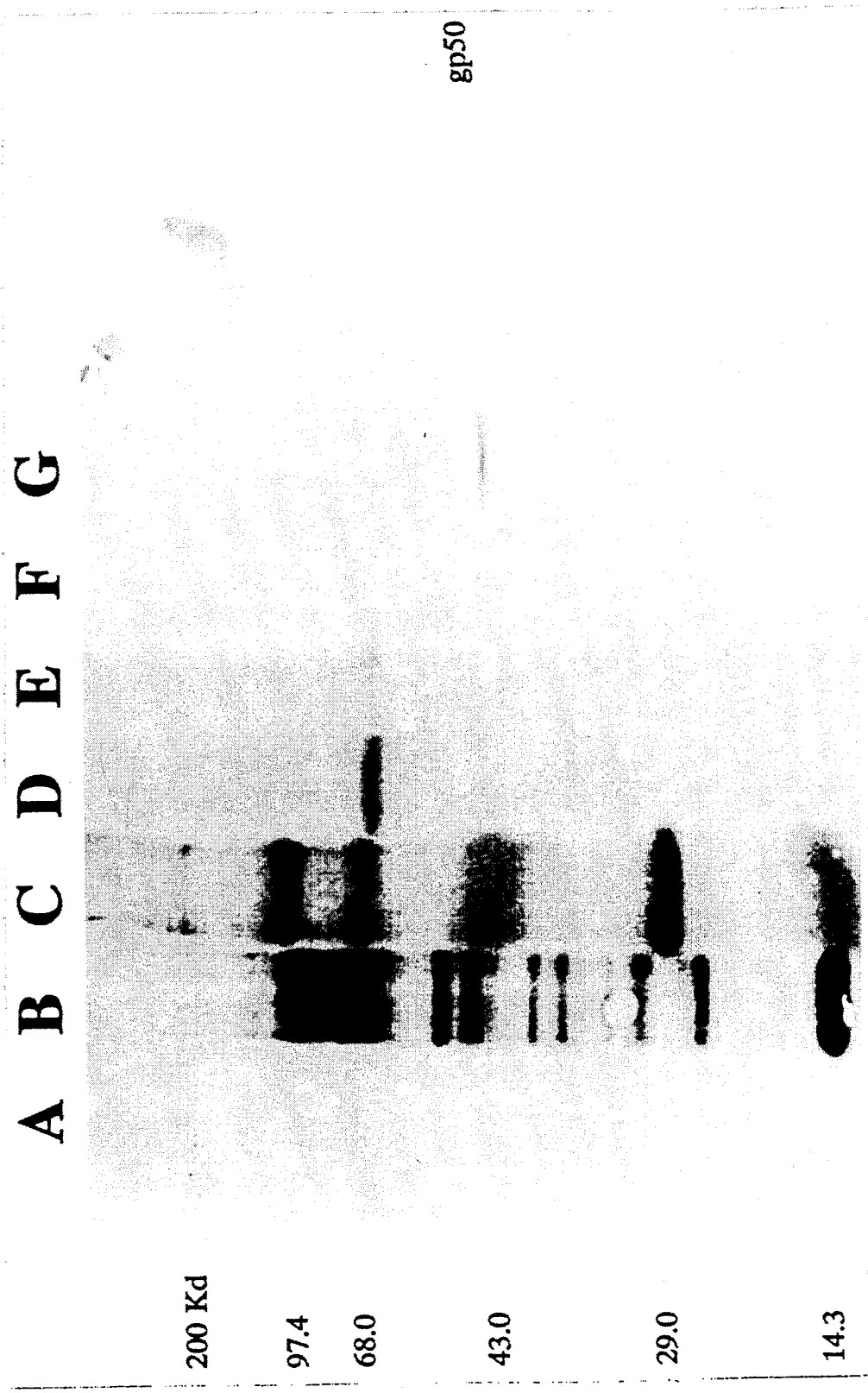
FIG. 6 Western blot of lysates from recombinant SPV infected cells with anti-serum to PRV. Lanes (A) uninfected Vero cell lysate, (B) S-PRV-000 (pseudorabies virus Cooper strain) infected cell lysate, (C) prestained molecular weight markers, (D) uninfected EMSK cell lysate, (E) S-SPV-000 infected cell lysate, (F) S-SPV-003 infected cell lysate, (G) S-SPV-008 infected cell lysate. Cell lysates were prepared as described in the PREPARATION OF INFECTED CELL LYSATES. Approximately 1/5 of the total lysate sample was loaded in each lane.
Figure 8A:
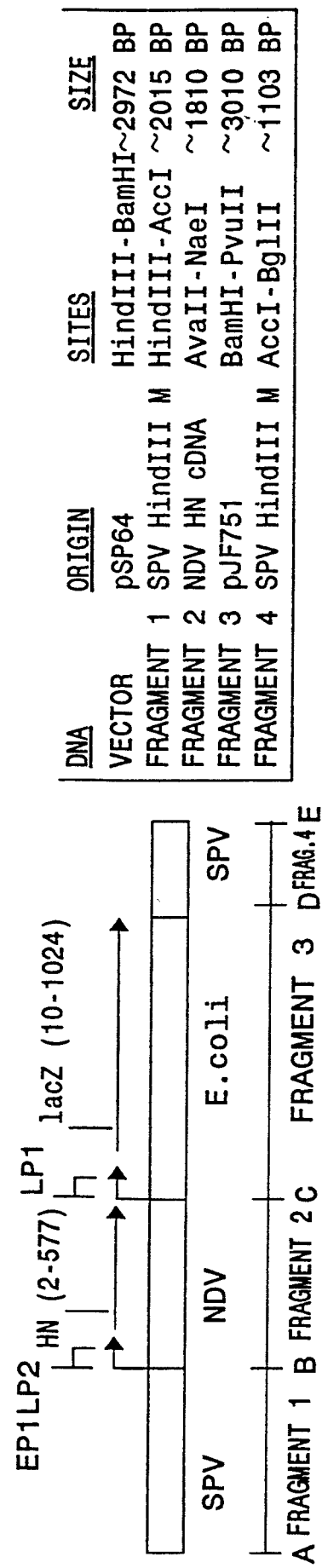
FIG. 8 (8A, 8B, 8C and 8D) Detailed description of the DNA insertion in Homology Vector 538-46.26. Diagram showing the orientation of DNA fragments assembled in plasmid 538-46.26. The origin of each fragment is indicated in the table. The sequences located at each of the junctions between fragments is also shown (SEQ ID NO's: 31, 32, 34, 37, and 40). The restriction sites used to generate each fragment as well as the synthetic linker sequences which were used to join the fragments are described for each junction. The synthetic linker sequences are underlined by a heavy bar. The location of several gene coding regions and regulatory elements is also given. The following two conventions are used: numbers in parenthesis () refer to amino acids, and restriction sites in brackets []indicate the remnants of sites which were destroyed during construction. The following abbreviations are used, swinepox virus (SPV), Newcastle Disease virus (NDV), hemagglutinin-neuraminidase (HN), early promoter 1 (EP1), late promoter 1 (LP1), late promoter 2 (LP2), lactose operon Z gene (lacZ), and *Escherichia coli* (*E. coli*).
Figure 8B:
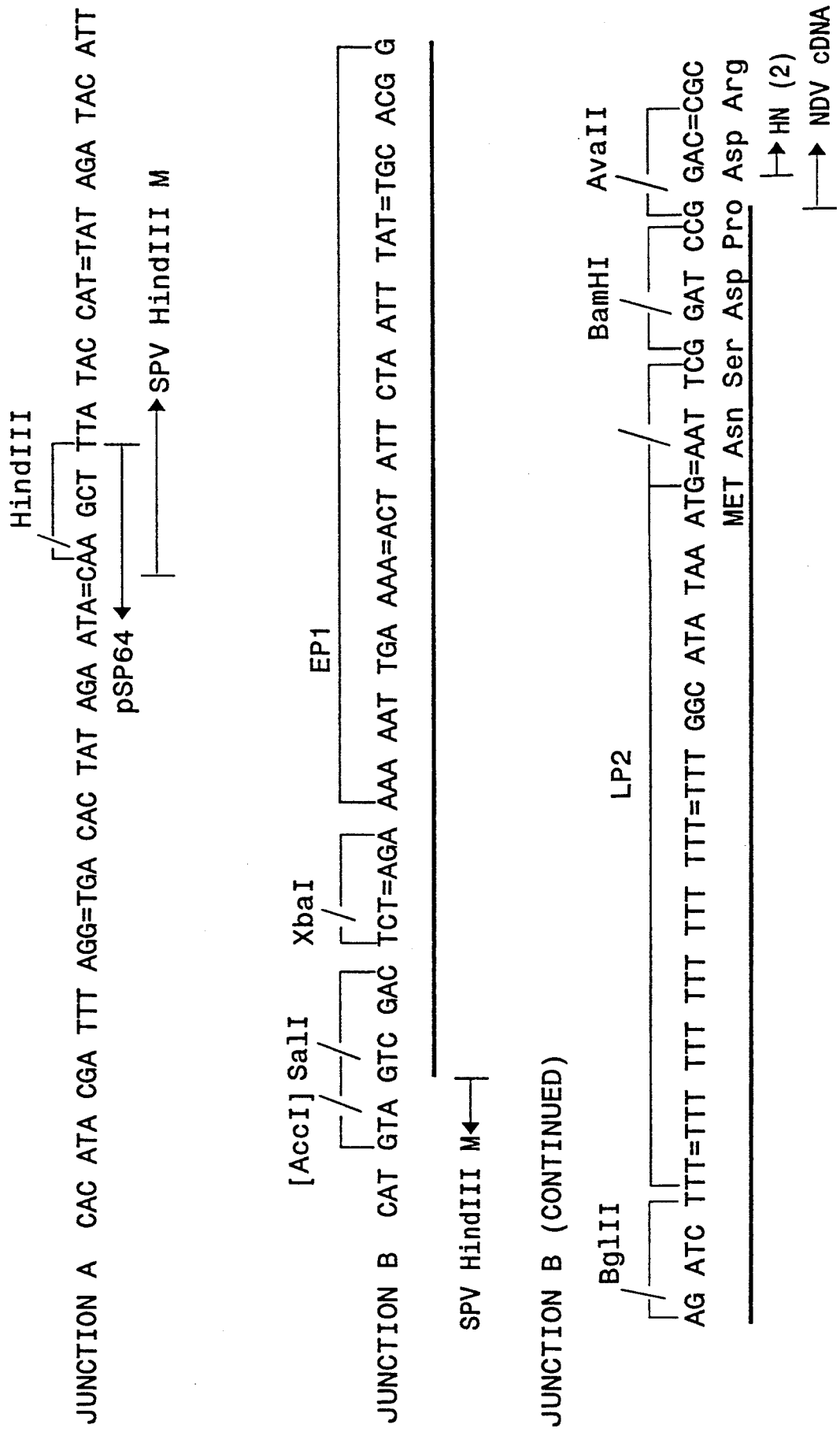
Figure 8C:
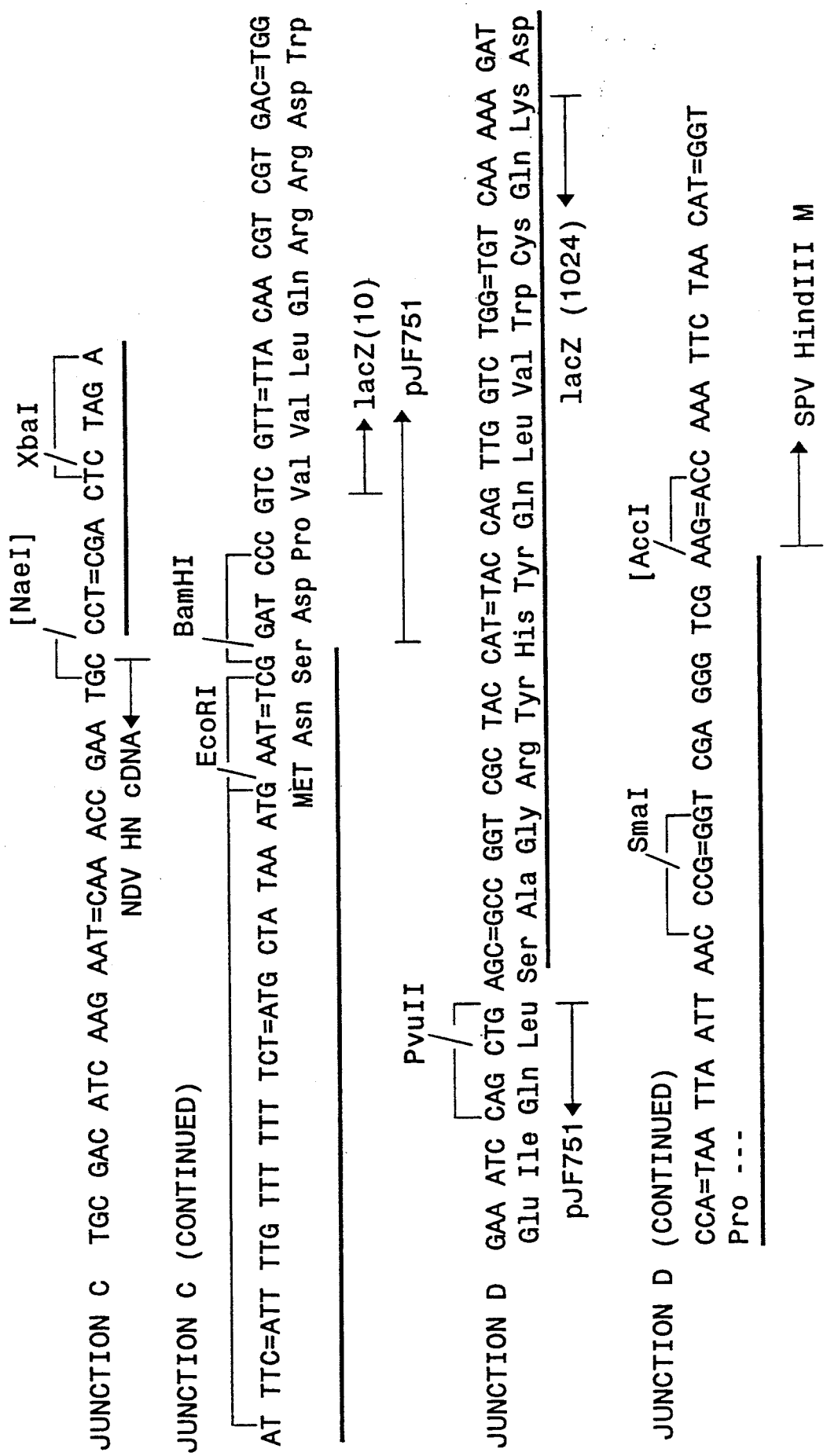
Figure 8D:
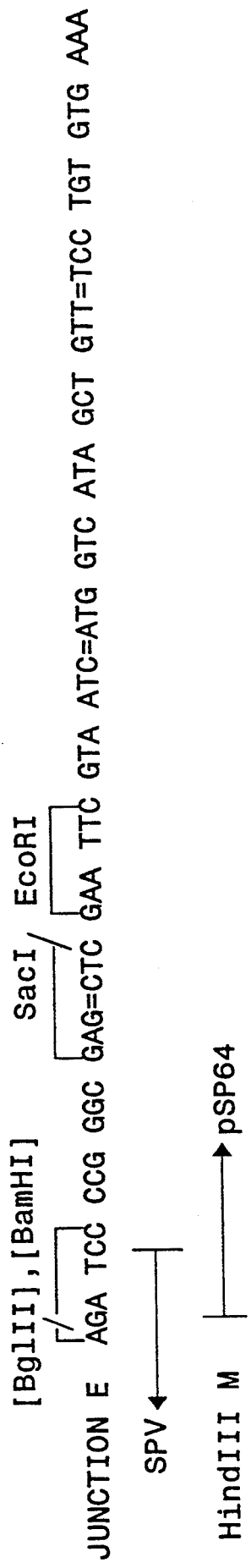

To confirm the expression of the PRV gp50 gene product, cells were infected with SPV and samples of infected cell lysates were subjected to SDS-polyacrylamide gel electrophoresis. The gel was blotted and analyzed using the WESTERN BLOTTING PROCEDURE. The swine anti-PRV serum was used to detect expression of PRV specific proteins. As shown in FIG. 6, the lysate from S-SPV-008 infected cells exhibits a specific band of approximately 48 kd, the reported size of PRV gp50 (35).

PRV gp50 is the gD homologue of HSV-1 (26). Several investigators have shown that VV expressing HSV-1 gD will protect mice against challenge with HSV-1 (6 and 34). Therefore the S-SPV-008 should be valuable as a vaccine to protect swine against PRV disease.

It is anticipated that several other PRV glycoproteins will be useful in the creation of recombinant swinepox vaccines to protect against PRV disease. These PRV glycoproteins include gpII (28), gpIII (27), and gpH (19). The PRV gpIII coding region has been engineered behind several synthetic pox promoters. The techniques utilized for the creation of S-SPV-008 will be used to create recombinant swinepox viruses expressing all four of these PRV glycoprotein genes. Such recombinant swinepox viruses will be useful as vaccines against PRV disease. Since the PRV vaccines described here do not express PRV gpX or gpI, they would be compatible with current PRV diagnostic tests (gX HerdChek ®, gI HerdChek ® and ClinEase ®) which are utilized to distinguish vaccinated animals from infected animals. S-SPV-008 has been deposited with the ATCC under Accession No. VR2339.

Example 4

S,SPV-009

S-SPV-009 is a swinepox virus that expresses at least two foreign genes. The gene for *E. coli* β-galactosidase (lacZ gene) and the gene for Newcastle's Disease virus hemagglutinin (PIN) gene were inserted into the SPV 515-85.1 ORF. The lacZ gene is under the control of a synthetic late promoter (LP1) and the HN gene is under the control of an synthetic early/late promoter (EP1LP2). S-SPV-009 was derived from S-SPV-001 (Kasza strain). This was accomplished utilizing the homology vector 538-46.26 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-009. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the marker gene.

S-SPV-009 was assayed for expression of PRV specific antigens using the BLACK PLAQUE SCREEN FOR FOREIGN GENE EXPRESSION IN RECOMBINANT SPV. Rabbit anti-NDV HN serum was shown to react specifically with S-SPV-009 plaques and not with S-SPV-008 negative control plaques. All S-SPV-009 observed plaques reacted with the swine antiserum indicating that the virus was stably expressing the NDV foreign gene. S-SPV-009 has been deposited with the ATCC under Acession No. VR 2344).

To confirm the expression of the NDV PIN gene product, cells were infected with SPV and samples of infected cell lysates were subjected to SDS-polyacrylamide gel electrophoresis. The gel was blotted and analyzed using the WESTERN BLOTTING PROCEDURE. The rabbit anti-NDV HN serum was used to detect expression of the HN protein. The lysate from S-SPV-009 infected cells exhibited a specific band of approximately 74 kd, the reported size of NDV HN (29).

Example 5

Homology Vector 520-90,15

The homology vector 520-90.15 is a plasmid useful for the insertion of foreign DNA into SPV. Plasmid 520-90.15 contains a unique NdeI restriction site into which foreign DNA may be cloned. A plasmid containing such a foreign DNA insert has been used according to the HOMOLOGOUS RECOMBINATION PROCEDURE FOR GENERATING RECOMBINANT SPV to generate a SPV containing the foreign DNA. For this procedure to be successful, it is important that the insertion site be in a region non-essential to the replication of the SPV and that the site be flanked with swinepox virus DNA appropriate for mediating homologous recombination between virus and plasmid DNAs. The unique NdeI restriction site in plasmid 520-90.15 is located within the coding region of the SPV thymidine kinase gene (32). Therefore, we have shown that the thymidine kinase gene of swinepox virus is non-essential for DNA replication and is an appropriate insertion site.

Example 6

The development of vaccines utilizing the swinepox virus to express antigens from various disease causing microorganisms can be engineered.

TRANSMISSIBLE GASTROENTERITIS VIRUS

The major neutralizing antigen of the transmissible gastroenteritis virus (TGE), glycoprotein 195, for use in the swinepox virus vector has been cloned. The clone of the neutralizing antigen is disclosed in U.S. Ser. No. 078,519, filed Jul. 27, 1987. It is contemplated that the procedures that have been used to express PRV gp50 in SPV and are disclosed herein are applicable to TGE.

PORCINE PARVOVIRUS

We have cloned the major capsid protein of the porcine (swine) parvovirus (PPV) for use in the swinepox virus vector. The clone of the capsid protein is disclosed in U.S. Pat. No. 5,068,192 issued Nov. 26, 1991. It is contemplated that the procedures that have been used to express PRV gp50 in SPV and are disclosed herein are applicable to PPV.

SWINE ROTAVIRUS

We have cloned the major neutralizing antigen of the swine rotavirus, glycoprotein 38, for use in the swinepox virus vector. The clone of glycoprotein 38 is disclosed in U.S. Pat. No. 5,068,192 issued Nov. 26, 1991. It is contemplated that the procedures that have been used to express PRV gp50 in SPV and are disclosed herein are applicable to SRV.

HOG CHOLERA VIRUS

The major neutralizing antigen of the bovine viral diarrhea (BVD) virus was cloned as disclosed in U.S. Ser. No. 225,032, filed Jul. 27, 1988. Since the BVD and hog cholera viruses are cross protective (31), the BVD virus antigen has been targeted for use in the swinepox virus vector. It is contemplated that the procedures that have been used to express PRVgp50 in SPV and are disclosed herein are applicable to BVD virus.

*SERPULINA HYODYSENTERIAE*

A protective antigen of Serpulina hyodysenteriae (3), for use in the swinepox virus vector has been cloned. It is contemplated that the procedures that have been used to express PRV gp50 in SPV and are disclosed herein are also applicable to *Serpulina hyodysenteriae.*

Antigens from the following microorganisms may also be utilized to develop animal vaccines: Swine influenza virus, foot and mouth disease virus, African swine fever virus, hog cholera virus and *Mycoplasma hyodysenteriae.*

References

1. C. Bertholet, et al., *EMBO Journal* 5, 1951–1957 (1986).

2. R. A. Bhat, et al., *Nucleic Acids Research* 17, 1159–1176 (1989).

3. D. A. Boyden, et al., *Infection and Immunity* 57, 3808-3815 (1989).

4. D. B. Boyle and B. E. H. Coupar, *Virus Research* 10 343-356 (1988).

5. R. M. Buller, et al., *Nature* 317, 813-815 (1985).

6. K. J. Cremer, et al., *Science* 228, 737-739 (1985).

7. A. J. Davidson and B. Moss, *J. Mol. Biol.* 210, 749-769 (1989).

8. A. J. Davidson and B. Moss, *J. Mol. Biol.* 210, 771-784 (1989).

9. P. L. Earl, et al., *Journal of Virology* 64, 2448-2451 (1990).

10. J. J. Esposito, et al., *Virology* 165, 313 (1988).

11. F. A. Ferrari, et al., *J. of Bacteriology* 161, 556-562 (1985).

12. C. Flexner, et al., *Vaccine* 8, 17-21 (1990).

13. S. J. Goebel, et al., *Virology* 179, 247-266 (1990).

14. U. Gubler and B. J. Hoffman, *Gene* 25, 263-269 (1983).

15. M. A. Innis, et al., *PCR Protocols A Guide to Methods and Applications,* 84-91, Academic Press, Inc., San Diego (1990).

16. S. Joshi, et al., *Journal of Virology.* 65, 5524-5530 (1991).

17. L. Kasza, et al., *Am. J. Vet. Res.* 21, 269-273 (960).

18. L. Kasza, *Diseases of Swine,* 254-260, Ed. A.D. Leman, et al., The Iowa State University Press, Ames, Iowa (1981).

19. B. G. Klupp and T. C. Mettenleiter, *Virology* 182 732-741 (1991).

20. U. K. Laemnli, *Nature* 227, 680-685 (1970).

21. B. Lominiczi, et al., *Journal of Virology* 49, 970-979 (1984).

22. T. Maniatis, et al., *Molecular Cloning:* A Laboratory Manual, Cold Spring Harbor Press, Cold Spring Harbor, N.Y. (1982).

23. R. F. Massung, and R. W. Moyer, *Virology* 180, 347-354 (1991).

24. R. F. Massung, and R. W. Moyer, *Virology* 180, 355-364 (1991).

25. B. Moss, *Science* 252, 1662-1667 (1991).

26. E. A. Petrovskis, et al., *Journal of Virology* 59 216-223 (1986).

27. A. K. Robbins et al., *Journal of Virology* 58, 339-347 (1986).

28. A. K. Robbins et al., *Journal of Virology* 61, 2691-2701 (1987).

29. A. C. R. Samson, *Journal of Virology* 67, 1199-1203 (1986).

30. J. Sambrook, et al., *Molecular Cloning A Laboratory Manual* Second Edition, Cold Spring Harbor Press, Cold Spring Harbor, N.Y. (1989).

31. Sheffy, et al., Proceedings 65th Annual Meeting of the United States Livestock Association 65, 347-353 (1961).

32. W. M. Schnitzlein and D. N. Tripathy, *Virology* 181, 727-732, (1991).

33. J. Taylor, et al., *Vaccine* 9, 19014 193, (1991).

34. M. Wachsman, et al., *Journal of General Virology* 70, 2513-2520 (1989).

35. M. W. Wathen, et al., *Journal of Virology* 51, 57-62 (1984).

36. M. Weerasinge, *Journal of Virology* 65, 5531-5534 (1991).

---

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 599 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) IND -continued / standardname="515-85.1 ORF"

( x i ) SEQUENCE DESCRIPTION: SEQ ID NO:1:

| AATGTATCCA | GAGTTGTTGA | ATGCCTTATC | GTACCTAATA | TTAATATAGA | GTTATTAACT | 60 |
| GAATAAGTAT | ATATAAATGA | TTGTTTTTAT | AATGTTTGTT | ATCGCATTTA | GTTTTGCTGT | 120 |
| ATGGTTATCA | TATACATTTT | TAAGGCCGTA | TATGATAAAT | GAAAATATAT | AAGCACTTAT | 180 |

TTTTGTTAGT ATAATAACAC A ATG CCG TCG TAT ATG TAT CCG AAG AAC GCA     231
                                                        Met Pro Ser Tyr Met Tyr Pro Lys Asn Ala
                                                         1          5                   10

AGA AAA GTA ATT TCA AAG ATT ATA TCA TTA CAA CTT GAT ATT AAA AAA     279
Arg Lys Val Ile Ser Lys Ile Ile Ser Leu Gln Leu Asp Ile Lys Lys
             15                   20                    25

CTT CCT AAA AAA TAT ATA AAT ACC ATG TTA GAA TTT GGT CTA CAT GGA     327
Leu Pro Lys Lys Tyr Ile Asn Thr Met Leu Glu Phe Gly Leu His Gly
        30                     35                      40

AAT CTA CCA GCT TGT ATG TAT AAA GAT GCC GTA TCA TAT GAT ATA AAT     375
Asn Leu Pro Ala Cys Met Tyr Lys Asp Ala Val Ser Tyr Asp Ile Asn
        45                     50                      55

AAT ATA AGA TTT TTA CCT TAT AAT TGT GTT ATG GTT AAA GAT TTA ATA     423
Asn Ile Arg Phe Leu Pro Tyr Asn Cys Val Met Val Lys Asp Leu Ile
       60                     65                    70

AAT GTT ATA AAA TCA TCA TCT GTA ATA GAT ACT AGA TTA CAT CAA TCT     471
Asn Val Ile Lys Ser Ser Ser Val Ile Asp Thr Arg Leu His Gln Ser
75                       80                    85                    90

GTA TTA AAA CAT CGT AGA GCG TTA ATA GAT TAC GGC GAT CAA GAC ATT     519
Val Leu Lys His Arg Arg Ala Leu Ile Asp Tyr Gly Asp Gln Asp Ile
                 95                    100               105

ATC ACT TTA ATG ATC ATT AAT AAG TTA CTA TCG ATA GAT GAT ATA TCC     567
Ile Thr Leu Met Ile Ile Asn Lys Leu Leu Ser Ile Asp Asp Ile Ser
            110                    115               120

TAT ATA TTA GAT AAA AAA ATA ATT CAT GTA AC     599
Tyr Ile Leu Asp Lys Lys Ile Ile His Val
      125                    130

( 2 ) INFORMATION FOR SEQ ID NO:2:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Pro Ser Tyr Met Tyr Pro Lys Asn Ala Arg Lys Val Ile Ser Lys
  1                   5                    10                        15

Ile Ile Ser Leu Gln Leu Asp Ile Lys Lys Leu Pro Lys Lys Tyr Ile
              20                    25                    30

Asn Thr Met Leu Glu Phe Gly Leu His Gly Asn Leu Pro Ala Cys Met
          35                    40                        45

Tyr Lys Asp Ala Val Ser Tyr Asp Ile Asn Asn Ile Arg Phe Leu Pro
     50                    55                    60

Tyr Asn Cys Val Met Val Lys Asp Leu Ile Asn Val Ile Lys Ser Ser
65                    70                    75                    80

Ser Val Ile Asp Thr Arg Leu His Gln Ser Val Leu Lys His Arg Arg
              85                    90                    95

Ala Leu Ile Asp Tyr Gly Asp Gln Asp Ile Ile Thr Leu Met Ile Ile
          100                    105                  110

Asn Lys Leu Leu Ser Ile Asp Asp Ile Ser Tyr Ile Leu Asp Lys Lys
        115                    120                    125

Ile Ile His Val
    130

(2) INFORMATION FOR SEQ ID NO:3:

(i) SEQUENCE CHARACTERISTICS:
        (A) LENGTH: 899 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: ~23.2
        (C) UNITS: %G (ix) FEATURE:
        (A) NAME/KEY: CDS
        (B) LOCATION: 3..662
        (D) OTHER INFORMATION: /partial
            / codonstart=3
            / function="Potential eukaryotic transcriptional regulatory protein"
            / standardname="515-85.1 ORF"

(xi) SEQUENCE DESCRIPTION: SEQ ID NO:3:

```
GA GAT ATT AAA TCA TGT AAA TGC TCG ATA TGT TCC GAC TCT ATA ACA          47
   Asp Ile Lys Ser Cys Lys Cys Ser Ile Cys Ser Asp Ser Ile Thr
   1               5                   10                  15

CAT CAT ATA TAT GAA ACA ACA TCA TGT ATA AAT TAT AAA TCT ACC GAT          95
His His Ile Tyr Glu Thr Thr Ser Cys Ile Asn Tyr Lys Ser Thr Asp
             20                  25                  30

AAT GAT CTT ATG ATA GTA TTG TTC AAT CTA ACT AGA TAT TTA ATG CAT         143
Asn Asp Leu Met Ile Val Leu Phe Asn Leu Thr Arg Tyr Leu Met His
             35                  40                  45

GGG ATG ATA CAT CCT AAT CTT ATA AGC GTA AAA GGA TGG GGT CCC CTT         191
Gly Met Ile His Pro Asn Leu Ile Ser Val Lys Gly Trp Gly Pro Leu
         50                  55                  60

ATT GGA TTA TTA ACG GGT GAT ATA GGT ATT AAT TTA AAA CTA TAT TCC         239
Ile Gly Leu Leu Thr Gly Asp Ile Gly Ile Asn Leu Lys Leu Tyr Ser
65                  70                  75

ACC ATG AAT ATA AAT GGG CTA CGG TAT GGA GAT ATT ACG TTA TCT TCA         287
Thr Met Asn Ile Asn Gly Leu Arg Tyr Gly Asp Ile Thr Leu Ser Ser
80                  85                  90                  95

TAC GAT ATG AGT AAT AAA TTA GTC TCT ATT ATT AAT ACA CCC ATA TAT         335
Tyr Asp Met Ser Asn Lys Leu Val Ser Ile Ile Asn Thr Pro Ile Tyr
                100                 105                 110

GAG TTA ATA CCG TTT ACT ACA TGT TGT TCA CTC AAT GAA TAT TAT TCA         383
Glu Leu Ile Pro Phe Thr Thr Cys Cys Ser Leu Asn Glu Tyr Tyr Ser
             115                 120                 125

AAA ATT GTG ATT TTA ATA AAT GTT ATT TTA GAA TAT ATG ATA TCT ATT         431
Lys Ile Val Ile Leu Ile Asn Val Ile Leu Glu Tyr Met Ile Ser Ile
             130                 135                 140

ATA TTA TAT AGA ATA TTG ATC GTA AAA AGA TTT AAT AAC ATT AAA GAA         479
Ile Leu Tyr Arg Ile Leu Ile Val Lys Arg Phe Asn Asn Ile Lys Glu
         145                 150                 155
```

```
TTT ATT TCA AAA GTC GTA AAT ACT GTA CTA GAA TCA TCA GGC ATA TAT     527
Phe Ile Ser Lys Val Val Asn Thr Val Leu Glu Ser Ser Gly Ile Tyr
160             165                 170                 175

TTT TGT CAG ATG CGT GTA CAT GAA CAA ATT GAA TTG GAA ATA GAT GAG     575
Phe Cys Gln Met Arg Val His Glu Gln Ile Glu Leu Glu Ile Asp Glu
            180                 185                 190

CTC ATT ATT AAT GGA TCT ATG CCT GTA CAG CTT ATG CAT TTA CTT CTA     623
Leu Ile Ile Asn Gly Ser Met Pro Val Gln Leu Met His Leu Leu Leu
                195             200                 205

AAG GTA GCT ACC ATA ATA TTA GAG GAA ATC AAA GAA ATA TAACGTATTT      672
Lys Val Ala Thr Ile Ile Leu Glu Glu Ile Lys Glu Ile
            210             215                 220

TTTCTTTTAA ATAAATAAAA ATACTTTTT TTTTAAACAA GGGGTGCTAC CTTGTCTAAT    732

TGTATCTTGT ATTTGGATC TGATGCAAGA TTATTAAATA ATCGTATGAA AAAGTAGTAG    792

ATATAGTTTA TATCGTTACT GGACATGATA TTATGTTTAG TTAATTCTTC TTTGGCATGA   852

ATTCTACACG TCGGANAAGG TAATGTATCT ATAATGGTAT AAAGCTT                899
```

( 2 ) INFORMATION FOR SEQ ID NO:4:

( i ) SEQUENCE CHARACTERISTICS:
        ( A ) LENGTH: 220 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asp Ile Lys Ser Cys Lys Cys Ser Ile Cys Ser Asp Ser Ile Thr His
 1               5                  10                  15

His Ile Tyr Glu Thr Thr Ser Cys Ile Asn Tyr Lys Ser Thr Asp Asn
             20                  25                  30

Asp Leu Met Ile Val Leu Phe Asn Leu Thr Arg Tyr Leu Met His Gly
         35                  40                  45

Met Ile His Pro Asn Leu Ile Ser Val Lys Gly Trp Gly Pro Leu Ile
     50                  55                  60

Gly Leu Leu Thr Gly Asp Ile Gly Ile Asn Leu Lys Leu Tyr Ser Thr
 65                  70                  75                  80

Met Asn Ile Asn Gly Leu Arg Tyr Gly Asp Ile Thr Leu Ser Ser Tyr
             85                  90                  95

Asp Met Ser Asn Lys Leu Val Ser Ile Ile Asn Thr Pro Ile Tyr Glu
            100                 105                 110

Leu Ile Pro Phe Thr Thr Cys Cys Ser Leu Asn Glu Tyr Tyr Ser Lys
            115                 120                 125

Ile Val Ile Leu Ile Asn Val Ile Leu Glu Tyr Met Ile Ser Ile Ile
130                 135                 140

Leu Tyr Arg Ile Leu Ile Val Lys Arg Phe Asn Asn Ile Lys Glu Phe
145                 150                 155                 160

Ile Ser Lys Val Val Asn Thr Val Leu Glu Ser Ser Gly Ile Tyr Phe
                165                 170                 175

Cys Gln Met Arg Val His Glu Gln Ile Glu Leu Glu Ile Asp Glu Leu
            180                 185                 190

Ile Ile Asn Gly Ser Met Pro Val Gln Leu Met His Leu Leu Leu Lys
        195                 200                 205

Val Ala Thr Ile Ile Leu Glu Glu Ile Lys Glu Ile
    210                 215                 220
```

( 2 ) INFORMATION FOR SEQ ID NO:5:

( i ) SEQUENCE CHARACTERISTICS:
    ( A ) LENGTH: 129 amino acids
    ( B ) TYPE: amino acid
    ( C ) STRANDEDNESS: double
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( v i ) ORIGINAL SOURCE:
    ( A ) ORGANISM: Vaccinia virus
    ( B ) STRAIN: Copenhagen ( v i i i ) POSITION IN GENOME:
    ( B ) MAP POSITION: ~23.2
    ( C ) UNITS: %G ( x i ) SEQUENCE DESCRIPTION: SEQ ID NO:5:

```
Met Phe Met Tyr Pro Glu Phe Ala Arg Lys Ala Leu Ser Lys Leu Ile
 1               5                  10                  15

Ser Lys Lys Leu Asn Ile Glu Lys Val Ser Ser Lys His Gln Leu Val
             20                  25                  30

Leu Leu Asp Tyr Gly Leu His Gly Leu Leu Pro Lys Ser Leu Tyr Leu
             35                  40                  45

Glu Ala Ile Asn Ser Asp Ile Leu Asn Val Arg Phe Phe Pro Pro Glu
 50                      55                  60

Ile Ile Asn Val Thr Asp Ile Val Lys Ala Leu Gln Asn Ser Cys Arg
 65                      70                  75                  80

Val Asp Glu Tyr Leu Lys Ala Val Ser Leu Tyr His Lys Asn Ser Leu
                 85                  90                  95

Met Val Ser Gly Pro Asn Val Val Lys Leu Met Ile Glu Tyr Asn Leu
                100                 105                 110

Leu Thr His Ser Asp Leu Glu Trp Leu Ile Asn Glu Asn Val Val Lys
            115                 120                 125

Ala
```

( 2 ) INFORMATION FOR SEQ ID NO:6:

( i ) SEQUENCE CHARACTERISTICS:
    ( A ) LENGTH: 132 amino acids
    ( B ) TYPE: amino acid
    ( C ) STRANDEDNESS: double
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( v i ) ORIGINAL SOURCE:
    ( A ) ORGANISM: Swinepox virus
    ( B ) STRAIN: Kasza ( v i i i ) POSITION IN GENOME:
    ( B ) MAP POSITION: ~23.2
    ( C ) UNITS: %G ( x i ) SEQUENCE DESCRIPTION: SEQ ID NO:6:

```
Met Pro Ser Tyr Met Tyr Pro Lys Asn Ala Arg Lys Val Ile Ser Lys
 1               5                  10                  15

Ile Ile Ser Leu Gln Leu Asp Ile Lys Lys Leu Pro Lys Lys Tyr Ile
             20                  25                  30
```

```
Asn  Thr  Met  Leu  Glu  Phe  Gly  Leu  His  Gly  Asn  Leu  Pro  Ala  Cys  Met
          35                       40                      45

Tyr  Lys  Asp  Ala  Val  Ser  Tyr  Asp  Ile  Asn  Asn  Ile  Arg  Phe  Leu  Pro
     50                       55                      60

Tyr  Asn  Cys  Val  Met  Val  Lys  Asp  Leu  Ile  Asn  Val  Ile  Lys  Ser  Ser
65                       70                      75                            80

Ser  Val  Ile  Asp  Thr  Arg  Leu  His  Gln  Ser  Val  Leu  Lys  His  Arg  Arg
               85                       90                       95

Ala  Leu  Ile  Asp  Tyr  Gly  Asp  Gln  Asp  Ile  Ile  Thr  Leu  Met  Ile  Ile
               100                      105                      110

Asn  Lys  Leu  Leu  Ser  Ile  Asp  Asp  Ile  Ser  Tyr  Ile  Leu  Asp  Lys  Lys
          115                      120                      125

Ile  Ile  His  Val
          130
```

( 2 ) INFORMATION FOR SEQ ID NO:7:

( i ) SEQUENCE CHARACTERISTICS:
        ( A ) LENGTH: 101 amino acids
        ( B ) TYPE: amino acid
        ( C ) STRANDEDNESS: double
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: C-terminal ( v i ) ORIGINAL SOURCE:
        ( A ) ORGANISM: Vaccinia virus
        ( B ) STRAIN: Copenhagen ( v i i i ) POSITION IN GENOME:
        ( B ) MAP POSITION: ~23.2
        ( C ) UNITS: %G ( x i ) SEQUENCE DESCRIPTION: SEQ ID NO:7:

```
Val  Leu  Asn  Asp  Gln  Tyr  Ala  Lys  Ile  Val  Ile  Phe  Phe  Asn  Thr  Ile
1                   5                       10                      15

Ile  Glu  Tyr  Ile  Ile  Ala  Thr  Ile  Tyr  Tyr  Arg  Leu  Thr  Val  Leu  Asn
               20                       25                      30

Asn  Tyr  Thr  Asn  Val  Lys  His  Phe  Val  Ser  Lys  Val  Leu  His  Thr  Val
          35                       40                      45

Met  Glu  Ala  Cys  Gly  Val  Leu  Phe  Ser  Tyr  Ile  Lys  Val  Asn  Asp  Lys
     50                       55                      60

Ile  Glu  His  Glu  Leu  Glu  Glu  Met  Val  Asp  Lys  Gly  Thr  Val  Pro  Ser
65                       70                      75                            80

Tyr  Leu  Tyr  His  Leu  Ser  Ile  Asn  Val  Ile  Ser  Ile  Ile  Leu  Asp  Asp
                    85                       90                      95

Ile  Asn  Gly  Thr  Arg
               100
```

( 2 ) INFORMATION FOR SEQ ID NO:8:

( i ) SEQUENCE CHARACTERISTICS:
        ( A ) LENGTH: 100 amino acids
        ( B ) TYPE: amino acid
        ( C ) STRANDEDNESS: double
        ( D ) TOPOLOGY: linear ( i i ) MOLECULE TYPE: peptide ( i i i ) HYPOTHETICAL: YES (iv) ANTI-SENSE: NO (v) FRAGMENT TYPE: C-terminal (vi) ORIGINAL SOURCE:
  (A) ORGANISM: Swinepox virus
  (B) STRAIN: Kasza (viii) POSITION IN GENOME:
  (B) MAP POSITION: ~23.2
  (C) UNITS: %G (xi) SEQUENCE DESCRIPTION: SEQ ID NO:8:

```
Ser Leu Asn Glu Tyr Tyr Ser Lys Ile Val Ile Leu Ile Asn Val Ile
 1               5                  10                  15
Leu Glu Tyr Met Ile Ser Ile Ile Leu Tyr Arg Ile Leu Ile Val Lys
             20                  25                  30
Arg Phe Asn Asn Ile Lys Glu Phe Ile Ser Lys Val Val Asn Thr Val
                 35                  40                  45
Leu Glu Ser Ser Gly Ile Tyr Phe Cys Gln Met Arg Val His Glu Gln
         50                  55                  60
Ile Glu Leu Glu Ile Asp Glu Leu Ile Ile Asn Gly Ser Met Pro Val
 65                  70                  75                  80
Gln Leu Met His Leu Leu Leu Lys Val Ala Thr Ile Ile Leu Glu Glu
                 85                  90                  95
Ile Lys Glu Ile
            100
```

(2) INFORMATION FOR SEQ ID NO:9:

(i) SEQUENCE CHARACTERISTICS:
    (A) LENGTH: 102 base pairs
    (B) TYPE: nucleic acid
    (C) STRANDEDNESS: double
    (D) TOPOLOGY: circular (ii) MOLECULE TYPE: DNA (genomic)

(iii) HYPOTHETICAL: NO (iv) ANTI-SENSE: NO (vi) ORIGINAL SOURCE:
    (A) ORGANISM: Plasmid (vii) IMMEDIATE SOURCE:
    (B) CLONE: 520-17.5 (Junction A)

(x) PUBLICATION INFORMATION:
    (A) AUTHORS: Ferrari, Franco A
           Trach, Kathleen
           Hoch, James A
    (B) TITLE: Sequence Analysis of the spo0B Locus Revels a
         Polycistronic Transcription Unit
    (C) JOURNAL: J. Bacteriol.
    (D) VOLUME: 161
    (E) ISSUE: 2
    (F) PAGES: 556-562
    (G) DATE: Feb.-1985

(xi) SEQUENCE DESCRIPTION: SEQ ID NO:9:

```
CACATACGAT TTAGGTGACA CTATAGAATA CAAGCTTTAT ACCATTATAG ATACATTACC    60

TTGTCCGACG TGTAGAATTC ATGCCAAAGA AGAATTAACT AA                      102
```

(2) INFORMATION FOR SEQ ID NO:10:

(i) SEQUENCE CHARACTERISTICS:
    (A) LENGTH: 102 base pairs
    (B) TYPE: nucleic acid
    (C) STRANDEDNESS: double ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
              ( A ) ORGANISM: Plasmid ( v i i ) IMMEDIATE SOURCE:
              ( B ) CLONE: 520-17.5 (Junction B)

( i x ) FEATURE:
              ( A ) NAME/KEY: CDS
              ( B ) LOCATION: 85..99
              ( D ) OTHER INFORMATION: /codonstart=85
                     / function="Translational start of hybrid protein"
                     / product="N-terminal peptide"
                     / number=1
                     / standardname="Translation of synthetic DNA
                     sequence"

( i x ) FEATURE:
              ( A ) NAME/KEY: CDS
              ( B ) LOCATION: 100..102
              ( C ) IDENTIFICATION METHOD: experimental
              ( D ) OTHER INFORMATION: /partial
                     / codonstart=100
                     / function="marker enzyme"
                     / product="Beta-Galactosidase"
                     / evidence=EXPERIMENTAL
                     / gene="lacZ"
                     / number=2
                     / citation=([1])

( x ) PUBLICATION INFORMATION:
              ( A ) AUTHORS: Ferrari, Franco A
                              Trach, Kathleen
                              Hoch, James A
              ( B ) TITLE: Seqquence Analysis of the spo0B Locus Reveals
                     a Polycistronic Transcription Unit
              ( C ) JOURNAL: J. Bacteriol.
              ( D ) VOLUME: 161
              ( E ) ISSUE: 2
              ( F ) PAGES: 556-562
              ( G ) DATE: Feb.-1985

( x i ) SEQUENCE DESCRIPTION: SEQ ID NO:10:

GTAGTCGACT CTAGAAAAAA TTGAAAAACT ATTCTAATTT ATTGCACGGA GATCTTTTTT        60

TTTTTTTTTT TTTTGGCAT ATAA ATG AAT TCG GAT CCC GTC                      102
                             Met Asn Ser Asp Pro Val
                              1           5       1

( 2 ) INFORMATION FOR SEQ ID NO:11:

( i ) SEQUENCE CHARACTERISTICS:
                  ( A ) LENGTH: 5 amino acids
                  ( B ) TYPE: amino acid
                  ( D ) TOPOLOGY: linear ( i i ) MOLECULE TYPE: protein ( x i ) SEQUENCE DESCRIPTION: SEQ ID NO:11:

Met Asn Ser Asp Pro
 1           5

( 2 ) INFORMATION FOR SEQ ID NO:12:

( i ) SEQUENCE CHARACTERISTICS:
                  ( A ) LENGTH: 1 amino acids
                  ( B ) TYPE: amino acid
                  ( D ) TOPOLOGY: linear ( i i ) MOLECULE TYPE: protein ( x i ) SEQUENCE DESCRIPTION: SEQ ID NO:12:

Val
1

( 2 ) INFORMATION FOR SEQ ID NO:13:

( i ) SEQUENCE CHARACTERISTICS:
        ( A ) LENGTH: 103 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 520-17.5 (Junction C)

( i x ) FEATURE:
        ( A ) NAME/KEY: CDS
        ( B ) LOCATION: 1..72
        ( C ) IDENTIFICATION METHOD: experimental
        ( D ) OTHER INFORMATION: /partial
            / codonstart=1
            / function="marker enzyme"
            / product="Beta-galactosidase"
            / evidence=EXPERIMENTAL
            / gene="lacZ"
            / number=1
            / citation=([1])

( i x ) FEATURE:
        ( A ) NAME/KEY: CDS
        ( B ) LOCATION: 73..78
        ( C ) IDENTIFICATION METHOD: experimental
        ( D ) OTHER INFORMATION: /codonstart=73
            / function="Translational finish of hybrid
            protein"
            / product="C-terminal peptide"
            / evidence=EXPERIMENTAL
            / number=2
            / standardname="Translation of synthetic DNA
            sequence"

( x ) PUBLICATION INFORMATION:
        ( A ) AUTHORS: Ferrari, Franco A
            Trach, Kathleen
            Hoch, James A
        ( B ) TITLE: Seqquence Analysis of the spo0B Locus Reveals
            a Polycistronic Transcription Unit
        ( C ) JOURNAL: J. Bacteriol.
        ( D ) VOLUME: 161
        ( E ) ISSUE: 2
        ( F ) PAGES: 556-562
        ( G ) DATE: Feb.-1985

( x i ) SEQUENCE DESCRIPTION: SEQ ID NO:13:

```
AGC CCG TCA GTA TCG GCG GAA ATC CAG CTG AGC GCC GGT CGC TAC CAT            48
Ser Pro Ser Val Ser Ala Glu Ile Gln Leu Ser Ala Gly Arg Tyr His
 1               5                  10                  15

TAC CAG TTG GTC TGG TGT CAA AAA GAT CCA TAATTAATTA ACCCGGGTCG              98
Tyr Gln Leu Val Trp Cys Gln Lys Asp Pro
            20                   1

AAGAC                                                                     103
```

( 2 ) INFORMATION FOR SEQ ID NO:14:

( i ) SEQUENCE CHARACTERISTICS:

(A) LENGTH: 24 amino acids
(B) TYPE: amino acid
(D) TOPOLOGY: linear (ii) MOLECULE TYPE: protein (xi) SEQUENCE DESCRIPTION: SEQ ID NO:14:

Ser Pro Ser Val Ser Ala Glu Ile Gln Leu Ser Ala Gly Arg Tyr His
 1               5                  10                 15
Tyr Gln Leu Val Trp Cys Gln Lys
            20

(2) INFORMATION FOR SEQ ID NO:15:

(i) SEQUENCE CHARACTERISTICS:
(A) LENGTH: 2 amino acids
(B) TYPE: amino acid
(D) TOPOLOGY: linear (ii) MOLECULE TYPE: protein (xi) SEQUENCE DESCRIPTION: SEQ ID NO:15:

Asp Pro
 1

(2) INFORMATION FOR SEQ ID NO:16:

(i) SEQUENCE CHARACTERISTICS:
(A) LENGTH: 48 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 520-17.5 (Junction D)

(xi) SEQUENCE DESCRIPTION: SEQ ID NO:16:

AGATCCCCGG GCGAGCTCGA ATTCGTAATC ATGGTCATAG CTGTTTCC                48

(2) INFORMATION FOR SEQ ID NO:17:

(i) SEQUENCE CHARACTERISTICS:
(A) LENGTH: 57 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 538-46.26 (Junction A)

(xi) SEQUENCE DESCRIPTION: SEQ ID NO:17:

CACATACGAT TTAGGTGACA CTATAGAATA CAAGCTTTAT ACCATTATAG ATACATT     57

(2) INFORMATION FOR SEQ ID NO:18:

( i ) SEQUENCE CHARACTERISTICS:
    ( A ) LENGTH: 102 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Plasmid ( v i i ) IMMEDIATE SOURCE:
    ( B ) CLONE: 538-46.16 (Junction B)

( i x ) FEATURE:
    ( A ) NAME/KEY: CDS
    ( B ) LOCATION: 91..102
    ( C ) IDENTIFICATION METHOD: experimental
    ( D ) OTHER INFORMATION: /partial
        / codonstart=91
        / function="marker enzyme"
        / product="Beta-Galactosidase"
        / evidence=EXPERIMENTAL
        / gene="lacZ"
        / number=2
        / citation=([1])

( i x ) FEATURE:
    ( A ) NAME/KEY: CDS
    ( B ) LOCATION: 76..90
    ( D ) OTHER INFORMATION: /partial
        / codonstart=76
        / function="Translational start of hybrid protein"
        / product="N-terminal peptide"
        / number=1
        / standardname="Translation of synthetic DNA
        sequence"

( x ) PUBLICATION INFORMATION:
    ( A ) AUTHORS: Ferrari, Franco A
        Trach, Kathleen
        Hoch, James A
    ( B ) TITLE: Seqquence Analysis of the spo0B Locus Reveals
        a Polycistronic Transcription Unit
    ( C ) JOURNAL: J. Bacteriol.
    ( D ) VOLUME: 161
    ( E ) ISSUE: 2
    ( F ) PAGES: 556-562
    ( G ) DATE: Feb.-1985

( x i ) SEQUENCE DESCRIPTION: SEQ ID NO:18:

```
AAGCTGGTAG ATTTCCATGT AGGGCCGCCT GCAGGTCGAC TCTAGAATTT CATTTGTTT        60

TTTTCTATGC TATAA ATG AAT TCG GAT CCC GTC GTT TTA CAA                   102
              Met Asn Ser Asp Pro Val Val Leu Gln
              1               5       1
```

( 2 ) INFORMATION FOR SEQ ID NO:19:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: protein ( x i ) SEQUENCE DESCRIPTION: SEQ ID NO:19:

Met Asn Ser Asp Pro
1               5

( 2 ) INFORMATION FOR SEQ ID NO:20:

( i ) SEQUENCE CHARACTERISTICS:

-continued ( A ) LENGTH: 4 amino acids
           ( B ) TYPE: amino acid
           ( D ) TOPOLOGY: linear ( i i ) MOLECULE TYPE: protein ( x i ) SEQUENCE DESCRIPTION: SEQ ID NO:20:

Val  Val  Leu  Gln
 1

( 2 ) INFORMATION FOR SEQ ID NO:21:

( i ) SEQUENCE CHARACTERISTICS:
           ( A ) LENGTH: 206 base pairs
           ( B ) TYPE: nucleic acid
           ( C ) STRANDEDNESS: double
           ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
           ( A ) ORGANISM: Plasmid ( v i i ) IMMEDIATE SOURCE:
           ( B ) CLONE: 538-46.16 (Junction C)

( i x ) FEATURE:
           ( A ) NAME/KEY: CDS
           ( B ) LOCATION: 1..63
           ( C ) IDENTIFICATION METHOD: experimental
           ( D ) OTHER INFORMATION: /partial
                / codonstart=1
                / function="marker enzyme"
                / product="Beta-galactosidase"
                / evidence=EXPERIMENTAL
                / number=1
                / citation=([1])

( i x ) FEATURE:
           ( A ) NAME/KEY: CDS
           ( B ) LOCATION: 64..69
           ( C ) IDENTIFICATION METHOD: experimental
           ( D ) OTHER INFORMATION: /codonstart=64
                / function="Translational finish of hybrid
                protein"
                / product="C-terminal peptide"
                / evidence=EXPERIMENTAL
                / standardname="Translation of synthetic DNA
                sequence"

( i x ) FEATURE:
           ( A ) NAME/KEY: CDS
           ( B ) LOCATION: 177..185
           ( C ) IDENTIFICATION METHOD: experimental
           ( D ) OTHER INFORMATION: /codonstart=177
                / function="Translational start of hybrid protein"
                / product="N-terminal peptide"
                / evidence=EXPERIMENTAL
                / standardname="Translation of synthetic DNA
                sequence"

( i x ) FEATURE:
           ( A ) NAME/KEY: CDS
           ( B ) LOCATION: 186..206
           ( C ) IDENTIFICATION METHOD: experimental
           ( D ) OTHER INFORMATION: /partial
                / codonstart=186
                / function="glycoprotein"
                / product="PRV gp50"
                / evidence=EXPERIMENTAL
                / gene="gp50"
                / number=3
                / citation=([2])

( x ) PUBLICATION INFORMATION:
           ( A ) AUTHORS: Ferrari, Franco A

Trach, Kathleen
Hoch, James A
(B) TITLE: Seqquence Analysis of the spo0B Locus Reveals
a Polycistronic Transcription Unit
(C) JOURNAL: J. Bacteriol.
(D) VOLUME: 161
(E) ISSUE: 2
(F) PAGES: 556-562
(G) DATE: Feb.-1985

(x) PUBLICATION INFORMATION:
(A) AUTHORS: Petrovskis, Erik A
Timmins, James G
Armentrout, Marty A
Marchioli, Carmine C
Jr. Yancy, Robert J
Post, Leonard E
(B) TITLE: DNA Sequence of the Gene for Pseudorabies
Virus gp50, a Glycoprotein without N-Linked
Glycosylation
(C) JOURNAL: J. Virol.
(D) VOLUME: 59
(E) ISSUE: 2
(F) PAGES: 216-223
(G) DATE: Aug.-1986

(xi) SEQUENCE DESCRIPTION: SEQ ID NO:21:

| GTA | TCG | GCG | GAA | ATC | CAG | CTG | AGC | GCC | GGT | CGC | TAC | CAT | TAC | CAG | TTG | 48 |
| Val | Ser | Ala | Glu | Ile | Gln | Leu | Ser | Ala | Gly | Arg | Tyr | His | Tyr | Gln | Leu | |
| 1 | | | | 5 | | | | | 10 | | | | | 15 | | |

| GTC | TGG | TGT | CAA | AAA | GAT | CCA | TAATTAATTA | ACCCGGCCGC | CTGCAGGTCG | 99 |
| Val | Trp | Cys | Gln | Lys | Asp | Pro | | | | |
| | 20 | | | | | 1 | | | | |

ACTCTAGAAA AAATTGAAAA ACTATTCTAA TTTATTGCAC GGAGATCTTT TTTTTTTTT    159

TTTTTTTGG CATATAA ATG AAT TCG CTC GCA GCG CTA TTG GCG GCG          206
                    Met Asn Ser Leu Ala Ala Leu Leu Ala Ala
                     1           1               5

(2) INFORMATION FOR SEQ ID NO:22:

(i) SEQUENCE CHARACTERISTICS:
(A) LENGTH: 21 amino acids
(B) TYPE: amino acid
(D) TOPOLOGY: linear (ii) MOLECULE TYPE: protein (xi) SEQUENCE DESCRIPTION: SEQ ID NO:22:

| Val | Ser | Ala | Glu | Ile | Gln | Leu | Ser | Ala | Gly | Arg | Tyr | His | Tyr | Gln | Leu |
| 1 | | | | 5 | | | | | 10 | | | | | 15 | |

| Val | Trp | Cys | Gln | Lys |
| | | | | 20 |

(2) INFORMATION FOR SEQ ID NO:23:

(i) SEQUENCE CHARACTERISTICS:
(A) LENGTH: 2 amino acids
(B) TYPE: amino acid
(D) TOPOLOGY: linear (ii) MOLECULE TYPE: protein (xi) SEQUENCE DESCRIPTION: SEQ ID NO:23:

Asp Pro
 1

(2) INFORMATION FOR SEQ ID NO:24:

(i) SEQUENCE CHARACTERISTICS:
(A) LENGTH: 3 amino acids
(B) TYPE: amino acid (D) TOPOLOGY: linear (ii) MOLECULE TYPE: protein (xi) SEQUENCE DESCRIPTION: SEQ ID NO:24:

Met Asn Ser
 1

(2) INFORMATION FOR SEQ ID NO:25:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:25:

Leu Ala Ala Leu Leu Ala Ala
 1               5

(2) INFORMATION FOR SEQ ID NO:26:

(i) SEQUENCE CHARACTERISTICS:
        (A) LENGTH: 101 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.16 (Junction D)

(ix) FEATURE:
        (A) NAME/KEY: CDS
        (B) LOCATION: 1..15
        (D) OTHER INFORMATION: /partial
            / codonstart=1
            / function="glycoprotein"
            / product="PRV gp63"
            / gene="gp63"
            / number=1
            / citation=([1])

(x) PUBLICATION INFORMATION:
        (A) AUTHORS: Petrovskis, Erik A
            Timmins, James G
            Post, Lenoard E
        (B) TITLE: Use of Lambda-gt11 To Isolate Genes for two
            Pseudorabies Virus Glycoproteins with homology to
            Herpes Simplex Virus and Varicella-Zoster Virus
            Glycoproteins
        (C) JOURNAL: J. Virol.
        (D) VOLUME: 60
        (E) ISSUE: 1
        (F) PAGES: 185-193
        (G) DATE: Oct.-1986

(xi) SEQUENCE DESCRIPTION: SEQ ID NO:26:

```
CGC GTG CAC CAC GAG GGACTCTAGA GGATCCATAA TTAATTAATT AATTTTTATC      55
Arg Val His His Glu
 1               5

CCGGGTCGAC CTGCAGGCGG CCGGGTCGAC CTGCAGGCGG CCAGAC                   101
```

(2) INFORMATION FOR SEQ ID NO:27:

(i) SEQUENCE CHARACTERISTICS:

( A ) LENGTH: 5 amino acids
( B ) TYPE: amino acid
( D ) TOPOLOGY: linear ( i i ) MOLECULE TYPE: protein ( x i ) SEQUENCE DESCRIPTION: SEQ ID NO:27:

Arg Val His His Glu
 1               5

( 2 ) INFORMATION FOR SEQ ID NO:28:

( i ) SEQUENCE CHARACTERISTICS:
( A ) LENGTH: 57 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Plasmid ( v i i ) IMMEDIATE SOURCE:
( B ) CLONE: 538-46.16 (Junction E)

( x i ) SEQUENCE DESCRIPTION: SEQ ID NO:28:

AGATCCCCGG GCGAGCTCGA ATTCGTAATC ATGGTCATAG CTGTTTCCTG TGTGAAA    57

( 2 ) INFORMATION FOR SEQ ID NO:29:

( i ) SEQUENCE CHARACTERISTICS:
( A ) LENGTH: 1907 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: Newcastle disease virus
( B ) STRAIN: B1

( v i i ) IMMEDIATE SOURCE:
( B ) CLONE: 137-23.803 (PSY1142)

( v i i i ) POSITION IN GENOME:
( B ) MAP POSITION: ~50%
( C ) UNITS: %G ( i x ) FEATURE:
( A ) NAME/KEY: CDS
( B ) LOCATION: 92..1822
( D ) OTHER INFORMATION: /codonstart=92
/ product="NDV heamagglutinin-Neuraminidase"
/ gene="HN"
/ number=1

( x i ) SEQUENCE DESCRIPTION: SEQ ID NO:29:

ACGGGTAGAA CGGTAAGAGA GGCCGCCCCT CAATTGCGAG CCAGACTTCA CAACCTCCGT 60

TCTACCGCTT CACCGACAAC AGTCCTCAAT C ATG GAC CGC GCC GTT AGC CAA 112
Met Asp Arg Ala Val Ser Gln
1 5

GTT GCG TTA GAG AAT GAT GAA AGA GAG GCA AAA AAT ACA TGG CGC TTG 160
Val Ala Leu Glu Asn Asp Glu Arg Glu Ala Lys Asn Thr Trp Arg Leu
10 15 20

```
ATA TTC CGG ATT GCA ATC TTA TTC TTA ACA GTA GTG ACC TTG GCT ATA      208
Ile Phe Arg Ile Ala Ile Leu Phe Leu Thr Val Val Thr Leu Ala Ile
    25                  30                  35

TCT GTA GCC TCC CTT TTA TAT AGC ATG GGG GCT AGC ACA CCT AGC GAT      256
Ser Val Ala Ser Leu Leu Tyr Ser Met Gly Ala Ser Thr Pro Ser Asp
40                  45                  50                  55

CTT GTA GGC ATA CCG ACT AGG ATT TCC AGG GCA GAA GAA AAG ATT ACA      304
Leu Val Gly Ile Pro Thr Arg Ile Ser Arg Ala Glu Glu Lys Ile Thr
                60                  65                  70

TCT ACA CTT GGT TCC AAT CAA GAT GTA GTA GAT AGG ATA TAT AAG CAA      352
Ser Thr Leu Gly Ser Asn Gln Asp Val Val Asp Arg Ile Tyr Lys Gln
                    75                  80                  85

GTG GCC CTT GAG TCT CCA TTG GCA TTG TTA AAT ACT GAG ACC ACA ATT      400
Val Ala Leu Glu Ser Pro Leu Ala Leu Leu Asn Thr Glu Thr Thr Ile
            90                  95                  100

ATG AAC GCA ATA ACA TCT CTC TCT TAT CAG ATT AAT GGA GCT GCA AAC      448
Met Asn Ala Ile Thr Ser Leu Ser Tyr Gln Ile Asn Gly Ala Ala Asn
        105                 110                 115

AAC AGC GGG TGG GGG GCA CCT ATT CAT GAC CCA GAT TAT ATA GGG GGG      496
Asn Ser Gly Trp Gly Ala Pro Ile His Asp Pro Asp Tyr Ile Gly Gly
120                 125                 130                 135

ATA GGC AAA GAA CTC ATT GTA GAT GAT GCT AGT GAT GTC ACA TCA TTC      544
Ile Gly Lys Glu Leu Ile Val Asp Asp Ala Ser Asp Val Thr Ser Phe
                140                 145                 150

TAT CCC TCT GCA TTT CAA GAA CAT CTG AAT TTT ATC CCG GCG CCT ACT      592
Tyr Pro Ser Ala Phe Gln Glu His Leu Asn Phe Ile Pro Ala Pro Thr
                    155                 160                 165

ACA GGA TCA GGT TGC ACT CGA ATA CCC TCA TTT GAC ATG AGT GCT ACC      640
Thr Gly Ser Gly Cys Thr Arg Ile Pro Ser Phe Asp Met Ser Ala Thr
            170                 175                 180

CAT TAC TGC TAC ACC CAT AAT GTA ATA TTG TCT GGA TGC AGA GAT CAC      688
His Tyr Cys Tyr Thr His Asn Val Ile Leu Ser Gly Cys Arg Asp His
        185                 190                 195

TCA CAC TCA CAT CAG TAT TTA GCA CTT GGT GTG CTC CGG ACA TCT GCA      736
Ser His Ser His Gln Tyr Leu Ala Leu Gly Val Leu Arg Thr Ser Ala
200                 205                 210                 215

ACA GGG AGG GTA TTC TTT TCT ACT CTG CGT TCC ATC AAC CTG GAC GAC      784
Thr Gly Arg Val Phe Phe Ser Thr Leu Arg Ser Ile Asn Leu Asp Asp
                220                 225                 230

ACC CAA AAT CGG AAG TCT TGC AGT GTG AGT GCA ACT CCC CTG GGT TGT      832
Thr Gln Asn Arg Lys Ser Cys Ser Val Ser Ala Thr Pro Leu Gly Cys
                    235                 240                 245

GAT ATG CTG TGC TCG AAA GCC ACG GAG ACA GAG GAA GAA GAT TAT AAC      880
Asp Met Leu Cys Ser Lys Ala Thr Glu Thr Glu Glu Glu Asp Tyr Asn
            250                 255                 260

TCA GCT GTC CCT ACG CGG ATG GTA CAT GGG AGG TTA GGG TTC GAC GGC      928
Ser Ala Val Pro Thr Arg Met Val His Gly Arg Leu Gly Phe Asp Gly
        265                 270                 275

CAA TAT CAC GAA AAG GAC CTA GAT GTC ACA ACA TTA TTC GGG GAC TGG      976
Gln Tyr His Glu Lys Asp Leu Asp Val Thr Thr Leu Phe Gly Asp Trp
280                 285                 290                 295

GTG GCC AAC TAC CCA GGA GTA GGG GGT GGA TCT TTT ATT GAC AGC CGC     1024
Val Ala Asn Tyr Pro Gly Val Gly Gly Gly Ser Phe Ile Asp Ser Arg
                300                 305                 310

GTG TGG TTC TCA GTC TAC GGA GGG TTA AAA CCC AAT ACA CCC AGT GAC     1072
Val Trp Phe Ser Val Tyr Gly Gly Leu Lys Pro Asn Thr Pro Ser Asp
                    315                 320                 325

ACT GTA CAG GAA GGG AAA TAT GTG ATA TAC AAG CGA TAC AAT GAC ACA     1120
Thr Val Gln Glu Gly Lys Tyr Val Ile Tyr Lys Arg Tyr Asn Asp Thr
            330                 335                 340

TGC CCA GAT GAG CAA GAC TAC CAG ATT CGA ATG GCC AAG TCT TCG TAT     1168
```

| | | | | | | | | | | | | | | | | |
|---|---|---|---|---|---|---|---|---|---|---|---|---|---|---|---|---|
| Cys | Pro | Asp | Glu | Gln | Asp | Tyr | Gln | Ile | Arg | Met | Ala | Lys | Ser | Ser | Tyr | |
| 345 | | | | | 350 | | | | | 355 | | | | | | |

```
AAG CCT GGA CGG TTT GGT GGG AAA CGC ATA CAG CAG GCT ATC TTA TCT           1216
Lys Pro Gly Arg Phe Gly Gly Lys Arg Ile Gln Gln Ala Ile Leu Ser
360             365                 370                 375

ATC AAA GTG TCA ACA TCC TTA GGC GAA GAC CCG GTA CTG ACT GTA CCG           1264
Ile Lys Val Ser Thr Ser Leu Gly Glu Asp Pro Val Leu Thr Val Pro
                380                 385                 390

CCC AAC ACA GTC ACA CTC ATG GGG GCC GAA GGC AGA ATT CTC ACA GTA           1312
Pro Asn Thr Val Thr Leu Met Gly Ala Glu Gly Arg Ile Leu Thr Val
            395                 400                 405

GGG ACA TCC CAT TTC TTG TAT CAG CGA GGG TCA TCA TAC TTC TCT CCC           1360
Gly Thr Ser His Phe Leu Tyr Gln Arg Gly Ser Ser Tyr Phe Ser Pro
        410                 415                 420

GCG TTA TTA TAT CCT ATG ACA GTC AGC AAC AAA ACA GCC ACT CTT CAT           1408
Ala Leu Leu Tyr Pro Met Thr Val Ser Asn Lys Thr Ala Thr Leu His
    425                 430                 435

AGT CCT TAT ACA TTC AAT GCC TTC ACT CGG CCA GGT AGT ATC CCT TGC           1456
Ser Pro Tyr Thr Phe Asn Ala Phe Thr Arg Pro Gly Ser Ile Pro Cys
440                 445                 450                 455

CAG GCT TCA GCA AGA TGC CCC AAC TCA TGT GTT ACT GGA GTC TAT ACA           1504
Gln Ala Ser Ala Arg Cys Pro Asn Ser Cys Val Thr Gly Val Tyr Thr
                460                 465                 470

GAT CCA TAT CCC CTA ATC TTC TAT AGA AAC CAC ACC TTG CGA GGG GTA           1552
Asp Pro Tyr Pro Leu Ile Phe Tyr Arg Asn His Thr Leu Arg Gly Val
            475                 480                 485

TTC GGG ACA ATG CTT GAT GGT GAA CAA GCA AGA CTT AAC CCT GCG TCT           1600
Phe Gly Thr Met Leu Asp Gly Glu Gln Ala Arg Leu Asn Pro Ala Ser
        490                 495                 500

GCA GTA TTC GAT AGC ACA TCC CGC AGT CGC ATA ACT CGA GTG AGT TCA           1648
Ala Val Phe Asp Ser Thr Ser Arg Ser Arg Ile Thr Arg Val Ser Ser
    505                 510                 515

AGC AGC ATC AAA GCA GCA TAC ACA ACA TCA ACT TGT TTT AAA GTG GTC           1696
Ser Ser Ile Lys Ala Ala Tyr Thr Thr Ser Thr Cys Phe Lys Val Val
520                 525                 530                 535

AAG ACC AAT AAG ACC TAT TGT CTC AGC ATT GCT GAA ATA TCT AAT ACT           1744
Lys Thr Asn Lys Thr Tyr Cys Leu Ser Ile Ala Glu Ile Ser Asn Thr
                540                 545                 550

CTC TTC GGA GAA TTC AGA ATC GTC CCG TTA CTA GTT GAG ATC CTC AAA           1792
Leu Phe Gly Glu Phe Arg Ile Val Pro Leu Leu Val Glu Ile Leu Lys
            555                 560                 565

GAT GAC GGG GTT AGA GAA GCC AGG TCT GGC TAGTTGAGTC AACTATGAAA            1842
Asp Asp Gly Val Arg Glu Ala Arg Ser Gly
        570                 575

GAGTTGGAAA GATGGCATTG TATCACCTAT CTTCTGCGAC ATCAAGAATC AAACCGAATG         1902

CCGGC                                                                     1907
```

( 2 ) INFORMATION FOR SEQ ID NO:30:

( i ) SEQUENCE CHARACTERISTICS:
        ( A ) LENGTH: 577 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Met Asp Arg Ala Val Ser Gln Val Ala Leu Glu Asn Asp Glu Arg Glu
 1               5                  10                  15

Ala Lys Asn Thr Trp Arg Leu Ile Phe Arg Ile Ala Ile Leu Phe Leu
             20                  25                  30

Thr Val Val Thr Leu Ala Ile Ser Val Ala Ser Leu Leu Tyr Ser Met
```

```
                35                           40                              45
Gly  Ala  Ser  Thr  Pro  Ser  Asp  Leu  Val  Gly  Ile  Pro  Thr  Arg  Ile  Ser
     50                       55                      60

Arg  Ala  Glu  Glu  Lys  Ile  Thr  Ser  Thr  Leu  Gly  Ser  Asn  Gln  Asp  Val
65                       70                      75                           80

Val  Asp  Arg  Ile  Tyr  Lys  Gln  Val  Ala  Leu  Glu  Ser  Pro  Leu  Ala  Leu
                85                       90                           95

Leu  Asn  Thr  Glu  Thr  Thr  Ile  Met  Asn  Ala  Ile  Thr  Ser  Leu  Ser  Tyr
               100                      105                     110

Gln  Ile  Asn  Gly  Ala  Ala  Asn  Asn  Ser  Gly  Trp  Gly  Ala  Pro  Ile  His
          115                      120                     125

Asp  Pro  Asp  Tyr  Ile  Gly  Gly  Ile  Gly  Lys  Glu  Leu  Ile  Val  Asp  Asp
     130                      135                     140

Ala  Ser  Asp  Val  Thr  Ser  Phe  Tyr  Pro  Ser  Ala  Phe  Gln  Glu  His  Leu
145                      150                     155                          160

Asn  Phe  Ile  Pro  Ala  Pro  Thr  Thr  Gly  Ser  Gly  Cys  Thr  Arg  Ile  Pro
               165                      170                     175

Ser  Phe  Asp  Met  Ser  Ala  Thr  His  Tyr  Cys  Tyr  Thr  His  Asn  Val  Ile
               180                      185                     190

Leu  Ser  Gly  Cys  Arg  Asp  His  Ser  His  Ser  His  Gln  Tyr  Leu  Ala  Leu
               195                      200                     205

Gly  Val  Leu  Arg  Thr  Ser  Ala  Thr  Gly  Arg  Val  Phe  Phe  Ser  Thr  Leu
     210                      215                     220

Arg  Ser  Ile  Asn  Leu  Asp  Asp  Thr  Gln  Asn  Arg  Lys  Ser  Cys  Ser  Val
225                      230                     235                          240

Ser  Ala  Thr  Pro  Leu  Gly  Cys  Asp  Met  Leu  Cys  Ser  Lys  Ala  Thr  Glu
               245                      250                     255

Thr  Glu  Glu  Glu  Asp  Tyr  Asn  Ser  Ala  Val  Pro  Thr  Arg  Met  Val  His
               260                      265                     270

Gly  Arg  Leu  Gly  Phe  Asp  Gly  Gln  Tyr  His  Glu  Lys  Asp  Leu  Asp  Val
               275                      280                     285

Thr  Thr  Leu  Phe  Gly  Asp  Trp  Val  Ala  Asn  Tyr  Pro  Gly  Val  Gly  Gly
     290                      295                     300

Gly  Ser  Phe  Ile  Asp  Ser  Arg  Val  Trp  Phe  Ser  Val  Tyr  Gly  Gly  Leu
305                      310                     315                          320

Lys  Pro  Asn  Thr  Pro  Ser  Asp  Thr  Val  Gln  Glu  Gly  Lys  Tyr  Val  Ile
               325                      330                     335

Tyr  Lys  Arg  Tyr  Asn  Asp  Thr  Cys  Pro  Asp  Glu  Gln  Asp  Tyr  Gln  Ile
               340                      345                     350

Arg  Met  Ala  Lys  Ser  Ser  Tyr  Lys  Pro  Gly  Arg  Phe  Gly  Gly  Lys  Arg
               355                      360                     365

Ile  Gln  Gln  Ala  Ile  Leu  Ser  Ile  Lys  Val  Ser  Thr  Ser  Leu  Gly  Glu
               370                      375                     380

Asp  Pro  Val  Leu  Thr  Val  Pro  Pro  Asn  Thr  Val  Thr  Leu  Met  Gly  Ala
385                      390                     395                          400

Glu  Gly  Arg  Ile  Leu  Thr  Val  Gly  Thr  Ser  His  Phe  Leu  Tyr  Gln  Arg
               405                      410                     415

Gly  Ser  Ser  Tyr  Phe  Ser  Pro  Ala  Leu  Leu  Tyr  Pro  Met  Thr  Val  Ser
               420                      425                     430

Asn  Lys  Thr  Ala  Thr  Leu  His  Ser  Pro  Tyr  Thr  Phe  Asn  Ala  Phe  Thr
          435                      440                     445

Arg  Pro  Gly  Ser  Ile  Pro  Cys  Gln  Ala  Ser  Ala  Arg  Cys  Pro  Asn  Ser
     450                      455                     460

Cys  Val  Thr  Gly  Val  Tyr  Thr  Asp  Pro  Tyr  Pro  Leu  Ile  Phe  Tyr  Arg
465                      470                     475                          480
```

| | | | | | | | | | | | | | |
|---|---|---|---|---|---|---|---|---|---|---|---|---|---|
| Asn | His | Thr | Leu | Arg<br>485 | Gly | Val | Phe | Gly | Thr<br>490 | Met | Leu | Asp | Gly | Glu<br>495 | Gln |
| Ala | Arg | Leu | Asn<br>500 | Pro | Ala | Ser | Ala | Val<br>505 | Phe | Asp | Ser | Thr | Ser<br>510 | Arg | Ser |
| Arg | Ile | Thr<br>515 | Arg | Val | Ser | Ser | Ser<br>520 | Ser | Ile | Lys | Ala | Ala<br>525 | Tyr | Thr | Thr |
| Ser | Thr<br>530 | Cys | Phe | Lys | Val<br>535 | Val | Lys | Thr | Asn | Lys<br>540 | Thr | Tyr | Cys | Leu | Ser |
| Ile<br>545 | Ala | Glu | Ile | Ser | Asn<br>550 | Thr | Leu | Phe | Gly | Glu<br>555 | Phe | Arg | Ile | Val | Pro<br>560 |
| Leu | Leu | Val | Glu | Ile<br>565 | Leu | Lys | Asp | Asp | Gly<br>570 | Val | Arg | Glu | Ala | Arg<br>575 | Ser |

Gly ( 2 ) INFORMATION FOR SEQ ID NO:31:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction A)

( x i ) SEQUENCE DESCRIPTION: SEQ ID NO:31:

CACATACGAT TTAGGTGACA CTATAGAATA CAAGCTTTAT ACCATTATAG ATACATT    57

( 2 ) INFORMATION FOR SEQ ID NO:32:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction B)

( i x ) FEATURE:
        ( A ) NAME/KEY: exon
        ( B ) LOCATION: 88..102
        ( D ) OTHER INFORMATION: /codonstart=88
        / function="Translational start of hybrid protein"
        / product="N-terminal peptide"
        / number=1
        / standardname="Translation of synthetic DNA
        sequence"

( i x ) FEATURE:
        ( A ) NAME/KEY: CDS
        ( B ) LOCATION: 103..108
        ( C ) IDENTIFICATION METHOD: experimental
        ( D ) OTHER INFORMATION: /partial -continued / codonstart=103
/ product="NDV Heamagglutinin-Neuraminidase"
/ evidence=EXPERIMENTA (E) ISSUE: 2
(F) PAGES: 556-562
(G) DATE: Feb.-1985

(xi) SEQUENCE DESCRIPTION: SEQ ID NO:34:

```
TGCGACATCA AGAATCAAAC CGAATGCCCT CGACTCTAGA ATTTCATTTT GTTTTTTTCT        60

ATGCTATAA ATG AAT TCG GAT CCC GTC GTT TTA CAA CGT CGT GAC TGG         108
          Met Asn Ser Asp Pro Val Val Leu Gln Arg Arg Asp Trp
          1               5               1               5
```

(2) INFORMATION FOR SEQ ID NO:35:

(i) SEQUENCE CHARACTERISTICS:
(A) LENGTH: 5 amino acids
(B) TYPE: amino acid
(D) TOPOLOGY: linear (ii) MOLECULE TYPE: protein (xi) SEQUENCE DESCRIPTION: SEQ ID NO:35:

```
Met Asn Ser Asp Pro
1               5
```

(2) INFORMATION FOR SEQ ID NO:36:

(i) SEQUENCE CHARACTERISTICS:
(A) LENGTH: 8 amino acids
(B) TYPE: amino acid
(D) TOPOLOGY: linear (ii) MOLECULE TYPE: protein (xi) SEQUENCE DESCRIPTION: SEQ ID NO:36:

```
Val Val Leu Gln Arg Arg Asp Trp
1               5
```

(2) INFORMATION FOR SEQ ID NO:37:

(i) SEQUENCE CHARACTERISTICS:
(A) LENGTH: 108 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 538-46.26

(ix) FEATURE:
(A) NAME/KEY: CDS
(B) LOCATION: 1..54
(C) IDENTIFICATION METHOD: experimental
(D) OTHER INFORMATION: /partial
/ codonstart=1
/ function="marker enzyme"
/ product="Beta-galactosidase"
/ evidence=EXPERIMENTAL
/ gene="lacZ"
/ number=1
/ citation=([1])

(ix) FEATURE:
(A) NAME/KEY: CDS
(B) LOCATION: 55..63
(C) IDENTIFICATION METHOD: experimental
(D) OTHER INFORMATION: /codonstart=55

/function="Translational finish of hybrid protein"
/product="C-terminal peptide"
/evidence=EXPERIMENTAL
/number=2
/standardname="Translation of synthetic DNA sequence"

(xi) SEQUENCE DESCRIPTION: SEQ ID NO:37:

```
GAA ATC CAG CTG AGC GCC GGT CGC TAC CAT TAC CAG TTG GTC TGG TGT      48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG AGGGTCGAAG ACCAAATTCT         100
Gln Lys Asp Pro
              1

AACATGGT                                                            108
```

(2) INFORMATION FOR SEQ ID NO:38:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:38:

```
Glu Ile Gln Leu Ser Ala Gly Arg Tyr His Tyr Gln Leu Val Trp Cys
 1               5                  10                  15
Gln Lys
```

(2) INFORMATION FOR SEQ ID NO:39:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO:39:

```
Asp Pro
 1
```

(2) INFORMATION FOR SEQ ID NO:40:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26 (Junction E)

(xi) SEQUENCE DESCRIPTION: SEQ ID NO:40:

```
AGATCCCCGG GCGAGCTCGA ATTCGTAATC ATGGTCATAG CTGTTTCCTG TGTGAAA      57
```

(2) INFORMATION FOR SEQ ID NO:41:

(i) SEQUENCE CHARACTERISTICS:
        (A) LENGTH: 27 base pairs

```
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
            ( A ) ORGANISM: Pseudorabies virus
Synthetic oligonucleotide                                                   primer ( x i ) SEQUENCE DESCRIPTION: SEQ ID NO:41:

CGCGAATTCG CTCGCAGCGC TATTGGC                                                       2 7

( 2 ) INFORMATION FOR SEQ ID NO:42:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
            ( A ) ORGANISM: Pseudorabies virus
Synthetic oligonucleotide                                                   primer ( x i ) SEQUENCE DESCRIPTION: SEQ ID NO:42:

GTAGGAGTGG CTGCTGAAG                                                                1 9
```

What is claimed is:

1. A recombinant swinepox virus which comprises a foreign DNA inserted within the swinepox virus genomic DNA, wherein the foreign DNA sequence is inserted within the larger HindIII to BglII subfragment of the HindIII M fragment of the genomic DNA, and is capable of being expressed in a swinepox virus infected hose cell.

2. The recombinant swinepox virus of claim 1, wherein the insertion site is within an open reading frame contained within the HindIII to BglII subfragment, wherein the open reading frame contains the unique AccI site present in the HindIII to BglII subfragment.

3. The recombinant swinepox virus of claim 2, wherein the insertion size is the AccI restriction endonuclease site located in the HindIII to BglII subfragment.

4. The recombinant swinepox virus of claim 1, wherein the recombinant swinepox virus further comprises a foreign DNA sequence inserted within the swinepox virus thymidine kinase gene.

5. The recombinant swinepox virus of claim 1, wherein the foreign DNA sequence encodes a detectable marker.

6. The recombinant swinepox virus of claim 5, wherein the detectable marker is *E. coli* β-galactosidase.

7. The recombinant swinepox virus of claim 6, designated S-SPV-003 (ATCC Accession No. VR 2335).

8. The recombinant swinepox virus of claim 1, wherein the foreign DNA sequence encodes an antigenic polypeptide.

9. The recombinant swinepox virus of claim 8, wherein the antigenic polypeptide is selected from the group consisting essentially of PRV glycoprotein 50, PRV glycoprotein II, PRV glycoprotein III, PRV glycoprotein H, TGE glycoprotein 195, TGE matrix protein,, swine rotavirus glycoprotein 38, swine parvovirus capsid protein, *Serpulina hyodysenteriae* protective antigen, BVDV glycoprotein 55, NDV hemagglutinin-neuraminidase, swine flu hemagglutinin and swine flu neuraminidase.

10. The recombinant swinepox virus of claim 9, wherein the antigenic polypeptide is PRV glycoprotein 50.

11. The recombinant swinepox virus of claim 10, designated S-SPV-008 (ATCC Accession No. VR 2339).

12. A homology vector for producing a recombinant swinepox virus by inserting a foreign DNA sequence into the genomic DNA of a swinepox virus which comprises a foreign DNA sequence, wherein the foreign DNA sequence is controlled by a promoter and flanked by a nucleotide sequence homologous to the swinepox virus genomic DNA present within the HindIII to BglII subfragment of HindIII M fragment.

13. The homology vector of claim 12, wherein the nucleotide sequence flanking the foreign DNA sequence is homologous to the swinepox virus genomic DNA present within the AccI restriction endonuclease site located in the HindIII to BglII subfragment.

14. The homology vector of claim 12, wherein the foreign DNA sequence encodes a detectable marker.

15. The homology vector of claim 13, wherein the detectable marker is *E. coli* β-galactosidase.

16. The homology vector of claim 12, wherein the foreign DNA sequence encodes an antigenic polypeptide.

17. The homology vector of claim 16, wherein the antigenic polypeptide is pseudorabies virus glycoprotein 50.

18. A recombinant swinepox virus of claim 8, wherein the antigenic polypeptide is or is from, Foot and Mouth Disease Virus, Hog Cholera Virus, Swine Influenza Virus, African Swine Fever Virus or *Mycoplasma hyopneumoniae*.

19. A recombinant swinepox virus of claim 8, designated S-SPV-009 (ATCC Accession No. VR 2344).

20. A homology vector of claim 16, wherein the antigenic polypeptide is or is from *Serpulina hyodysenteriae*, Foot and Mouth Disease Virus, Hog Cholera Virus, Swine Influenza Virus, African Swine Fever Virus or *Mycoplasma hyopneumoniae*.

* * * * *

UNITED STATES PATENT AND TRADEMARK OFFICE
CERTIFICATE OF CORRECTION

PATENT NO. : 5,382,425
DATED : January 17, 1995
INVENTOR(S) : Mark D. Cochran, et al.

It is certified that error appears in the above-indentified patent and that said Letters Patent is hereby corrected as shown below:

Columns 19 - 22 should be deleted to appear as per attached columns 19-66, to include Sequence listing.

Signed and Sealed this

Eighteenth Day of April, 1995

Attest:

BRUCE LEHMAN

Attesting Officer

*Commissioner of Patents and Trademarks*

3. D. A. Boyden, et al., *Infection and Immunity* 57, 3808–3815 (1989).
4. D. B. Boyle and B. E. H. Coupar, *Virus Research* 10 343–356 (1988).
5. R. M. Buller, et al., *Nature* 317, 813–815 (1985).
6. K. J. Cremer, et al., *Science* 228, 737–739 (1985).
7. A. J. Davidson and B. Moss, *J. Mol. Biol.* 210, 749–769 (1989).
8. A. J. Davidson and B. Moss, *J. Mol. Biol.* 210, 771–784 (1989).
9. P. L. Earl, et al., *Journal of Virology* 64, 2448–2451 (1990).
10. J. J. Esposito, et al., *Virology* 165, 313 (1988).
11. F. A. Ferrari, et al., *J. of Bacteriology* 161, 556–562 (1985).
12. C. Flexner, et al., *Vaccine* 8, 17–21 (1990).
13. S. J. Goebel, et al., *Virology* 179, 247–266 (1990).
14. U. Gubler and B. J. Hoffman, *Gene* 25, 263–269 (1983).
15. M. A. Innis, et al., *PCR Protocols A Guide to Methods and Applications*, 84–91, Academic Press, Inc., San Diego (1990).
16. S. Joshi, et al., *Journal of Virology.* 65, 5524–5530 (1991).
17. L. Kasza, et al., *Am. J. Vet. Res.* 21, 269–273 (960).
18. L. Kasza, *Diseases of Swine*, 254–260, Ed. A.D. Leman, et al., The Iowa State University Press, Ames, Iowa (1981).
19. B. G. Klupp and T. C. Mettenleiter, *Virology* 182 732–741 (1991).
20. U. K. Laemnli, *Nature* 227, 680–685 (1970).
21. B. Lominiczi, et al., *Journal of Virology* 49, 970–979 (1984).
22. T. Maniatis, et al., *Molecular Cloning*: A Laboratory Manual, Cold Spring Harbor Press, Cold Spring Harbor, N.Y. (1982).
23. R. F. Massung, and R. W. Moyer, *Virology* 180, 347–354 (1991).
24. R. F. Massung, and R. W. Moyer, *Virology* 180, 355–364 (1991).
25. B. Moss, *Science* 252, 1662–1667 (1991).
26. E. A. Petrovskis, et al., *Journal of Virology* 59 216–223 (1986).
27. A. K. Robbins et al., *Journal of Virology* 58, 339–347 (1986).
28. A. K. Robbins et al., *Journal of Virology* 61, 2691–2701 (1987).
29. A. C. R. Samson, *Journal of Virology* 67, 1199–1203 (1986).
30. J. Sambrook, et al., *Molecular Cloning A Laboratory Manual* Second Edition, Cold Spring Harbor Press, Cold Spring Harbor, N.Y. (1989).
31. Sheffy, et al., Proceedings 65th Annual Meeting of the United States Livestock Association 65, 347–353 (1961).
32. W. M. Schnitzlein and D. N. Tripathy, *Virology* 181, 727–732, (1991).
33. J. Taylor, et al., *Vaccine* 9, 19014 193, (1991).
34. M. Wachsman, et al., *Journal of General Virology* 70, 2513–2520 (1989).
35. M. W. Wathen, et al., *Journal of Virology* 51, 57–62 (1984).
36. M. Weerasinge, *Journal of Virology* 65, 5531–5534 (1991).

---

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 599 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

&n

/ standardname="515-85.1 ORF"

( x i ) SEQUENCE DESCRIPTION: SEQ ID NO:1:

```
AATGTATCCA GAGTTGTTGA ATGCCTTATC GTACCTAATA TTAATATAGA GTTATTAACT      60

GAATAAGTAT ATATAAATGA TTGTTTTTAT AATGTTTGTT ATCGCATTTA GTTTGCTGT      120

ATGGTTATCA TATACATTTT TAAGGCCGTA TATGATAAAT GAAAATATAT AAGCACTTAT     180

TTTTGTTAGT ATAATAACAC A ATG CCG TCG TAT ATG TAT CCG AAG AAC GCA      231
                         Met Pro Ser Tyr Met Tyr Pro Lys Asn Ala
                          1           5                      10
```

| AGA | AAA | GTA | ATT | TCA | AAG | ATT | ATA | TCA | TTA | CAA | CTT | GAT | ATT | AAA | AAA | 279 |
|---|---|---|---|---|---|---|---|---|---|---|---|---|---|---|---|---|
| Arg | Lys | Val | Ile | Ser | Lys | Ile | Ile | Ser | Leu | Gln | Leu | Asp | Ile | Lys | Lys | |
|  |  |  |  | 15 |  |  |  | 20 |  |  |  |  | 25 |  |  | |

| CTT | CCT | AAA | AAA | TAT | ATA | AAT | ACC | ATG | TTA | GAA | TTT | GGT | CTA | CAT | GGA | 327 |
|---|---|---|---|---|---|---|---|---|---|---|---|---|---|---|---|---|
| Leu | Pro | Lys | Lys | Tyr | Ile | Asn | Thr | Met | Leu | Glu | Phe | Gly | Leu | His | Gly | |
|  |  |  | 30 |  |  |  |  | 35 |  |  |  |  | 40 |  |  | |

| AAT | CTA | CCA | GCT | TGT | ATG | TAT | AAA | GAT | GCC | GTA | TCA | TAT | GAT | ATA | AAT | 375 |
|---|---|---|---|---|---|---|---|---|---|---|---|---|---|---|---|---|
| Asn | Leu | Pro | Ala | Cys | Met | Tyr | Lys | Asp | Ala | Val | Ser | Tyr | Asp | Ile | Asn | |
|  |  |  | 45 |  |  |  |  | 50 |  |  |  |  | 55 |  |  | |

| AAT | ATA | AGA | TTT | TTA | CCT | TAT | AAT | TGT | GTT | ATG | GTT | AAA | GAT | TTA | ATA | 423 |
|---|---|---|---|---|---|---|---|---|---|---|---|---|---|---|---|---|
| Asn | Ile | Arg | Phe | Leu | Pro | Tyr | Asn | Cys | Val | Met | Val | Lys | Asp | Leu | Ile | |
|  | 60 |  |  |  |  | 65 |  |  |  |  | 70 |  |  |  |  | |

| AAT | GTT | ATA | AAA | TCA | TCA | TCT | GTA | ATA | GAT | ACT | AGA | TTA | CAT | CAA | TCT | 471 |
|---|---|---|---|---|---|---|---|---|---|---|---|---|---|---|---|---|
| Asn | Val | Ile | Lys | Ser | Ser | Ser | Val | Ile | Asp | Thr | Arg | Leu | His | Gln | Ser | |
| 75 |  |  |  |  | 80 |  |  |  |  | 85 |  |  |  |  | 90 | |

| GTA | TTA | AAA | CAT | CGT | AGA | GCG | TTA | ATA | GAT | TAC | GGC | GAT | CAA | GAC | ATT | 519 |
|---|---|---|---|---|---|---|---|---|---|---|---|---|---|---|---|---|
| Val | Leu | Lys | His | Arg | Arg | Ala | Leu | Ile | Asp | Tyr | Gly | Asp | Gln | Asp | Ile | |
|  |  |  |  | 95 |  |  |  |  | 100 |  |  |  |  | 105 |  | |

| ATC | ACT | TTA | ATG | ATC | ATT | AAT | AAG | TTA | CTA | TCG | ATA | GAT | GAT | ATA | TCC | 567 |
|---|---|---|---|---|---|---|---|---|---|---|---|---|---|---|---|---|
| Ile | Thr | Leu | Met | Ile | Ile | Asn | Lys | Leu | Leu | Ser | Ile | Asp | Asp | Ile | Ser | |
|  |  |  | 110 |  |  |  |  | 115 |  |  |  |  | 120 |  |  | |

| TAT | ATA | TTA | GAT | AAA | AAA | ATA | ATT | CAT | GTA | AC |  |  |  |  |  | 599 |
|---|---|---|---|---|---|---|---|---|---|---|---|---|---|---|---|---|
| Tyr | Ile | Leu | Asp | Lys | Lys | Ile | Ile | His | Val |  |  |  |  |  |  | |
|  |  | 125 |  |  |  |  | 130 |  |  |  |  |  |  |  |  | |

( 2 ) INFORMATION FOR SEQ ID NO:2:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Ser Tyr Met Tyr Pro Lys Asn Ala Arg Lys Val Ile Ser Lys
 1           5                      10                      15

Ile Ile Ser Leu Gln Leu Asp Ile Lys Lys Leu Pro Lys Lys Tyr Ile
              20                  25                  30

Asn Thr Met Leu Glu Phe Gly Leu His Gly Asn Leu Pro Ala Cys Met
          35                  40                  45

Tyr Lys Asp Ala Val Ser Tyr Asp Ile Asn Asn Ile Arg Phe Leu Pro
     50                  55                  60

Tyr Asn Cys Val Met Val Lys Asp Leu Ile Asn Val Ile Lys Ser Ser
 65                  70                  75                  80

Ser Val Ile Asp Thr Arg Leu His Gln Ser Val Leu Lys His Arg Arg
              85                  90                  95

Ala Leu Ile Asp Tyr Gly Asp Gln Asp Ile Ile Thr Leu Met Ile Ile
          100                 105                 110

Asn Lys Leu Leu Ser Ile Asp Asp Ile Ser Tyr Ile Leu Asp Lys Lys
          115                 120                 125
```

Ile Ile His Val
    130

( 2 ) INFORMATION FOR SEQ ID NO:3:

( i ) SEQUENCE CHARACTERISTICS:
    ( A ) LENGTH: 899 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Swinepox virus
    ( B ) STRAIN: Kasza
    ( C ) INDIVIDUAL ISOLATE: S-SPV-001

( v i i ) IMMEDIATE SOURCE:
    ( B ) CLONE: 515-85.1

( v i i i ) POSITION IN GENOME:
( B ) MAP POSITION: ~23.2
( C ) UNITS: %G ( i x ) FEATURE:
( A ) NAME/KEY: CDS
( B ) LOCATION: 3..662
( D ) OTHER INFORMATION: /partial
/ codonstart = 3
/ function = "Potential eukaryotic transcriptional regulatory protein"
/ standardname = "515-85.1 ORF"

( x i ) SEQUENCE DESCRIPTION: SEQ ID NO:3:

GA GAT ATT AAA TCA TGT AAA TGC TCG ATA TGT TCC GAC TCT ATA ACA 47
Asp Ile Lys Ser Cys Lys Cys Ser Ile Cys Ser Asp Ser Ile Thr
1 5 10 15

CAT CAT ATA TAT GAA ACA ACA TCA TGT ATA AAT TAT AAA TCT ACC GAT 95
His His Ile Tyr Glu Thr Thr Ser Cys Ile Asn Tyr Lys Ser Thr Asp
20 25 30

AAT GAT CTT ATG ATA GTA TTG TTC AAT CTA ACT AGA TAT TTA ATG CAT 143
Asn Asp Leu Met Ile Val Leu Phe Asn Leu Thr Arg Tyr Leu Met His
35 40 45

GGG ATG ATA CAT CCT AAT CTT ATA AGC GTA AAA GGA TGG GGT CCC CTT 191
Gly Met Ile His Pro Asn Leu Ile Ser Val Lys Gly Trp Gly Pro Leu
50 55 60

ATT GGA TTA TTA ACG GGT GAT ATA GGT ATT AAT TTA AAA CTA TAT TCC 239
Ile Gly Leu Leu Thr Gly Asp Ile Gly Ile Asn Leu Lys Leu Tyr Ser
65 70 75

ACC ATG AAT ATA AAT GGG CTA CGG TAT GGA GAT ATT ACG TTA TCT TCA 287
Thr Met Asn Ile Asn Gly Leu Arg Tyr Gly Asp Ile Thr Leu Ser Ser
80 85 90 95

TAC GAT ATG AGT AAT AAA TTA GTC TCT ATT ATT AAT ACA CCC ATA TAT 335
Tyr Asp Met Ser Asn Lys Leu Val Ser Ile Ile Asn Thr Pro Ile Tyr
100 105 110

GAG TTA ATA CCG TTT ACT ACA TGT TGT TCA CTC AAT GAA TAT TAT TCA 383
Glu Leu Ile Pro Phe Thr Thr Cys Cys Ser Leu Asn Glu Tyr Tyr Ser
115 120 125

AAA ATT GTG ATT TTA ATA AAT GTT ATT TTA GAA TAT ATG ATA TCT ATT 431
Lys Ile Val Ile Leu Ile Asn Val Ile Leu Glu Tyr Met Ile Ser Ile
130 135 140

ATA TTA TAT AGA ATA TTG ATC GTA AAA AGA TTT AAT AAC ATT AAA GAA 479
Ile Leu Tyr Arg Ile Leu Ile Val Lys Arg Phe Asn Asn Ile Lys Glu
145 150 155

-continued

```
TTT ATT TCA AAA GTC GTA AAT ACT GTA CTA GAA TCA TCA GGC ATA TAT     527
Phe Ile Ser Lys Val Val Asn Thr Val Leu Glu Ser Ser Gly Ile Tyr
160                 165                 170                 175

TTT TGT CAG ATG CGT GTA CAT GAA CAA ATT GAA TTG GAA ATA GAT GAG     575
Phe Cys Gln Met Arg Val His Glu Gln Ile Glu Leu Glu Ile Asp Glu
                180                 185                 190

CTC ATT ATT AAT GGA TCT ATG CCT GTA CAG CTT ATG CAT TTA CTT CTA     623
Leu Ile Ile Asn Gly Ser Met Pro Val Gln Leu Met His Leu Leu Leu
        195                 200                 205

AAG GTA GCT ACC ATA ATA TTA GAG GAA ATC AAA GAA ATA TAACGTATTT     672
Lys Val Ala Thr Ile Ile Leu Glu Glu Ile Lys Glu Ile
            210                 215                 220

TTTCTTTTAA ATAAATAAAA ATACTTTTTT TTTTAAACAA GGGGTGCTAC CTTGTCTAAT    732
TGTATCTTGT ATTTTGGATC TGATGCAAGA TTATTAAATA ATCGTATGAA AAAGTAGTAG    792
ATATAGTTTA TATCGTTACT GGACATGATA TTATGTTTAG TTAATTCTTC TTTGGCATGA    852
ATTCTACACG TCGGANAAGG TAATGTATCT ATAATGGTAT AAAGCTT                  899
```

( 2 ) INFORMATION FOR SEQ ID NO:4:

( i ) SEQUENCE CHARACTERISTICS:
        ( A ) LENGTH: 220 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asp Ile Lys Ser Cys Lys Cys Ser Ile Cys Ser Asp Ser Ile Thr His
1               5                   10                  15

His Ile Tyr Glu Thr Thr Ser Cys Ile Asn Tyr Lys Ser Thr Asp Asn
            20                  25                  30

Asp Leu Met Ile Val Leu Phe Asn Leu Thr Arg Tyr Leu Met His Gly
        35                  40                  45

Met Ile His Pro Asn Leu Ile Ser Val Lys Gly Trp Gly Pro Leu Ile
    50                  55                  60

Gly Leu Leu Thr Gly Asp Ile Gly Ile Asn Leu Lys Leu Tyr Ser Thr
65                  70                  75                  80

Met Asn Ile Asn Gly Leu Arg Tyr Gly Asp Ile Thr Leu Ser Ser Tyr
            85                  90                  95

Asp Met Ser Asn Lys Leu Val Ser Ile Ile Asn Thr Pro Ile Tyr Glu
        100                 105                 110

Leu Ile Pro Phe Thr Thr Cys Cys Ser Leu Asn Glu Tyr Tyr Ser Lys
    115                 120                 125

Ile Val Ile Leu Ile Asn Val Ile Leu Glu Tyr Met Ile Ser Ile Ile
130                 135                 140

Leu Tyr Arg Ile Leu Ile Val Lys Arg Phe Asn Asn Ile Lys Glu Phe
145                 150                 155                 160

Ile Ser Lys Val Val Asn Thr Val Leu Glu Ser Ser Gly Ile Tyr Phe
            165                 170                 175

Cys Gln Met Arg Val His Glu Gln Ile Glu Leu Glu Ile Asp Glu Leu
        180                 185                 190

Ile Ile Asn Gly Ser Met Pro Val Gln Leu Met His Leu Leu Leu Lys
    195                 200                 205

Val Ala Thr Ile Ile Leu Glu Glu Ile Lys Glu Ile
210                 215                 220
```

( 2 ) INFORMATION FOR SEQ ID NO:5:

(i) SEQUENCE CHARACTERISTICS:
    (A) LENGTH: 129 amino acids
    (B) TYPE: amino acid
    (C) STRANDEDNESS: double
    (D) TOPOLOGY: linear (ii) MOLECULE TYPE: peptide (iii) HYPOTHETICAL: YES (iv) ANTI-SENSE: NO (v) FRAGMENT TYPE: N-terminal (vi) ORIGINAL SOURCE:
    (A) ORGANISM: Vaccinia virus
    (B) STRAIN: Cop

```
Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
    50              55                  60

Tyr Asn Cys Val Met Val Lys Asp Leu Ile Asn Val Ile Lys Ser Ser
65                  70                  75                      80

Ser Val Ile Asp Thr Arg Leu His Gln Ser Val Leu Lys His Arg Arg
                85                  90                  95

Ala Leu Ile Asp Tyr Gly Asp Gln Asp Ile Ile Thr Leu Met Ile Ile
            100                 105                 110

Asn Lys Leu Leu Ser Ile Asp Asp Ile Ser Tyr Ile Leu Asp Lys Lys
        115                 120                 125

Ile Ile His Val
        130
```

( 2 ) INFORMATION FOR SEQ ID NO:7:

( i ) SEQUENCE CHARACTERISTICS:
        ( A ) LENGTH: 101 amino acids
        ( B ) TYPE: amino acid
        ( C ) STRANDEDNESS: double
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: C-terminal ( v i ) ORIGINAL SOURCE:
        ( A ) ORGANISM: Vaccinia virus
        ( B ) STRAIN: Copenhagen ( v i i i ) POSITION IN GENOME:
        ( B ) MAP POSITION: ~23.2
        ( C ) UNITS: %G ( x i ) SEQUENCE DESCRIPTION: SEQ ID NO:7:

```
Val Leu Asn Asp Gln Tyr Ala Lys Ile Val Ile Phe Phe Asn Thr Ile
1               5                   10                  15

Ile Glu Tyr Ile Ile Ala Thr Ile Tyr Tyr Arg Leu Thr Val Leu Asn
            20                  25                  30

Asn Tyr Thr Asn Val Lys His Phe Val Ser Lys Val Leu His Thr Val
        35                  40                  45

Met Glu Ala Cys Gly Val Leu Phe Ser Tyr Ile Lys Val Asn Asp Lys
    50                  55                  60

Ile Glu His Glu Leu Glu Glu Met Val Asp Lys Gly Thr Val Pro Ser
65                  70                  75                      80

Tyr Leu Tyr His Leu Ser Ile Asn Val Ile Ser Ile Ile Leu Asp Asp
                85                  90                  95

Ile Asn Gly Thr Arg
            100
```

( 2 ) INFORMATION FOR SEQ ID NO:8:

( i ) SEQUENCE CHARACTERISTICS:
        ( A ) LENGTH: 100 amino acids
        ( B ) TYPE: amino acid
        ( C ) STRANDEDNESS: double
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: C-terminal ( v i ) ORIGINAL SOURCE:
    ( A ) ORGANISM: Swinepox virus
    ( B ) STRAIN: Kasza ( v i i i ) POSITION IN GENOME:
    ( B ) MAP POSITION: ~23.2
    ( C ) UNITS: %G ( x i ) SEQUENCE DESCRIPTION: SEQ ID NO:8:

```
Ser Leu Asn Glu Tyr Tyr Ser Lys Ile Val Ile Leu Ile Asn Val Ile
 1               5                  10                 15
Leu Glu Tyr Met Ile Ser Ile Ile Leu Tyr Arg Ile Leu Ile Val Lys
            20                 25                 30
Arg Phe Asn Asn Ile Lys Glu Phe Ile Ser Lys Val Val Asn Thr Val
        35                 40                 45
Leu Glu Ser Ser Gly Ile Tyr Phe Cys Gln Met Arg Val His Glu Gln
    50                 55                 60
Ile Glu Leu Glu Ile Asp Glu Leu Ile Ile Asn Gly Ser Met Pro Val
65                  70                 75                  80
Gln Leu Met His Leu Leu Leu Lys Val Ala Thr Ile Ile Leu Glu Glu
            85                 90                 95
Ile Lys Glu Ile
           100
```

( 2 ) INFORMATION FOR SEQ ID NO:9:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 520-17.5 (Junction A)

( x ) PUBLICATION INFORMATION:
        ( A ) AUTHORS: Ferrari, Franco A
                  Trach, Kathleen
                  Hoch, James A
        ( B ) TITLE: Sequence Analysis of the spo0B Locus Revels a
            Polycistronic Transcription Unit
        ( C ) JOURNAL: J. Bacteriol.
        ( D ) VOLUME: 161
        ( E ) ISSUE: 2
        ( F ) PAGES: 556-562
        ( G ) DATE: Feb.-1985

( x i ) SEQUENCE DESCRIPTION: SEQ ID NO:9:

```
CACATACGAT TTAGGTGACA CTATAGAATA CAAGCTTTAT ACCATTATAG ATACATTACC    60
TTGTCCGACG TGTAGAATTC ATGCCAAAGA AGAATTAACT AA                     102
```

( 2 ) INFORMATION FOR SEQ ID NO:10:

( i ) SEQUENCE CHARACTERISTICS:
        ( A ) LENGTH: 102 base pairs
        ( B ) TYPE: nucleic acid
        ( C ) STRANDEDNESS: double (D) TOPOLOGY: circular (i i) MOLECULE TYPE: DNA (genomic)

(i i i) HYPOTHETICAL: NO (i v) ANTI-SENSE: NO (v i) ORIGINAL SOURCE:
    (A) ORGANISM: Plasmid (v i i) IMMEDIATE SOURCE:
    (B) CLONE: 520-17.5 (Junction B)

(i x) FEATURE:
    (A) NAME/KEY: CDS
    (B) LOCATION: 85..99
    (D) OTHER INFORMATION: /codonstart=85
        / function="Translational start of hybrid protein"
        / product="N-terminal peptide"
        / number=1
        / standardname="Translation of synthetic DNA sequence"

(i x) FEATURE:
    (A) NAME/KEY: CDS
    (B) LOCATION: 100..102
    (C) IDENTIFICATION METHOD: experimental
    (D) OTHER INFORMATION: /partial
        / codonstart=100
        / function="marker enzyme"
        / product="Beta-Galactosidase"
        / evidence=EXPERIMENTAL
        / gene="lacZ"
        / number=2
        / citation=([1])

(x) PUBLICATION INFORMATION:
    (A) AUTHORS: Ferrari, Franco A
        Trach, Kathleen
        Hoch, James A
    (B) TITLE: Seqquence Analysis of the spo0B Locus Reveals a Polycistronic Transcription Unit
    (C) JOURNAL: J. Bacteriol.
    (D) VOLUME: 161
    (E) ISSUE: 2
    (F) PAGES: 556-562
    (G) DATE: Feb.-1985

(x i) SEQUENCE DESCRIPTION: SEQ ID NO:10:

```
GTAGTCGACT CTAGAAAAAA TTGAAAAACT ATTCTAATTT ATTGCACGGA GATCTTTTTT      60

TTTTTTTTTT TTTTGGCAT ATAA ATG AAT TCG GAT CCC GTC                    102
                          Met Asn Ser Asp Pro Val
                           1               5   1
```

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (i i) MOLECULE TYPE: protein (x i) SEQUENCE DESCRIPTION: SEQ ID NO:11:

```
Met Asn Ser Asp Pro
 1               5
```

(2) INFORMATION FOR SEQ ID NO:12:

(i) SEQUENCE CHARACTERISTICS:
        (A) LENGTH: 1 amino acids
        (B) TYPE: amino acid
        (D) TOPOLOGY: linear (i i) MOLECULE TYPE: protein ( x i ) SEQUENCE DESCRIPTION: SEQ ID NO:12:

Val
1

( 2 ) INFORMATION FOR SEQ ID NO:13:

( i ) SEQUENCE CHARACTERISTICS:
        ( A ) LENGTH: 103 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 520-17.5 (Junction C)

( i x ) FEATURE:
        ( A ) NAME/KEY: CDS
        ( B ) LOCATION: 1..72
        ( C ) IDENTIFICATION METHOD: experimental
        ( D ) OTHER INFORMATION: /partial
            / codonstart=1
            / function="marker enzyme"
            / product="Beta-galactosidase"
            / evidence=EXPERIMENTAL
            / gene="lacZ"
            / number=1
            / citation=([1])

( i x ) FEATURE:
        ( A ) NAME/KEY: CDS
        ( B ) LOCATION: 73..78
        ( C ) IDENTIFICATION METHOD: experimental
        ( D ) OTHER INFORMATION: /codonstart=73
            / function="Translational finish of hybrid protein"
            / product="C-terminal peptide"
            / evidence=EXPERIMENTAL
            / number=2
            / standardname="Translation of synthetic DNA sequence"

( x ) PUBLICATION INFORMATION:
        ( A ) AUTHORS: Ferrari, Franco A
                  Trach, Kathleen
                  Hoch, James A
        ( B ) TITLE: Seqquence Analysis of the spo0B Locus Reveals a Polycistronic Transcription Unit
        ( C ) JOURNAL: J. Bacteriol.
        ( D ) VOLUME: 161
        ( E ) ISSUE: 2
        ( F ) PAGES: 556-562
        ( G ) DATE: Feb.-1985

( x i ) SEQUENCE DESCRIPTION: SEQ ID NO:13:

```
AGC CCG TCA GTA TCG GCG GAA ATC CAG CTG AGC GCC GGT CGC TAC CAT        48
Ser Pro Ser Val Ser Ala Glu Ile Gln Leu Ser Ala Gly Arg Tyr His
 1               5                  10                  15

TAC CAG TTG GTC TGG TGT CAA AAA GAT CCA TAATTAATTA ACCCGGGTCG          98
Tyr Gln Leu Val Trp Cys Gln Lys Asp Pro
            20                   1

AAGAC                                                                 103
```

( 2 ) INFORMATION FOR SEQ ID NO:14:

( i ) SEQUENCE CHARACTERISTICS:

(A) LENGTH: 24 amino acids
            (B) TYPE: amino acid
            (D) TOPOLOGY: linear (ii) MOLECULE TYPE: protein (xi) SEQUENCE DESCRIPTION: SEQ ID NO:14:

Ser Pro Ser Val Ser Ala Glu Ile Gln Leu Ser Ala Gly Arg Tyr His
 1               5                  10                  15
Tyr Gln Leu Val Trp Cys Gln Lys
             20

(2) INFORMATION FOR SEQ ID NO:15:

(i) SEQUENCE CHARACTERISTICS:
            (A) LENGTH: 2 amino acids
            (B) TYPE: amino acid
            (D) TOPOLOGY: linear (ii) MOLECULE TYPE: protein (xi) SEQUENCE DESCRIPTION: SEQ ID NO:15:

Asp Pro
 1

(2) INFORMATION FOR SEQ ID NO:16:

(i) SEQUENCE CHARACTERISTICS:
            (A) LENGTH: 48 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Plasmid (vii) IMMEDIATE SOURCE:
            (B) CLONE: 520-17.5 (Junction D)

(xi) SEQUENCE DESCRIPTION: SEQ ID NO:16:

AGATCCCCGG GCGAGCTCGA ATTCGTAATC ATGGTCATAG CTGTTTCC                    48

(2) INFORMATION FOR SEQ ID NO:17:

(i) SEQUENCE CHARACTERISTICS:
            (A) LENGTH: 57 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Plasmid (vii) IMMEDIATE SOURCE:
            (B) CLONE: 538-46.26 (Junction A)

(xi) SEQUENCE DESCRIPTION: SEQ ID NO:17:

CACATACGAT TTAGGTGACA CTATAGAATA CAAGCTTTAT ACCATTATAG ATACATT         57

(2) INFORMATION FOR SEQ ID NO:18:

( i ) SEQUENCE CHARACTERISTICS:
                ( A ) LENGTH: 102 base pairs
                ( B ) TYPE: nucleic acid
                ( C ) STRANDEDNESS: double
                ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Plasmid ( v i i ) IMMEDIATE SOURCE:
                ( B ) CLONE: 538-46.16 (Junction B)

( i x ) FEATURE:
                ( A ) NAME/KEY: CDS
                ( B ) LOCATION: 91..102
                ( C ) IDENTIFICATION METHOD: experimental
                ( D ) OTHER INFORMATION: /partial
                        / codonstart=91
                        / function="marker enzyme"
                        / product="Beta-Galactosidase"
                        / evidence=EXPERIMENTAL
                        / gene="lacZ"
                        / number=2
                        / citation=([1])

( i x ) FEATURE:
                ( A ) NAME/KEY: CDS
                ( B ) LOCATION: 76..90
                ( D ) OTHER INFORMATION: /partial
                        / codonstart=76
                        / function="Translational start of hybrid protein"
                        / product="N-terminal peptide"
                        / number=1
                        / standardname="Translation of synthetic DNA
                        sequence"

( x ) PUBLICATION INFORMATION:
                ( A ) AUTHORS: Ferrari, Franco A
                               Trach, Kathleen
                               Hoch, James A
                ( B ) TITLE: Seqquence Analysis of the spo0B Locus Reveals
                             a Polycistronic Transcription Unit
                ( C ) JOURNAL: J. Bacteriol.
                ( D ) VOLUME: 161
                ( E ) ISSUE: 2
                ( F ) PAGES: 556-562
                ( G ) DATE: Feb.-1985

( x i ) SEQUENCE DESCRIPTION: SEQ ID NO:18:

AAGCTGGTAG ATTTCCATGT AGGGCCGCCT GCAGGTCGAC TCTAGAATTT CATTTGTTT         60

TTTTCTATGC TATAA ATG AAT TCG GAT CCC GTC GTT TTA CAA                    102
                  Met Asn Ser Asp Pro Val Val Leu Gln
                   1               5       1

( 2 ) INFORMATION FOR SEQ ID NO:19:

( i ) SEQUENCE CHARACTERISTICS:
                ( A ) LENGTH: 5 amino acids
                ( B ) TYPE: amino acid
                ( D ) TOPOLOGY: linear ( i i ) MOLECULE TYPE: protein ( x i ) SEQUENCE DESCRIPTION: SEQ ID NO:19:

Met Asn Ser Asp Pro
 1               5

( 2 ) INFORMATION FOR SEQ ID NO:20:

( i ) SEQUENCE CHARACTERISTICS:

```
            ( A ) LENGTH: 4 amino acids
            ( B ) TYPE: amino acid
            ( D ) TOPOLOGY: linear ( i i ) MOLECULE TYPE: protein ( x i ) SEQUENCE DESCRIPTION: SEQ ID NO:20:

Val Val Leu Gln
 1

( 2 ) INFORMATION FOR SEQ ID NO:21:

( i ) SEQUENCE CHARACTERISTICS:
                ( A ) LENGTH: 206 base pairs
                ( B ) TYPE: nucleic acid
                ( C ) STRANDEDNESS: double
                ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Plasmid ( v i i ) IMMEDIATE SOURCE:
                ( B ) CLONE: 538-46.16 (Junction C)

( i x ) FEATURE:
                ( A ) NAME/KEY: CDS
                ( B ) LOCATION: 1..63
                ( C ) IDENTIFICATION METHOD: experimental
                ( D ) OTHER INFORMATION: /partial
                        / codonstart=1
                        / function="marker enzyme"
                        / product="Beta-galactosidase"
                        / evidence=EXPERIMENTAL
                        / number=1
                        / citation=([1])

( i x ) FEATURE:
                ( A ) NAME/KEY: CDS
                ( B ) LOCATION: 64..69
                ( C ) IDENTIFICATION METHOD: experimental
                ( D ) OTHER INFORMATION: /codonstart=64
                        / function="Translational finish of hybrid
                          protein"
                        / product="C-terminal peptide"
                        / evidence=EXPERIMENTAL
                        / standardname="Translation of synthetic DNA
                          sequence"

( i x ) FEATURE:
                ( A ) NAME/KEY: CDS
                ( B ) LOCATION: 177..185
                ( C ) IDENTIFICATION METHOD: experimental
                ( D ) OTHER INFORMATION: /codonstart=177
                        / function="Translational start of hybrid protein"
                        / product="N-terminal peptide"
                        / evidence=EXPERIMENTAL
                        / standardname="Translation of synthetic DNA
                          sequence"

( i x ) FEATURE:
                ( A ) NAME/KEY: CDS
                ( B ) LOCATION: 186..206
                ( C ) IDENTIFICATION METHOD: experimental
                ( D ) OTHER INFORMATION: /partial
                        / codonstart=186
                        / function="glycoprotein"
                        / product="PRV gp50"
                        / evidence=EXPERIMENTAL
                        / gene="gp50"
                        / number=3
                        / citation=([2])

( x ) PUBLICATION INFORMATION:
                ( A ) AUTHORS: Ferrari, Franco A
```

Trach, Kathleen
Hoch, James A
(B) TITLE: Seqquence Analysis of the spo0B Locus Reveals a Polycistronic Transcription Unit
(C) JOURNAL: J. Bacteriol.
(D) VOLUME: 161
(E) ISSUE: 2
(F) PAGES: 556-562
(G) DATE: Feb.-1985

(x) PUBLICATION INFORMATION:
(A) AUTHORS: Petrovskis, Erik A
Timmins, James G
Armentrout, Marty A
Marchioli, Carmine C
Jr. Yancy, Robert J
Post, Leonard E
(B) TITLE: DNA Sequence of the Gene for Pseudorabies Virus gp50, a Glycoprotein without N-Linked Glycosylation
(C) JOURNAL: J. Virol.
(D) VOLUME: 59
(E) ISSUE: 2
(F) PAGES: 216-223
(G) DATE: Aug.-1986

(xi) SEQUENCE DESCRIPTION: SEQ ID NO:21:

```
GTA TCG GCG GAA ATC CAG CTG AGC GCC GGT CGC TAC CAT TAC CAG TTG         48
Val Ser Ala Glu Ile Gln Leu Ser Ala Gly Arg Tyr His Tyr Gln Leu
 1               5                  10                  15

GTC TGG TGT CAA AAA GAT CCA TAATTAATTA ACCCGGCCGC CTGCAGGTCG            99
Val Trp Cys Gln Lys Asp Pro
             20            1

ACTCTAGAAA AAATTGAAAA ACTATTCTAA TTTATTGCAC GGAGATCTTT TTTTTTTTT       159

TTTTTTTTGG CATATAA ATG AAT TCG CTC GCA GCG CTA TTG GCG GCG             206
                   Met Asn Ser Leu Ala Ala Leu Leu Ala Ala
                    1               1               5
```

(2) INFORMATION FOR SEQ ID NO:22:

(i) SEQUENCE CHARACTERISTICS:
(A) LENGTH: 21 amino acids
(B) TYPE: amino acid
(D) TOPOLOGY: linear (ii) MOLECULE TYPE: protein (xi) SEQUENCE DESCRIPTION: SEQ ID NO:22:

```
Val Ser Ala Glu Ile Gln Leu Ser Ala Gly Arg Tyr His Tyr Gln Leu
 1               5                  10                  15
Val Trp Cys Gln Lys
             20
```

(2) INFORMATION FOR SEQ ID NO:23:

(i) SEQUENCE CHARACTERISTICS:
(A) LENGTH: 2 amino acids
(B) TYPE: amino acid
(D) TOPOLOGY: linear (ii) MOLECULE TYPE: protein (xi) SEQUENCE DESCRIPTION: SEQ ID NO:23:

Asp Pro
 1

(2) INFORMATION FOR SEQ ID NO:24:

(i) SEQUENCE CHARACTERISTICS:
(A) LENGTH: 3 amino acids
(B) TYPE: amino acid (D) TOPOLOGY: linear (i i) MOLECULE TYPE: protein (x i) SEQUENCE DESCRIPTION: SEQ ID NO:24:

Met Asn Ser
 1

(2) INFORMATION FOR SEQ ID NO:25:

(i) SEQUENCE CHARACTERISTICS:
        (A) LENGTH: 7 amino acids
        (B) TYPE: amino acid
        (D) TOPOLOGY: linear (i i) MOLECULE TYPE: protein (x i) SEQUENCE DESCRIPTION: SEQ ID NO:25:

Leu Ala Ala Leu Leu Ala Ala
 1                   5

(2) INFORMATION FOR SEQ ID NO:26:

(i) SEQUENCE CHARACTERISTICS:
        (A) LENGTH: 101 base pairs
        (B) TYPE: nucleic acid
        (C) STRANDEDNESS: double
        (D) TOPOLOGY: circular (i i) MOLECULE TYPE: DNA (genomic)

(i i i) HYPOTHETICAL: NO (i v) ANTI-SENSE: NO (v i) ORIGINAL SOURCE:
        (A) ORGANISM: Plasmid (v i i) IMMEDIATE SOURCE:
        (B) CLONE: 538-46.16 (Junction D)

(i x) FEATURE:
        (A) NAME/KEY: CDS
        (B) LOCATION: 1..15
        (D) OTHER INFORMATION: /partial
            / codonstart=1
            / function="glycoprotein"
            / product="PRV gp63"
            / gene="gp63"
            / number=1
            / citation=([1])

(x) PUBLICATION INFORMATION:
        (A) AUTHORS: Petrovskis, Erik A
            Timmins, James G
            Post, Leonard E
        (B) TITLE: Use of Lambda-gt11 To Isolate Genes for two
            Pseudorabies Virus Glycoproteins with homology to
            Herpes Simplex Virus and Varicella-Zoster Virus
            Glycoproteins
        (C) JOURNAL: J. Virol.
        (D) VOLUME: 60
        (E) ISSUE: 1
        (F) PAGES: 185-193
        (G) DATE: Oct.-1986

(x i) SEQUENCE DESCRIPTION: SEQ ID NO:26:

```
CGC GTG CAC CAC GAG GGACTCTAGA GGATCCATAA TTAATTAATT AATTTTTATC      55
Arg Val His His Glu
 1               5

CCGGGTCGAC CTGCAGGCGG CCGGGTCGAC CTGCAGGCGG CCAGAC                  101
```

(2) INFORMATION FOR SEQ ID NO:27:

(i) SEQUENCE CHARACTERISTICS:

(A) LENGTH: 5 amino acids
                (B) TYPE: amino acid
                (D) TOPOLOGY: linear (ii) MOLECULE TYPE: protein (xi) SEQUENCE DESCRIPTION: SEQ ID NO:27:

Arg Val His His Glu
 1               5

(2) INFORMATION FOR SEQ ID NO:28:

(i) SEQUENCE CHARACTERISTICS:
                (A) LENGTH: 57 base pairs
                (B) TYPE: nucleic acid
                (C) STRANDEDNESS: double
                (D) TOPOLOGY: circular (ii) MOLECULE TYPE: DNA (genomic)

(iii) HYPOTHETICAL: NO (iv) ANTI-SENSE: NO (vi) ORIGINAL SOURCE:
                (A) ORGANISM: Plasmid (vii) IMMEDIATE SOURCE:
                (B) CLONE: 538-46.16 (Junction E)

(xi) SEQUENCE DESCRIPTION: SEQ ID NO:28:

AGATCCCCGG GCGAGCTCGA ATTCGTAATC ATGGTCATAG CTGTTTCCTG TGTGAAA      57

(2) INFORMATION FOR SEQ ID NO:29:

(i) SEQUENCE CHARACTERISTICS:
                (A) LENGTH: 1907 base pairs
                (B) TYPE: nucleic acid
                (C) STRANDEDNESS: double
                (D) TOPOLOGY: linear (ii) MOLECULE TYPE: cDNA to mRNA (iii) HYPOTHETICAL: NO (iv) ANTI-SENSE: NO (vi) ORIGINAL SOURCE:
                (A) ORGANISM: Newcastle disease virus
                (B) STRAIN: B1

(vii) IMMEDIATE SOURCE:
                (B) CLONE: 137-

```
ATA TTC CGG ATT GCA ATC TTA TTC TTA ACA GTA GTG ACC TTG GCT ATA      208
Ile Phe Arg Ile Ala Ile Leu Phe Leu Thr Val Val Thr Leu Ala Ile
    25                  30                  35

TCT GTA GCC TCC CTT TTA TAT AGC ATG GGG GCT AGC ACA CCT AGC GAT      256
Ser Val Ala Ser Leu Leu Tyr Ser Met Gly Ala Ser Thr Pro Ser Asp
 40                  45                  50                  55

CTT GTA GGC ATA CCG ACT AGG ATT TCC AGG GCA GAA GAA AAG ATT ACA      304
Leu Val Gly Ile Pro Thr Arg Ile Ser Arg Ala Glu Glu Lys Ile Thr
            60                  65                  70

TCT ACA CTT GGT TCC AAT CAA GAT GTA GTA GAT AGG ATA TAT AAG CAA      352
Ser Thr Leu Gly Ser Asn Gln Asp Val Val Asp Arg Ile Tyr Lys Gln
         75                  80                  85

GTG GCC CTT GAG TCT CCA TTG GCA TTG TTA AAT ACT GAG ACC ACA ATT      400
Val Ala Leu Glu Ser Pro Leu Ala Leu Leu Asn Thr Glu Thr Thr Ile
         90                  95                 100

ATG AAC GCA ATA ACA TCT CTC TCT TAT CAG ATT AAT GGA GCT GCA AAC      448
Met Asn Ala Ile Thr Ser Leu Ser Tyr Gln Ile Asn Gly Ala Ala Asn
    105                 110                 115

AAC AGC GGG TGG GGG GCA CCT ATT CAT GAC CCA GAT TAT ATA GGG GGG      496
Asn Ser Gly Trp Gly Ala Pro Ile His Asp Pro Asp Tyr Ile Gly Gly
120                 125                 130                 135

ATA GGC AAA GAA CTC ATT GTA GAT GAT GCT AGT GAT GTC ACA TCA TTC      544
Ile Gly Lys Glu Leu Ile Val Asp Asp Ala Ser Asp Val Thr Ser Phe
                140                 145                 150

TAT CCC TCT GCA TTT CAA GAA CAT CTG AAT TTT ATC CCG GCG CCT ACT      592
Tyr Pro Ser Ala Phe Gln Glu His Leu Asn Phe Ile Pro Ala Pro Thr
            155                 160                 165

ACA GGA TCA GGT TGC ACT CGA ATA CCC TCA TTT GAC ATG AGT GCT ACC      640
Thr Gly Ser Gly Cys Thr Arg Ile Pro Ser Phe Asp Met Ser Ala Thr
         170                 175                 180

CAT TAC TGC TAC ACC CAT AAT GTA ATA TTG TCT GGA TGC AGA GAT CAC      688
His Tyr Cys Tyr Thr His Asn Val Ile Leu Ser Gly Cys Arg Asp His
         185                 190                 195

TCA CAC TCA CAT CAG TAT TTA GCA CTT GGT GTG CTC CGG ACA TCT GCA      736
Ser His Ser His Gln Tyr Leu Ala Leu Gly Val Leu Arg Thr Ser Ala
200                 205                 210                 215

ACA GGG AGG GTA TTC TTT TCT ACT CTG CGT TCC ATC AAC CTG GAC GAC      784
Thr Gly Arg Val Phe Phe Ser Thr Leu Arg Ser Ile Asn Leu Asp Asp
                220                 225                 230

ACC CAA AAT CGG AAG TCT TGC AGT GTG AGT GCA ACT CCC CTG GGT TGT      832
Thr Gln Asn Arg Lys Ser Cys Ser Val Ser Ala Thr Pro Leu Gly Cys
            235                 240                 245

GAT ATG CTG TGC TCG AAA GCC ACG GAG ACA GAG GAA GAA GAT TAT AAC      880
Asp Met Leu Cys Ser Lys Ala Thr Glu Thr Glu Glu Glu Asp Tyr Asn
         250                 255                 260

TCA GCT GTC CCT ACG CGG ATG GTA CAT GGG AGG TTA GGG TTC GAC GGC      928
Ser Ala Val Pro Thr Arg Met Val His Gly Arg Leu Gly Phe Asp Gly
         265                 270                 275

CAA TAT CAC GAA AAG GAC CTA GAT GTC ACA ACA TTA TTC GGG GAC TGG      976
Gln Tyr His Glu Lys Asp Leu Asp Val Thr Thr Leu Phe Gly Asp Trp
280                 285                 290                 295

GTG GCC AAC TAC CCA GGA GTA GGG GGT GGA TCT TTT ATT GAC AGC CGC     1024
Val Ala Asn Tyr Pro Gly Val Gly Gly Ser Phe Ile Asp Ser Arg
                300                 305                 310

GTG TGG TTC TCA GTC TAC GGA GGG TTA AAA CCC AAT ACA CCC AGT GAC     1072
Val Trp Phe Ser Val Tyr Gly Gly Leu Lys Pro Asn Thr Pro Ser Asp
            315                 320                 325

ACT GTA CAG GAA GGG AAA TAT GTG ATA TAC AAG CGA TAC AAT GAC ACA     1120
Thr Val Gln Glu Gly Lys Tyr Val Ile Tyr Lys Arg Tyr Asn Asp Thr
         330                 335                 340

TGC CCA GAT GAG CAA GAC TAC CAG ATT CGA ATG GCC AAG TCT TCG TAT     1168
```

```
              Cys Pro Asp Glu Gln Asp Tyr Gln Ile Arg Met Ala Lys Ser Ser Tyr
              345                 350                 355

AAG CCT GGA CGG TTT GGT GGG AAA CGC ATA CAG CAG GCT ATC TTA TCT           1216
Lys Pro Gly Arg Phe Gly Gly Lys Arg Ile Gln Gln Ala Ile Leu Ser
360                 365                 370                 375

ATC AAA GTG TCA ACA TCC TTA GGC GAA GAC CCG GTA CTG ACT GTA CCG           1264
Ile Lys Val Ser Thr Ser Leu Gly Glu Asp Pro Val Leu Thr Val Pro
            380                 385                 390

CCC AAC ACA GTC ACA CTC ATG GGG GCC GAA GGC AGA ATT CTC ACA GTA           1312
Pro Asn Thr Val Thr Leu Met Gly Ala Glu Gly Arg Ile Leu Thr Val
                395                 400                 405

GGG ACA TCC CAT TTC TTG TAT CAG CGA GGG TCA TCA TAC TTC TCT CCC           1360
Gly Thr Ser His Phe Leu Tyr Gln Arg Gly Ser Ser Tyr Phe Ser Pro
410                 415                 420

GCG TTA TTA TAT CCT ATG ACA GTC AGC AAC AAA ACA GCC ACT CTT CAT           1408
Ala Leu Leu Tyr Pro Met Thr Val Ser Asn Lys Thr Ala Thr Leu His
425                 430                 435

AGT CCT TAT ACA TTC AAT GCC TTC ACT CGG CCA GGT AGT ATC CCT TGC           1456
Ser Pro Tyr Thr Phe Asn Ala Phe Thr Arg Pro Gly Ser Ile Pro Cys
440                 445                 450                 455

CAG GCT TCA GCA AGA TGC CCC AAC TCA TGT GTT ACT GGA GTC TAT ACA           1504
Gln Ala Ser Ala Arg Cys Pro Asn Ser Cys Val Thr Gly Val Tyr Thr
                460                 465                 470

GAT CCA TAT CCC CTA ATC TTC TAT AGA AAC CAC ACC TTG CGA GGG GTA           1552
Asp Pro Tyr Pro Leu Ile Phe Tyr Arg Asn His Thr Leu Arg Gly Val
            475                 480                 485

TTC GGG ACA ATG CTT GAT GGT GAA CAA GCA AGA CTT AAC CCT GCG TCT           1600
Phe Gly Thr Met Leu Asp Gly Glu Gln Ala Arg Leu Asn Pro Ala Ser
        490                 495                 500

GCA GTA TTC GAT AGC ACA TCC CGC AGT CGC ATA ACT CGA GTG AGT TCA           1648
Ala Val Phe Asp Ser Thr Ser Arg Ser Arg Ile Thr Arg Val Ser Ser
    505                 510                 515

AGC AGC ATC AAA GCA GCA TAC ACA ACA TCA ACT TGT TTT AAA GTG GTC           1696
Ser Ser Ile Lys Ala Ala Tyr Thr Thr Ser Thr Cys Phe Lys Val Val
520                 525                 530                 535

AAG ACC AAT AAG ACC TAT TGT CTC AGC ATT GCT GAA ATA TCT AAT ACT           1744
Lys Thr Asn Lys Thr Tyr Cys Leu Ser Ile Ala Glu Ile Ser Asn Thr
                540                 545                 550

CTC TTC GGA GAA TTC AGA ATC GTC CCG TTA CTA GTT GAG ATC CTC AAA           1792
Leu Phe Gly Glu Phe Arg Ile Val Pro Leu Leu Val Glu Ile Leu Lys
            555                 560                 565

GAT GAC GGG GTT AGA GAA GCC AGG TCT GGC TAGTTGAGTC AACTATGAAA             1842
Asp Asp Gly Val Arg Glu Ala Arg Ser Gly
570                 575

GAGTTGGAAA GATGGCATTG TATCACCTAT CTTCTGCGAC ATCAAGAATC AAACCGAATG         1902

CCGGC                                                                     1907
```

( 2 ) INFORMATION FOR SEQ ID NO:30:

( i ) SEQUENCE CHARACTERISTICS:
      ( A ) LENGTH: 577 amino acids
      ( B ) TYPE: amino acid
      ( D ) TOPOLOGY: linear ( ii ) MOLECULE TYPE: protein ( xi ) SEQUENCE DESCRIPTION: SEQ ID NO:30:

```
Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
```

-continued

```
              35                    40                    45
Gly Ala Ser Thr Pro Ser Asp Leu Val Gly Ile Pro Thr Arg Ile Ser
    50                  55                  60
Arg Ala Glu Glu Lys Ile Thr Ser Thr Leu Gly Ser Asn Gln Asp Val
65                  70                  75                  80
Val Asp Arg Ile Tyr Lys Gln Val Ala Leu Glu Ser Pro Leu Ala Leu
                85                  90                  95
Leu Asn Thr Glu Thr Thr Ile Met Asn Ala Ile Thr Ser Leu Ser Tyr
            100                 105                 110
Gln Ile Asn Gly Ala Ala Asn Asn Ser Gly Trp Gly Ala Pro Ile His
        115                 120                 125
Asp Pro Asp Tyr Ile Gly Gly Ile Gly Lys Glu Leu Ile Val Asp Asp
    130                 135                 140
Ala Ser Asp Val Thr Ser Phe Tyr Pro Ser Ala Phe Gln Glu His Leu
145                 150                 155                 160
Asn Phe Ile Pro Ala Pro Thr Thr Gly Ser Gly Cys Thr Arg Ile Pro
                165                 170                 175
Ser Phe Asp Met Ser Ala Thr His Tyr Cys Tyr Thr His Asn Val Ile
            180                 185                 190
Leu Ser Gly Cys Arg Asp His Ser His Ser His Gln Tyr Leu Ala Leu
        195                 200                 205
Gly Val Leu Arg Thr Ser Ala Thr Gly Arg Val Phe Phe Ser Thr Leu
    210                 215                 220
Arg Ser Ile Asn Leu Asp Asp Thr Gln Asn Arg Lys Ser Cys Ser Val
225                 230                 235                 240
Ser Ala Thr Pro Leu Gly Cys Asp Met Leu Cys Ser Lys Ala Thr Glu
                245                 250                 255
Thr Glu Glu Glu Asp Tyr Asn Ser Ala Val Pro Thr Arg Met Val His
            260                 265                 270
Gly Arg Leu Gly Phe Asp Gly Gln Tyr His Glu Lys Asp Leu Asp Val
        275                 280                 285
Thr Thr Leu Phe Gly Asp Trp Val Ala Asn Tyr Pro Gly Val Gly Gly
    290                 295                 300
Gly Ser Phe Ile Asp Ser Arg Val Trp Phe Ser Val Tyr Gly Gly Leu
305                 310                 315                 320
Lys Pro Asn Thr Pro Ser Asp Thr Val Gln Glu Gly Lys Tyr Val Ile
                325                 330                 335
Tyr Lys Arg Tyr Asn Asp Thr Cys Pro Asp Glu Gln Asp Tyr Gln Ile
            340                 345                 350
Arg Met Ala Lys Ser Ser Tyr Lys Pro Gly Arg Phe Gly Gly Lys Arg
        355                 360                 365
Ile Gln Gln Ala Ile Leu Ser Ile Lys Val Ser Thr Ser Leu Gly Glu
    370                 375                 380
Asp Pro Val Leu Thr Val Pro Pro Asn Thr Val Thr Leu Met Gly Ala
385                 390                 395                 400
Glu Gly Arg Ile Leu Thr Val Gly Thr Ser His Phe Leu Tyr Gln Arg
                405                 410                 415
Gly Ser Ser Tyr Phe Ser Pro Ala Leu Leu Tyr Pro Met Thr Val Ser
            420                 425                 430
Asn Lys Thr Ala Thr Leu His Ser Pro Tyr Thr Phe Asn Ala Phe Thr
        435                 440                 445
Arg Pro Gly Ser Ile Pro Cys Gln Ala Ser Ala Arg Cys Pro Asn Ser
    450                 455                 460
Cys Val Thr Gly Val Tyr Thr Asp Pro Tyr Pro Leu Ile Phe Tyr Arg
465                 470                 475                 480
```

| | | | | | | | | | | | | | |
|---|---|---|---|---|---|---|---|---|---|---|---|---|---|
|Asn|His|Thr|Leu|Arg<br>485|Gly|Val|Phe|Gly|Thr<br>490|Met|Leu|Asp|Gly<br>495|Gln|
|Ala|Arg|Leu|Asn|Pro<br>500|Ala|Ser|Ala|Val<br>505|Phe|Asp|Ser|Thr|Ser<br>510|Arg|Ser|
|Arg|Ile|Thr<br>515|Arg|Val|Ser|Ser|Ser<br>520|Ser|Ile|Lys|Ala|Ala<br>525|Tyr|Thr|Thr|
|Ser|Thr<br>530|Cys|Phe|Lys|Val|Val<br>535|Lys|Thr|Asn|Lys|Thr<br>540|Tyr|Cys|Leu|Ser|
|Ile<br>545|Ala|Glu|Ile|Ser|Asn<br>550|Thr|Leu|Phe|Gly|Glu<br>555|Phe|Arg|Ile|Val|Pro<br>560|
|Leu|Leu|Val|Glu|Ile<br>565|Leu|Lys|Asp|Asp|Gly<br>570|Val|Arg|Glu|Ala|Arg<br>575|Ser|

Gly ( 2 ) INFORMATION FOR SEQ ID NO:31:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction A)

( x i ) SEQUENCE DESCRIPTION: SEQ ID NO:31:

CACATACGAT TTAGGTGACA CTATAGAATA CAAGCTTTAT ACCATTATAG ATACATT      57

( 2 ) INFORMATION FOR SEQ ID NO:32:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction B)

( i x ) FEATURE:
        ( A ) NAME/KEY: exon
        ( B ) LOCATION: 88..102
        ( D ) OTHER INFORMATION: /codonstart=88
            / function="Translational start of hybrid protein"
            / product="N-terminal peptide"
            / number=1
            / standardname="Translation of synthetic DNA
        sequence"

( i x ) FEATURE:
        ( A ) NAME/KEY: CDS
        ( B ) LOCATION: 103..108
        ( C ) IDENTIFICATION METHOD: experimental
        ( D ) OTHER INFORMATION: /partial / codonstart=103
/ product="NDV Heamagglutinin-Neuraminidase"
/ evidence=E ( E ) ISSUE: 2
( F ) PAGES: 556-562
( G ) DATE: Feb.-1985

( x i ) SEQUENCE DESCRIPTION: SEQ ID NO:34:

```
TGCGACATCA AGAATCAAAC CGAATGCCCT CGACTCTAGA ATTTCATTTT GTTTTTTCT      60

ATGCTATAA ATG AAT TCG GAT CCC GTC GTT TTA CAA CGT CGT GAC TGG        108
          Met Asn Ser Asp Pro Val Val Leu Gln Arg Arg Asp Trp
          1               5                   1           5
```

( 2 ) INFORMATION FOR SEQ ID NO:35:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

```
Met Asn Ser Asp Pro
1               5
```

( 2 ) INFORMATION FOR SEQ ID NO:36:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Val Val Leu Gln Arg Arg Asp Trp
1               5
```

( 2 ) INFORMATION FOR SEQ ID NO:37:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26

( i x ) FEATURE:
        ( A ) NAME/KEY: CDS
        ( B ) LOCATION: 1..54
        ( C ) IDENTIFICATION METHOD: experimental
        ( D ) OTHER INFORMATION: /partial
            / codonstart = 1
            / function = "marker enzyme"
            / product = "Beta-galactosidase"
            / evidence = EXPERIMENTAL
            / gene = "lacZ"
            / number = 1
            / citation = ([1])

( i x ) FEATURE:
        ( A ) NAME/KEY: CDS
        ( B ) LOCATION: 55..63
        ( C ) IDENTIFICATION METHOD: experimental
        ( D ) OTHER INFORMATION: /codonstart = 55

/ function="Translational finish of hybrid protein"
/ product="C-terminal peptide"
/ evidence=EXPERIMENTAL
/ number=2
/ standardname="Translation of synthetic DNA sequence"

( x i ) SEQUENCE DESCRIPTION: SEQ ID NO:37:

```
GAA ATC CAG CTG AGC GCC GGT CGC TAC CAT TAC CAG TTG GTC TGG TGT      48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG AGGGTCGAAG ACCAAATTCT          100
Gln Lys Asp Pro
             1

AACATGGT                                                             108
```

( 2 ) INFORMATION FOR SEQ ID NO:38:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Glu Ile Gln Leu Ser Ala Gly Arg Tyr His Tyr Gln Leu Val Trp Cys
 1               5                  10                  15

Gln Lys
```

( 2 ) INFORMATION FOR SEQ ID NO:39:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

```
Asp Pro
 1
```

( 2 ) INFORMATION FOR SEQ ID NO:40:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction E)

( x i ) SEQUENCE DESCRIPTION: SEQ ID NO:40:

```
AGATCCCCGG GCGAGCTCGA ATTCGTAATC ATGGTCATAG CTGTTTCCTG TGTGAAA      57
```

( 2 ) INFORMATION FOR SEQ ID NO:41:

( i ) SEQUENCE CHARACTERISTICS:
        ( A ) LENGTH: 27 base pairs ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
        ( A ) ORGANISM: Pseudorabies virus
Synthetic oligonucleotide primer ( x i ) SEQUENCE DESCRIPTION: SEQ ID NO:41:

CGCGAATTCG CTCGCAGCGC TATTGGC                   27

( 2 ) INFORMATION FOR SEQ ID NO:42:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
( A ) ORGANISM: Pseudorabies virus
Synthetic oligonucleotide primer ( x i ) SEQUENCE DESCRIPTION: SEQ ID NO:42:

GTAGGAGTGG CTGCTGAAG 19

What is claimed is:

1. A recombinant swinepox virus which comprises a foreign DNA inserted within the swinepox virus genomic DNA, wherein the foreign DNA sequence is inserted within the larger HindIII to BglII subfragment of the HindIII M fragment of the genomic DNA, and is capable of being expressed in a swinepox virus infected hose cell.

2. The recombinant swinepox virus of claim 1, wherein the insertion site is within an open reading frame contained within the HindIII to BglII subfragment, wherein the open reading frame contains the unique AccI site present in the HindIII to BglII subfragment.

3. The recombinant swinepox virus of claim 2, wherein the insertion size is the AccI restriction endonuclease site located in the HindIII to BglII subfragment.

4. The recombinant swinepox virus of claim 1, wherein the recombinant swinepox virus further comprises a foreign DNA sequence inserted within the swinepox virus thymidine kinase gene.

5. The recombinant swinepox virus of claim 1, wherein the foreign DNA sequence encodes a detectable marker.

6. The recombinant swinepox virus of claim 5, wherein the detectable marker is *E. coli* β-galactosidase.

7. The recombinant swinepox virus of claim 6, designated S-SPV-003 (ATCC Accession No. VR 2335).

8. The recombinant swinepox virus of claim 1, wherein the foreign DNA sequence encodes an antigenic polypeptide.

9. The recombinant swinepox virus of claim 8, wherein the antigenic polypeptide is selected from the group consisting essentially of PRV glycoprotein 50, PRV glycoprotein II, PRV glycoprotein III, PRV glycoprotein H, TGE glycoprotein 195, TGE matrix protein,, swine rotavirus glycoprotein 38, swine parvovirus capsid protein, *Serpulina hyodysenteriae* protective antigen, BVDV glycoprotein 55, NDV hemagglutinin-neuraminidase, swine flu hemagglutinin and swine flu neuraminidase.

10. The recombinant swinepox virus of claim 9, wherein the antigenic polypeptide is PRV glycoprotein 50.

11. The recombinant swinepox virus of claim 10, designated S-SPV-008 (ATCC Accession No. VR 2339).

12. A homology vector for producing a recombinant swinepox virus by inserting a foreign DNA sequence into the genomic DNA of a swinepox virus which comprises a foreign DNA sequence, wherein the foreign DNA sequence is controlled by a promoter and flanked by a nucleotide sequence homologous to the swinepox virus genomic DNA present within the HindIII to BglII subfragment of HindIII M fragment.

13. The homology vector of claim 12, wherein the nucleotide sequence flanking the foreign DNA sequence is homologous to the swinepox virus genomic DNA present within the AccI restriction endonuclease site located in the HindIII to BglII subfragment.

14. The homology vector of claim 12, wherein the foreign DNA sequence encodes a detectable marker.

15. The homology vector of claim 13, wherein the detectable marker is *E. coli* β-galactosidase.

16. The homology vector of claim 12, wherein the foreign DNA sequence encodes an antigenic polypeptide.

17. The homology vector of claim 16, wherein the antigenic polypeptide is pseudorabies virus glycoprotein 50.

18. A recombinant swinepox virus of claim 8, wherein the antigenic polypeptide is or is from, Foot and Mouth Disease Virus, Hog Cholera Virus, Swine Influenza Virus, African Swine Fever Virus or *Mycoplasma hyopneumoniae*.

19. A recombinant swinepox virus of claim 8, designated S-SPV-009 (ATCC Accession No. VR 2344).

20. A homology vector of claim 16, wherein the antigenic polypeptide is or is from *Serpulina hyodysenteriae*, Foot and Mouth Disease Virus, Hog Cholera Virus, Swine Influenza Virus, African Swine Fever Virus or *Mycoplasma hyopneumoniae*.

* * * * *